United States Patent [19]
Bodor

[11] Patent Number: 5,413,996
[45] Date of Patent: May 9, 1995

[54] TARGETED DRUG DELIVERY VIA PHOSPHONATE DERIVATIVES

[75] Inventor: Nicholas S. Bodor, Gainesville, Fla.

[73] Assignee: University of Florida, Gainesville, Fla.

[21] Appl. No.: 962,504

[22] Filed: Oct. 16, 1992

Related U.S. Application Data

[62] Division of Ser. No. 553,548, Jul. 13, 1990, Pat. No. 5,177,064.

[51] Int. Cl.⁶ .................. A61K 31/56; A61K 31/66
[52] U.S. Cl. .......................... 514/169; 514/75; 514/177; 514/178; 514/179; 514/182; 536/5; 552/502; 552/540; 562/8
[58] Field of Search ........... 514/75, 169, 177, 178, 514/179, 182; 536/5; 552/502, 540; 562/8

[56] References Cited

U.S. PATENT DOCUMENTS

| | | | |
|---|---|---|---|
| 3,929,840 | 12/1975 | Christensen et al. | 260/348 A |
| 4,540,564 | 9/1985 | Bodor | 424/9 |
| 4,703,043 | 10/1987 | Karanewsky et al. | 514/80 |
| 4,816,570 | 3/1989 | Farquhar | 536/27 |
| 4,968,788 | 11/1990 | Farquhar | 536/29 |

FOREIGN PATENT DOCUMENTS 0239109  9/1987  European Pat. Off. .

OTHER PUBLICATIONS

Iyer et al, *Tetrahedron Letters*, vol. 30, No. 51, 1989, pp. 7141–7144.
*Chemical Abstracts*, vol. 112, 1990, abstract No. 69487n, Freed et al.
Farquhar et al, *J. Pharm. Sci.*, vol. 72, No. 3, Mar. 1983, 324–325.
Srivastva et al, *Bioorganic Chemistry* 12 (1984), 118–129.
Prisbe et al, *J. Med. Chem.*, 1986, 29, 671–675.
Mitsuya et al, *Science*, vol. 249, 28 Sep. 1990, 1533–1544.

*Primary Examiner*—Patricia R. Moody
*Attorney, Agent, or Firm*—Burns, Doane, Swecker & Mathis

[57] ABSTRACT

The invention provides compounds of the formula

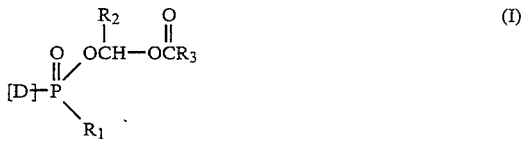

(I)

or a pharmaceutically acceptable salt thereof, wherein [D] is the residue of a drug having a reactive functional group, said functional group being attached, directly or through a bridging group, via an oxygen-phosphorus bond to the phosphorus atom of the

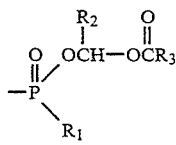

moiety; $R_1$ is $C_1$–$C_8$ alkyl, $C_6$–$C_{10}$ aryl or $C_7$–$C_{12}$ aralkyl; $R_2$ is hydrogen, $C_1$–$C_8$ alkyl, $C_6$–$C_{10}$ aryl, $C_4$–$C_9$ heteroaryl, $C_3$–$C_7$ cycloalkyl, $C_3$–$C_7$ cycloheteroalkyl or $C_7$–$C_{12}$ aralkyl; and $R_3$ is selected from the group consisting of $C_1$–$C_8$ alkyl; $C_2$–$C_8$ alkenyl having one or two double bonds; ($C_3$–$C_7$ cycloalkyl)—$C_rH_{2r}$— wherein r is zero, one, two or three, the cycloalkyl portion being unsubstituted or bearing 1 or 2 $C_1$–$C_4$ alkyl substituents on the ring portion; ($C_6$–$C_{10}$ aryloxy)$C_1$–$C_8$ alkyl; 2-, 3- or 4-pyridyl; and phenyl—$C_rH_{2r}$— wherein r is zero, one, two or three and phenyl is unsubstituted, or is substituted by 1 to 3 alkyl each having 1 to 4 carbon atoms, alkoxy having 1 to 4 carbon atoms, halo, trifluoromethyl, dialkylamino having 2 to 8 carbon atoms or alkanoylamino having 2 to 6 carbon atoms. The compounds are adapted for targeted drug delivery, especially to the brain.

17 Claims, No Drawings

TARGETED DRUG DELIVERY VIA PHOSPHONATE DERIVATIVES

This application is a divisional of application Ser. No. 07/553,548, filed Jul. 13, 1990, now U.S. Pat. No. 5,177,064.

FIELD OF THE INVENTION

The present invention relates to an anionic sequestration type of drug modification designed to enhance delivery of the active drug species to the desired site of action, especially to the brain. More especially, the present invention relates to the discovery that a biologically active compound coupled to a lipophilic carrier moiety of the acyloxyalkyl phosphonate type readily penetrates biological membranes such as the blood-brain barrier (BBB) and enters the target organ; cleavage of the phosphonate carrier/drug entity in vivo provides a hydrophilic, negatively charged intermediate which is "locked in" the brain or other organ and which provides significant and sustained delivery of the active drug species to the target organ.

BACKGROUND OF THE INVENTION

The delivery of drug species to the brain and other organs is often seriously limited by transport and metabolism factors, including biological membranes; specifically, in the case of the brain, delivery is limited by the functional barrier of the endothelial brain capillary wall, i.e. the blood-brain barrier or BBB. Site-specific and sustained delivery of drugs to the brain or other organs, i.e. targeted drug delivery, is even more difficult.

Many drugs are hydrophilic and are unable to penetrate the brain to any considerable extent. Other drugs which are lipophilic and/or for which particular transport mechanisms exist may be able to cross the BBB and reach the brain, but the very lipophilicity which enables their entry likewise facilitates their exit. It is thus necessary to administer large doses of drugs to achieve adequate brain levels (if, indeed, such is even possible), and this in turn overburdens non-targeted loci and results in significant toxicity.

It is now well-known that numerous drugs exert their biological effects through centrally-mediated mechanisms. Thus, a brain-targeted approach is a desirable means of delivery for a wide diversity of drugs, including neurotransmitters, stimulants, dopaminergic agents, tranquilizers, antidepressants, narcotic analgesics, narcotic antagonists, sedatives, hypnotics, anesthetics, antiepileptics/anticonvulsants, hormones such as the male and female sex hormones, peptides, anti-inflammatory steroids, non-steroidal anti-inflammatory agents/non-narcotic analgesics, memory enhancers, antibacterials/antibiotics, antineoplastics (anticancer/antitumor agents) and antiviral agents.

In recent years, the need for more effective treatment of a number of viral disease states has become increasingly urgent. The generally poor therapeutic accessibility of viral infections can be traced to three major facets including the viral life cycle, the lack of efficacious pharmacologically-active agents and, finally, the inability to deliver those agents which are available to the central nervous system (CNS) for sustained periods and in significant amounts.

Viruses are submicroscopic pathogens which depend on the cellular nucleic acid and protein synthesizing mechanisms of its host for propagation. In general, viruses invade cells by first interacting at a recognizable surface protein, penetrating the cell membrane and subsequently releasing themselves from a protective polypeptide coat to eject the core of the virus. The heart of these pathogens is genetic material, either DNA or RNA, and the type of nucleic acid gives rise to the system of nomenclature for these entities. The viral DNA and RNA can interact with cellular components to produce daughter genetic material as well as various structural or enzymatic proteins. After assembly and release, the viral progeny may infect other cells, yielding disease or ultimately death.

DNA viruses are subdivided into five families and include the pathogens responsible for labial and genital herpes, herpes encephalitis, human cytomegalovirus infection, chicken pox, shingles and mononucleosis. RNA viruses are present in more numerous forms and are subdivided into ten families. These viruses are unusual in that they reverse the usual DNA→RNA→ protein sequence which occurs in higher life forms. RNA viruses are unusually dangerous for several reasons, including their lethality and the lack of effective treatments. RNA viral diseases include acquired immune deficiency syndrome, hemorrhagic fevers of various descriptions, Dengue fever, Lassa fever, and numerous encephalitic maladies including Japanese B encephalitis.

Chemotherapeutically, very few antiviral agents have been developed that have high in vitro activity against these viruses. One notable advance in the field was the advent of ribavirin or 1-$\beta$-D-ribofuranosyl-1,2,4-triazole-3-carboxamide, synthesized in 1972. Ribavirin has a broad range of activity against both DNA and RNA viruses. This riboside, which contains an unnatural triazole base, significantly suppresses the infectivity and cytopathicity of several viral pathogens by mechanisms which are as of yet unclear. Several interactions have been suggested including inhibition of viral RNA polymerase, the inhibition of inosine monophosphate dehydrogenase by ribavirin anabolites and interference of mRNA cap formation by the 5'-triphosphate of ribavirin.

Ribavirin is active against several influenza viruses and respiratory syncytial virus and as such is used in an aerosol form to treat these diseases. Ribavirin is also used in the treatment of Lassa fever which rages in epidemic proportions in Sierra Leone. Unfortunately, while peripheral viral infections can be successfully treated with ribavirin and other riboside derivatives, encephalitis is immune to the action of these drugs. The inability of antiviral drugs, which are highly potent in vitro, to exert activity in the CNS is attributable to their exclusion from the brain. The basis of this impermeability is the blood-brain barrier (BBB), which effectively separates the systemic circulation from the brain parenchyma. As this barrier is lipoidal in nature, the BBB restricts the entry of materials which do not have high affinity for the phospholipid matrix and consequently hydrophilic compounds are excluded. Thus, drug molecules must be intrinsically lipophilic if they are to gain access to the CNS. This is the restriction which renders ribavirin, which has a log P of only 2.06, ineffective in treating viral diseases of the brain.

Many antiherpetic agents exhibit poor penetration across biological barriers such as the BBB and the ocular and skin barriers, achieving concentrations well below therapeutic levels. Improved delivery of an antiherpetic agent across these barriers would offer a significant advantage in the treatment of such serious and debilitating diseases as encephalitis, ophthalmic infections caused by herpes simplex such as herpetic uveites, keratitis etc. and cutaneous herpes infections such as genital and orofacial herpes.

Vidarabine (9-β-D-arabinofuranosyladenine, Ara-A, adenine arabinoside) is a purine nucleoside analog with a broad spectrum of antiviral activity against a number of DNA viruses, including HSV-1 and 2, cytomegalovirus and varicella zoster virus. The drug has been shown useful in the treatment of brain biopsy-proven herpes simplex encephalitis (HSE), resulting in a statistically significant reduction in mortality. Ara-A has demonstrated clinical utility as a topical agent for herpes keratitis of the eye. However, when applied locally to the skin, vidarabine has provided no benefit in genital or orofacial HSV infection. In immunocompromised patients with localized herpes zoster, Ara-A has demonstrated a beneficial effect in accelerating cutaneous healing and decreasing the rate of cutaneous dissemination.

The essential mechanism of inhibition of viral replication by vidarabine, although not precisely defined, appears to be a consequence of the incorporation of the drug into viral DNA. To exert its antiviral action, vidarabine must fast be phosphorylated by cellular enzymes to the triphosphate, which competitively inhibits HSV DNA polymerase. Some investigators have found that the viral DNA polymerase activity is more sensitive to inhibition than that of cellular DNA polymerases, an observation that could explain some of the selective toxicity of the drug and its dose-related toxicity. Vidarabine triphosphate is incorporated into both cellular and viral DNA, where it may act as a chain terminator for newly synthesized HSV nucleic acid.

Despite its proven efficacy, Ara-A does suffer from a number of limitations, including low lipophilicity as evidenced by a negative log P (octanol/water), which results in a failure to be adequately transported across biological membranes.

Herpes simplex virus is a causative factor for encephalitis. Its involvement in the CNS represents the most common cause of nonepidemic fatal encephalitis in the United States. An estimated 1,000 to 5,000 cases occur each year in the U.S., with death in over one half of those who are untreated. Herpes simplex virus type 2 causes encephalitis in patients with thymic dyplasia and other severe immunodeficiency states. Encephalitis also is a common opportunistic infection associated with AIDS.

The acute severe encephalitis due to herpes simplex type 1 in humans may represent a primary infection, a reinfection or an activation of latent infection. The primary mode of viral transport into the CNS has not been clearly established. However, it has been shown that following extraneural inoculation, the virus gained access to the CNS by both hematogenous and neural pathways. The neural pathway of transport in man is supported by the fact that the virus can be isolated from explants of both trigeminal ganglia in the majority of routine autopsies.

Herpes simplex encephalitis is the most common cause of sporadic fatal encephalitis. Both the high mortality rate and the risk of severe sequelae in the survivor have prompted attempts at therapy with antiviral compounds. In order for the antiencephalitic agent to exert its effect, it is necessary for the drug to be present in the CNS where the virus is lodged, at an optimum concentration and for a sufficient period of time. Maintaining a therapeutic level of the drug over a prolonged period at the site of action is essential in optimal reduction of viral concentrations. Resistance of virus in the brain after treatment has been reported in almost all of the cases studied so far. Only very rarely has total remission been achieved.

The main reason for the lack of successful treatment is the inefficient method of drug delivery to the brain, the major impediment to drug delivery to the brain being the blood-brain barrier. Antiviral agents such as iododeoxyuridine and vidarabine exhibit little activity and high toxicity in the treatment of encephalitis. This is primarily due to their inability to cross the blood-brain barrier at optimum concentrations. In the case of other antivirals such as acyclovir, drug resistance has been observed. To overcome such problems, a new family of fluorinated nucleoside analogs has been synthesized. This family includes 1-(2'-deoxy-2'-fluoro-β-D-arabinofuranosyl) derivatives of 5-methyluracil (FMAU), 5-iodocytosine (FIAC) and 5-iodouracil (FIAU). FIAU is a metabolite of FIAC. These compounds have been shown to display significant antiviral activity against herpes viruses in vitro and in some in vivo experiments. The mechanism of antiviral activity depends in part on the phosphorylation of these agents by viral-specified thymidine kinase. These agents are rapidly taken up and phosphorylated only to the 5'-monophosphate in HSV-infected cells; the monophosphates are presumably further phosphorylated by cellular enzymes to the corresponding triphosphates. Phosphorylation of these agents by the virus-coded thymidine kinase is much better than by the cellular enzymes. These antiviral agents are incorporated into termini and internucleoside linkages of viral DNA much more than into the DNA of uninfected cells. Since maximum selectivity would improve the therapeutic potential of any new antiviral drug, relatively low toxicity with normal cells is mandatory. The low cytotoxicity exhibited by these agents with uninfected cells indicate selectivity of action.

Although these nucleoside analogs exhibit high selectivity toward viral cells, they are quite polar and therefore their ability to penetrate the BBB is greatly minimized. They must be administered in high doses to attain an effective level in the brain, resulting in severely toxic side-effects. For example, FMAU, considered the most potent antiviral agent of its class (therapeutic index greater than 3,000) in treating encephalitis, produces irreversible neurological damage at doses greater than 32 mg; other side effects include diarrhea, nausea and blood count depression. High doses of FIAU have resulted in cardiac fibrosis, myelosuppression and lymphoid depletion. In the case of FIAC and FMAU, significant reduction in body weight or death has also been noted at higher doses. Further, sustained therapeutic levels have not been achieved, even at these higher doses.

It is known that FIAC is metabolized extensively in vivo and that its metabolites retain their antiviral activity in cell culture. The major metabolites of FIAC include the deaminated species FIAU, the deiodinated species 2'-fluoroarbinosylcytosine (FAC) and 2'-fluoroarbinosyluracil (FAU) and their glucuronides. Two metabolites of FMAU have been isolated from the urine of mice. These include 2'-fluoro-5-hydroxymethylarabinosyluracil (FHMAU) and a glucuronide of FMAU. FMAU, FIAU and FIAC have been found to exhibit more potent antiviral activity than acyclovir. The metabolites of these compounds, even though potent inhibitors of HSV-2 in cell cultures, are essentially devoid of antiviral activity in vivo in the encephalitis model. This dichotomy between in vitro activity and in vivo activity suggests that these agents do not cross the BBB in sufficient concentration to exert activity.

(E)-5-(2-bromovinyl)deoxyuridine (BVDU) is also a polar antiviral agent effective against encephalitis caused by herpes zoster virus and HSV-1. This agent crosses the BBB in low levels only at very high concentrations; as a result, it has been shown to induce sister chromatid exchange. Other side-effects include toxicity to liver, bone marrow function and gonads.

Dihydroxypropoxymethylgaunine (DHPG) belongs to the same class of antiviral agents as acyclovir. However, DHPG has been shown to be at least 100-fold more effective than acyclovir in the treatment of encephalitis in vitro and in vivo. DHPG is more efficiently phosphorylated in infected cells than is acyclovir. As with acyclovir, herpes virus-specific thymidine kinase phosphorylates DHPG to its monophosphate, which is further phosphorylated to its di- and triphosphate by cellular guanylate kinase and other cellular enzymes, respectively. However, DHPG is transported to the brain only at high doses, which in turn produce high plasma levels of the drug which exert cytotoxic effects on normal human mycloid cells. Studies have shown that acyclovir crosses the BBB poorly, and at higher doses causes problems such as renal blockage.

Human cytomegalovirus (HCMV) is a virus of the herpes group which includes herpes simplex I and II, Epstein-Barr virus, and varicella zoster virus. In common with the other members of its group, infection with HCMV leads to a latent state in which the viral genome becomes incorporated in the host DNA, and in which recurrent infections are common. Vital infection with HCMV is quite widespread, with approximately 50% of Americans showing seropositivity by age 30. In the majority of cases the virus does not cause an overt disease state, but can be detected through serological and other laboratory procedures in otherwise healthy individuals. In the absence of complicating factors, exposure to the virus can result in a clinical presentation ranging from asymptomatic seroconversion to a disease state resembling infectious mononucleosis.

In contrast to viral infection in normal adults, HCMV in the fetus or neonate can result in severe clinical manifestations. The virus in these cases is acquired congenitally, often from asymptomatic mothers. The virus has been said to be the single most frequent cause of viral infections in newborns. The occurrence of HCMV in neonates is from 0.5% to 4% of all live births, but only 10% to 20% of these will have clinical manifestations of cytomegalic disease, which mainly involve the CNS and which can result in permanent, debilitating brain damage or auditory degeneration.

When the host immune system is suppressed, HCMV becomes a much more serious infective agent. In this state, a latent HCMV infection may recur, or a primary infection may be unusually severe. Immunosuppression can occur in several circumstances, for example, during use of immunosuppressive drugs, such as corticosteroids, azathioprine, and thymocyte immune globulin which are given to prevent rejection of a transplanted organ when a patient has undergone organ transplant surgery. Along with other complications, cytomegalic disease is a common and sometimes especially serious problem which can follow successful kidney, bone marrow, and heart transplantation. The manifestations of cytomegalic disease following transplant surgery can include, but are not limited to, retinitis and pneumonitis. Another particularly serious complication occurring during immunosuppressive therapy is Kaposi's sarcoma (KS). A strong correlation is known to exist between KS and HCMV, to the extent that it has been postulated that HCMV causes KS, analogously to the relationship between Epstein-Barr virus and Burkitt's lymphoma. However, a causal role for the virus has not been definitively established.

An immunosuppressed state is the hallmark of acquired immunodeficiency syndrome (AIDS), and HCMV has been shown to have an extraordinary prevalence in this population, approaching 94%. In addition, cytomegalic disease and its complications are among the primary causes of much of the suffering from AIDS as well as a major factor causing death. HCMV is known to result in a suppression of cell-mediated immunity through depression of levels of T-helper cells with an increase in suppressor/cytotoxic T-cells. Before the discovery of human immunodeficiency virus (HIV), the list of candidates for the cause of AIDS included HCMV. The consequences of HCMV infection in AIDS are manifold, with neural and especially ocular involvement being predominant. Ocular involvement is presented as a hemorrhagic retinitis, first evidenced by blurring of vision. This retinitis is so common that it has been proposed that it be the primary diagnostic evidence for the presence of AIDS. Neural involvement resulting in viral encephalitis is also common and presents itself post-mortem in the microglial nodules which are typical of HCMV infection. In AIDS, this neural involvement is concomitant with HIV infection of the CNS, often manifesting as subacute encephalopathy.

An antiviral agent which has shown promise in the treatment of HCMV infections in immunosuppressed states is DHPG. As mentioned above, DHPG is structurally similar to acyclovir (ACV), a safe and efficacious antiherpetic agent. The primary mechanism of DHPG action against CMV is inhibition of the replication of viral DNA by DHPG-triphosphate. This inhibition includes a selective and potent inhibition of the viral DNA polymerase. Since HCMV does not encode a virus-specific thymidine kinase, phosphorylation of DHPG is presumably accomplished by the host-cell enzymes, primarily various nucleoside kinases, which have been shown to be elevated in HCMV-infected cells. The markedly increased activity of DHPG toward CMV compared with ACV appears to be due in part to the efficient intracellular metabolism of DHPG to its mono and triphosphate in CMV-infected cells. The relative in vitro activities, as measured by the $IC_{50}$ values of DHPG vs ACV are of the same order against herpes simplex virus (HSV), namely 0.2 to 0.8 $\mu$M. However, against HCMV the $IC_{50}$ for DHPG is approximately 2.5 $\mu$M. Thus, DHPG has significant activity against HCMV in vitro. These promising results have been extended in animal models as well as in clinical trials.

As mentioned above, one of the rust clinical signs of AIDS infection is a retinitis which is caused by HCMV. One of the most dramatic recent clinical demonstrations of antiviral activity has been in a study of the effects of intravenous DHPG in AIDS patients who were suffering from progressive blindness caused by cytomegalic infection of the retina. In these patients, not only did viral liters drop to an unobservable level, but clinically observable improvement in sight was achieved. In other studies, significant improvement in other areas of cytomegalic infection was shown. These included improvement in the cytomegalic pneumonitis and encephalitis, as well as gastrointestinal infections.

DHPG, obviously, has very high intrinsic activity but, as with most useful drugs, has a number of inherent undesirable properties as well. Problems with the aqueous solubility of the compound (5.1 mg/mL at 37° C.) necessitate the use of the sodium salt for the intravenous administration of the drug. This induces pain or phlebitis at the infusion site, since the pH of the solution is about 11. In humans, oral bioavailability of DHPG is only 3–4.6% based on urinary excretion, with 99% of the drug being excreted unchanged by the kidneys. The pharmacokinetic disposition of intravenous DHPG in humans is similar to that observed in rats and dogs, with the finding of a biphasic elimination with an $\alpha$-phase half-life of 0.23 hours and a $\beta$-phase of 2.53 hours. These values are quite similar to those for acyclovir, and show that repeated dosing is necessary to maintain effective plasma concentration. Neutropenia is the most frequent dose-dependent toxicity associated with DHPG therapy.

DHPG is a hydroxymethyl analog of acyclovir and consequently is more polar and is expected to pass through the blood brain barrier (BBB) even less readily. In rodent models, it has been shown that acyclovir distributes into most organs, with the highest levels found in renal tissue and the lowest levels found in brain tissue. Pharmacokinetic studies of DHPG in the rat and dog have demonstrated behaviour similar to acyclovir. Human pharmacokinetics of intravenous DHPG indicate cerebrospinal fluid (CSF) concentrations equivalent to 24% to 67% of plasma concentrations. However, since CSF levels may reflect transport through the choroid plexus, some uncertainty regarding specific brain levels of DHPG exists. Regardless of the efficiency with which DHPG crosses the BBB, however, it is to be expected that it may leave the CNS by the same mechanism with equal facility. In view of the significant role played by CMV in AIDS patients with severe neurologic complications, and the possibility that CMV could create a reservoir of persistent infection of the CNS even if peripheral clearance were realized, there exists a rationale for identifying antiviral drugs that can penetrate the BBB and accumulate in the brain, thereby providing a sustained release of the antiviral to maintain a therapeutically effective concentration.

Acquired immune deficiency syndrome (AIDS) was first described as a distinct clinical entity in 1981. As of October 1989, 110,000 cases of AIDS, as defined by the Center for Disease Control (CDC), have been diagnosed and 65,000 people have died from the disease. This insidious and pernicious malady has a 2-3 year fatality rate of almost 100% and is expected to strike between 135,000 and 270,000 people by 1991 alone. AIDS is now the leading cause of premature mortality in a number of areas and in several subpopulations in the U.S.; by 1991, it is expected to be a major killer. In other areas of the world, a similarly grim picture is developing. In central Africa, where the AIDS pathogen evolved, the disease is endemic and in several locations the increase in incidence of infection exceeds 0.75% of the total population per year. AIDS is caused by a retrovirus related to the lentivirinae family and has been designated human immunodeficiency virus (HIV-1). This pathogen selectively infects lymphocytes bearing a T4 surface antigen. These helper/inducer T-cells are responsible for containing and eliminating various types of infection including those precipitated by *Pneumocystis carinii, Toxoplasma gondii, Cryptococcus neoformans, Candida albicans, Mycobacterium aviumintracellular* and others. The destruction of cellular immunity induced by HIV-1 causes the normally benign infections resulting from the above-mentioned pathogens to run more fulminate courses. These opportunistic infections are generally the causes of death in patients with AIDS.

Early in the course of the AIDS epidemic, clinicians noted that patients were depressed and initially this was attributed to a normal psychological response to learning that one had a terminal disease. Later, however, it was realized that cognitive impairment and dementia were associated with AIDS. These CNS-associated symptoms of AIDS are now well-recognized and affect 40% of all AIDS patients at some point in the course of the disease.

In AIDS, the CNS, like the periphery, is susceptible to opportunistic infections and unusual neoplasms. Several of these have been identified, including cerebral toxoplasmosis, cryptococcal infection, candidiasis, cerebral tuberculosis, progressive multifocal leukoencephalopathy, cytomegalovirus encephalitis and primary brain lymphomas. Interestingly, these occur in less than 30% of neurologically-impaired AIDS patients. In addition, symptoms caused by these pathogens are generally focal in nature and are expressed as seizures. In the majority of AIDS patients, neuropsychiatric changes are characterized as an insidious, progressive dementia related to diffuse parenchymal brain dysfunction. Early symptoms of this disease include impaired cognitive, motor and behavior functions, including the inability to concentrate, difficulty in recalling recent events, losing one's train of thought in midsentence and general mental slowing. Motor impairments include leg weakness and problems in proprioception. Behaviorally, victims become apathetic, withdrawn and distraught. Later symptoms include global cognitive dysfunction with psychomotor retardation. Victims are autistic, mute, lethargic and quietly confused. Patients manifest urinary and fecal incontinence and may be afflicted by painful peripheral neuropathies including burning sensations or numbness. Neurohistopathologically, the picture is even worse. While only 40% of AIDS patients are recognized as demonstrating brain dysfunction, 80–95% of the brains from AIDS patients are abnormal at autopsy. Gross changes include decreased brain weight and general cerebral atrophy. Histopathologically, several unique abnormalities are consistently seen in demented AIDS patients. Most of these are white matter changes and include a diffuse pallor, perivascular and parenchymal sites that contain lymphocytic and macrophage infiltrates and vacuolation. Other changes include the presence of microglial nodules whic infect both gray and white matter and bizarre giant multinucleated cells. The presence and number of these cells which contain HIV-1 virons give excellent correlation with the severity of the dementia. The agent responsible for subacute encephalitis, also known as AIDS encephalopathy, has been shown to be HIV-1. Several direct and indirect lines of evidence support this etiology.

This central infection will have a detrimental impact on possible therapies directed at AIDS. The CNS is protected by the BBB and is not drained by the lymphatic system, making it an excellent location for eluding the immune system. If, therefore, agents are found that reconstitute the immune system, peripheral manifestation of AIDS, including many opportunistic infections, can be cured but the central infection will persist. The result of this could be a physically healthy but severely demented individual. In addition, host-cell restriction, i.e. partial expression of the viral genome, may cause viral latency in the CNS for many years. Also, once proviral DNA is incorporated, the only hope of containing the disease is by preventing the spread of further cellular infection. This implies, based on active in vitro doses, that for antiviral therapies to be effective, agents must pass the BBB and achieve relatively high sustained levels in neural tissue. The neurotropic nature of HIV-1 and the fact that the brain probably acts as a viral reservoir makes implementing the preceding statement imperative. Of agents presently available, azidothymidine (also known as zidovudine or AZT) has been clinically shown to be the most useful in mitigating the effects of the AIDS virus. AZT inhibits retroviral transcriptase, the enzyme responsible for initiating viral replication.

AZT has been shown to improve the immunological picture in AIDS patients. In various clinical studies, T-cell lymphocytes (T4+) were shown to increase in number, opportunistic infections spontaneously disappeared, and patients gained weight due to increased appetite. Also, fever subsided and skin hypersensitivity returned. At high doses of AZT, viremia disappeared and T-cell function was restored. The bioavailability is about 60%. The drug is generally well-tolerated, but several untoward side effects occurred, including headache and abdominal discomfort. The most severe side effect was anemia, which proved to be dose-limiting in several cases. AZT has been used in large clinical trials, the results of which are very exciting. In a double blind study, 16 out of 137 died in the placebo group while only one patient out of 145 died in the AZT treatment group (250 mg/4 hrs). T4+ lymphocytes were higher in the treated group and fewer opportunistic infections occurred. As before, a reversible bone marrow depression resulting in granulocytopenia, thrombocytopenia, etc., was observed. Recently, dideoxyinosine has also been shown to be effective in reducing the cytopathicity and infectivity of HIV in vivo. The effect of AZT on the neurological manifestation of AIDS has been reported by Yarchoan et at, *Lancet,* i, 132 (1987). In a series of four case reports, AZT was shown to improve immunological and neurologic functioning. T4+ cells increased in number, motor symptoms improved, gait became less ataxic and muscle strength returned. Attention span increased in one case and verbal skills improved. Unfortunately, when the drug was stopped in cases of anemia, all improvements disappeared and mental function declined. This initial report indicated that AZT can at least partially reverse neurological dysfunction. The authors noted at the end of the paper that "even modest enhancement of BBB penetration might have very important clinical consequences".

These limited improvements in neurological symptomatology are consistent with the similarly limited ability of AZT to pass into the CSF. Unfortunately, CSF levels of a drug may be a poor indication of brain tissue levels. Several studies have shown that the correlation between CSF and parenchyma concentrations are not necessarily significant. In general, polar compounds such as AZT are the most deceptive in this respect. The reason for this is that if a hydrophilic compound is taken up primarily via an unprotected area like the choroid plexus, detectable concentrations may indeed reach the CSF but the compound may not partition into the lipoidal brain parenchyma and as a result may be restricted to the CSF. This would be manifested by apparently adequate AZT levels as measured by CSF sampling but inadequate levels in brain tissue where the drug is needed. This assumption has been borne out in a recent paper by Terasaki et al, *J. Inf. Dis.,* 158, 630 (1988). In it, the BBB penetration of AZT was shown to be very low, close to the uptake of sucrose, a vascular marker. The high concentrations of AZT found in CSF are presumably due to active transport of AZT at the choroid plexus via the thymidine pump. Again, these CSF levels represent AZT which is not in equilibrium with the brain interstitial fluid and therefore is not accessible to infected sites. It is clear that high levels of AZT are required to provide even marginal improvement in AIDS encephalopathy and that these doses are peripherally toxic.

The previous discussion has indicated that the AIDS virus is neurotropic and that the resulting brain infection by this pathogen is disastrous. Various agents have been identified which inhibit infection and abolish cytopathology in the AIDS virus. In some instances these compounds, like AZT, pass the BBB and achieve quantitative levels in CSF. Clinical results suggest, however, that high sustained drug levels, i.e. those that approach in vitro inhibitory concentrations, are required in the brain. Importantly, CSF levels do not reflect brain tissue concentration of AZT. Unfortunately, simply increasing the dose proportionally to achieve these ends increases blood concentrations and leads to various dose-related toxicities. Anemia has proved to be dose-limiting in many cases with AZT. Increasing brain levels of the nucleoside is possible by administering lipophilic esters of AZT leading to an increase in brain concentration of the nucleoside. These prodrugs are, however, not optimized in terms of pharmacokinetics and tissue distribution. Thus, while it is true that by increasing the lipophilicity of AZT, the drug will more easily pass the BBB and enter the CNS, the increased lipophilicity will increase the distribution of the compound in general, leading to an even greater tissue burden in all locations. This has ramifications in terms of peripheral toxicity such as anemia, i.e. a bad situation is made even worse. The other major drawback of simply increasing the lipophilicity of AZT is that while influx to the CNS is increased, the efflux is also greater, with the result being poor retention in the CNS and a therapeutically insufficient biological half-life. These two objections to simple antiviral prodrugs, namely: 1) increased tissue burden with little tissue specificity, and 2) poor CNS retention, point to the need for a more sophisticated approach, i.e. a chemical delivery system for brain-targeted drug delivery.

A dihydropyridine$\rightleftharpoons$pyridinium salt redox carrier system has recently been successfully applied to brain-targeted delivery of a variety of drug species. Generally speaking, according to that system, a dihydropyridine carrier moiety is covalently bonded to a biologically active compound, which derivative can enter the CNS through the blood-brain barrier following its systemic administration. Subsequent oxidation of the dihydropyridine species to the corresponding pyridinium salt leads to delivery of the drug to the brain.

More specifically, the redox carrier system provides for brain-targeted drug delivery by means of carrier-drugs, which in their reduced form, which is the form intended for administration, can be represented by the formula

[D-DHC]

wherein [D] is a centrally acting drug species and [DHC] is the reduced, biooxidizable, blood-brain barrier penetrating, lipoidal form of a dihydropyridine⇌pyridinium salt redox carrier. In their oxidized form, which is the form "locked" in the brain from which the active drug is ultimately released, the carrier-drugs can be represented by the formula

[D-QC]$^+$X$^-$ wherein X$^-$ is the anion of a non-toxic pharmaceutically acceptable acid, [D] is a centrally acting drug species and [QC]$^+$ is the hydrophilic, positively charged ionic pyridinium salt form of a dihydropyridine⇌pyridinium salt redox carrier.

Various aspects of the redox carrier system have been described in detail in Bodor U.S. Pat. No. 4,479,932, issued Oct. 30, 1984; Bodor U.S. Pat. No. 4,540,564, issued Sep. 10, 1985; Bodor et al U.S. Pat. No. 4,617,298, issued Oct. 14, 1986; UNIVERSITY OF FLORIDA's International Application No. PCT/US83/00725, published under International Publication No. WO83/03968 on Nov. 24, 1983; Bodor U.S. Pat. No. 4,727,079, issued Feb. 23, 1988; Bodor U.S. Pat. No. 4,824,850, issued Apr. 25, 1989; Bodor U.S. Pat. No. 4,829,070, issued May 9, 1989; Anderson et al U.S. Pat. No. 4,863,911, issued Sep. 5, 1989; Bodor U.S. Pat. No. 4,880,816, issued Nov. 14, 1989; Bodor U.S. Pat. No. 4,880,921, issued Nov. 14, 1989; Bodor U.S. Pat. No. 4,900,837, issued Feb. 13, 1990; UNIVERSITY OF FLORIDA's European Patent Application No. 88312016.4, published under European Publication No. 0327766 on Aug. 16, 1989; UNIVERSITY OF FLORIDA's European Patent Application No. 89302719.3, published under European Publication No. 0335545 on Oct. 4, 1989; and numerous related publications. Among the redox carrier-drugs provided by the earlier chemical delivery system are dihydropyridine/pyridinium salt derivatives of dopamine, testosterone, phenytoin, GABA, valproic acid, tyrosine, methicillin, oxacillin, benzylpenicillin, cloxacillin, dicloxacillin, desipramine, acyclovir, trifluorothymidine, zidovudine, hydroxy-CCNU, chlorambucil, tryptamine, dexamethasone, hydrocortisone, ethinyl estradiol, norethindrone, estradiol, ethisterone, norgestrel, estrone, estradiol 3-methyl ether, estradiol benzoate, norethynodrel, mestranol, indomethacin, naproxen, FENU, HENU, 5-FU and many others.

The dihydropyridine redox carrier system has achieved remarkable success in targeting drugs to the brain in laboratory tests. Unfortunately, the dihydropyridine-containing derivatives suffer from stability problems, since even in the dry state they are very sensitive to oxidation as well as to water addition. Such problems have significantly complicated attempts to commercialize the system. Thus, a different carrier approach to brain-targeted drug delivery which would not include the inherently unstable dihydropyridine system would be desirable.

A phosphonate derivative of the antiviral agent DHPG has been described previously by Prisbe et al, *J. Med. Chem.* 1986, 29, 671–675. That compound, in which a

is directly attached via to phosphorus-carbon bond to the antiviral drug, is structurally distinct from the phosphonate esters to which the present invention relates. Prisbe et al's phosphonate, unlike DHPG, was not active against herpes simplex virus types 1 and 2; however, it was reported to show moderate activity against HCMV in tissue culture.

SUMMARY OF THE INVENTION

The present invention provides novel phosphonate derivatives, adapted for targeted drug delivery, which have the formula

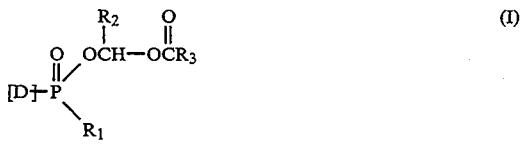

wherein [D] is the residue of a drug having a reactive functional group, said functional group being attached, directly or through a bridging group, via an oxygen-phosphorus bond to the phosphorus atom of the

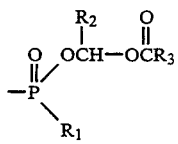

moiety; $R_1$ is $C_1$–$C_8$ alkyl, $C_6$–$C_{10}$ aryl or $C_7$–$C_{12}$ aralkyl; $R_2$ is hydrogen, $C_1$–$C_8$ alkyl, $C_6$–$C_{10}$ aryl, $C_4$–$C_9$ heteroaryl, $C_3$–$C_7$ cycloalkyl, $C_3$–$C_7$ cycloheteroalkyl or $C_7$–$C_{12}$ aralkyl; and $R_3$ is selected from the group consisting of $C_1$–$C_8$ alkyl; $C_2$–$C_8$ alkenyl having one or two double bonds; ($C_3$–$C_7$ cycloalkyl)—$C_rH_{2r}$— wherein r is zero, one, two or three, the cycloalkyl portion being unsubstituted or bearing 1 or 2 $C_1$–$C_4$ alkyl substituents on the ring portion; ($C_6$–$C_{10}$ aryloxy)$C_1$–$C_8$ alkyl; phenoxymethyl; 2-, 3- or 4-pyridyl; and phenyl—$C_rH_{2r}$— wherein r is zero, one, two or three and phenyl is unsubstituted or is substituted by 1 to 3 alkyl each having 1 to 4 carbon atoms, alkoxy having 1 to 4 carbon atoms, halo, trifluoromethyl, dialkylamino having 2 to 8 carbon atoms or alkanoylamino having 2 to 6 carbon atoms.

The invention further provides a generic method for target-enhanced delivery to the brain and other organs of a wide variety of drug species via the bidirectional transport of the drug species into and out of the organ by anionic sequestration via novel phosphonate derivatives.

DETAILED DESCRIPTION OF THE INVENTION

In a preferred aspect, the present invention provides novel phosphonate derivatives of hydroxy-containing drugs, which derivatives have the formula

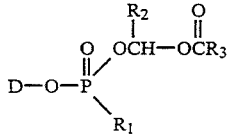
(Ia)

wherein D—O— is the residue of a drug having a reactive hydroxyl functional group, the oxygen atom of said functional group being bonded to the phosphorus atom of the

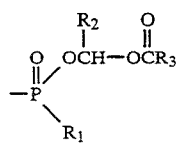

moiety, and wherein $R_1$, $R_2$ and $R_3$ are as defined with formula (I).

In another aspect, the present invention provides novel phosphonate derivatives of mercapto-containing drugs, which derivatives have the formula

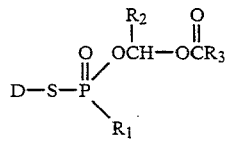
(Ib)

wherein D—S— is the residue of a drug having a reactive mercapto functional group, the sulfur atom of said functional group being bonded to the phosphorus atom of the

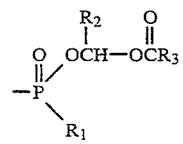

moiety, and wherein $R_1$, $R_2$ and $R_3$ are as defined with formula (I).

The present invention further provides novel phosphonate derivatives of carboxyl-containing drugs, which derivatives have the formula

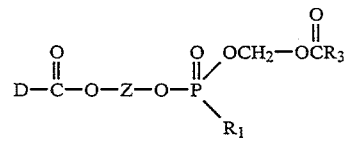
(Ic)

wherein

is the residue of a drug having a reactive carboxyl functional group, the carboxyl carbon atom of said functional group being linked, via an —O—Z—O— bridging group, to the phosphorus atom of the

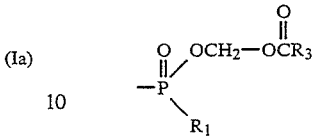

moiety; wherein Z is

wherein the alkylene group contains 1 to 3 carbon atoms and $R'_2$ is defined as is $R_2$ with formula (I); or wherein Z is $C_3$–$C_8$ cycloalkylene in which two adjacent ring carbon atoms are each bonded to a different oxygen atom in the —O—Z—O— bridging group; and wherein $R_1$ and $R_3$ are as defined with formula (I).

Still further, the invention provides novel phosphonate derivatives of drugs containing imide or amide functional groups, which derivatives have the formulas

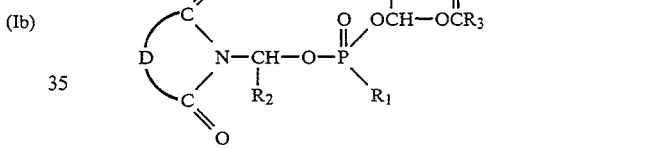
(Id)

and

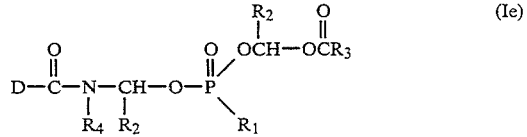
(Ie)

wherein

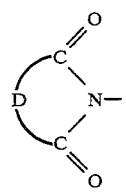

is the residue of a drug having a reactive imide functional group,

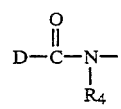

is the residue of a drug having a reactive amide functional group, the nitrogen atom of the imide or amide functional group being linked, via a

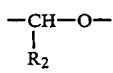

bridging group, to the phosphorus atom of the

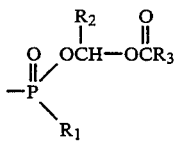

moiety; $R_4$ is preferably H but may also be $C_1$-$C_7$ alkyl or combined with

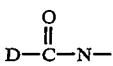

to form a cyclic amide; and wherein the $R_2$ groups in formulas (Id) and (Ie), which can be the same of different, are as defined with formula (I); and $R_1$ and $R_3$ are as defined with formula (I).

The present invention also provides novel phosphonate derivatives of amino-containing drugs, which derivatives have the formula

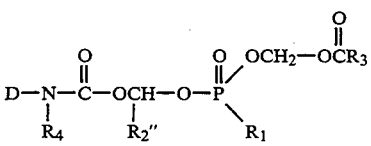 (If)

wherein

is the residue of a drug having a reactive primary amino ($R_4$=H) or secondary amino ($R_4$=other than H, but preferably $C_1$-$C_7$ alkyl or combined with D—N— to form a cyclic secondary amine) group, the nitrogen atom of the amino functional group being linked, via a

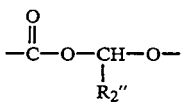

bridging group, to the phosphorus atom of the

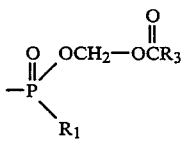

moiety; wherein $R''_2$ is defined as is $R_2$ with formula (I); and wherein $R_1$ and $R_3$ are as defined with formula (I). The identity of the $R_4$ group ($R_4$=other than H) in drugs having reactive secondary amino groups, while often $C_1$-$C_8$ lower alkyl, is immaterial to the invention, since $R_4$ is of course part of the drug residue itself and is left unchanged by the conversion to the formula (If) compound.

More particularly, in accord with the present invention, the following definitions are applicable:

The term "lipoidal" as used here is intended to mean lipid-soluble or lipophilic.

The term "drug" as used herein means any substance intended for use in the diagnosis, cure, mitigation, treatment or prevention of disease or in the enhancement of desirable physical or mental development and conditions in man or animal.

By "centrally acting" drug, drug species, active agent or compound as used herein, there is of course intended any drug species or the like, a significant (usually, principal) pharmacological activity of which is CNS and a result of direct action in the brain. Centrally acting drugs are preferred for derivation in accord with the present invention, brain-targeted drug delivery being the preferred goal of the invention.

The expression "drug having a reactive functional group" as used herein means that the drug possesses at least one functional group which is capable of covalently bonding to the phosphorus atom in the phosphonate moiety, either directly or through a bridging group, in such a manner that an active drug species will ultimately be released at the desired site of action, e.g. the brain. Such reactive functional groups include hydroxyl, carboxyl, mercapto, amino, amide and imide functions.

The word "hydroxyl" means an —OH function.
The word "carboxyl" means a —COOH function.
The word "mercapto" means an —SH function.
The word "amino" means a primary or secondary amino function, i.e. —NH$_2$ or —NHR$_4$. The secondary amino function is also represented herein as —NH—, particularly since the exact identity of the $R_4$ portion of —NHR$_4$ is immaterial, $R_4$ being a part of the drug residue itself which is left unchanged by conversion of the drug to the phosphonate carrier system.

The word "amide" means a carbamoyl (—CONH$_2$) or substituted carbamoyl (—CONHR$_4$) or a sulfamoyl (—SO$_2$NH$_2$) or substituted sulfamoyl (—SO$_2$NHR$_4$) functional group. The —CONHR$_4$ and —SO$_2$NHR$_4$ groups may also be represented herein as —CONH— and —SO$_2$NH—, respectively, since the identity of $R_4$ is immaterial, $R_4$ being a part of the drug residue itself which is left unchanged by conversion of the drug to the phosphonate carrier system.

The word "imide" means a functional group having the structure

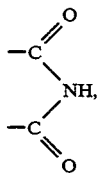

that is, the structure which characterizes imides (i.e. compounds having a succinimide-type or phthalimide-type structure).

It will be apparent from the known structures of the many drug species exemplified hereinbelow, that in many cases the selected drug will possess more than one reactive functional group, and, in particular, that the drug may contain hydroxyl or carboxyl or amino or other functional groups in addition to the groups to which the phosphonate carrier will be linked, and that these additional groups will at times benefit from being protected during synthesis and/or during administration. The nature of such protection is described in more detail hereinafter. Obviously, such protected drug species are encompassed by the definition of "drug" set forth hereinabove.

The expression "a bridging group" as used herein refers to a bivalent group used to attach the phosphonate carrier moiety to the drug when the drug does not contain a functional group susceptible to direct bonding to the phosphorus atom to form a linkage which will ultimately cleave to release an active drug species in the target organ. Drugs containing reactive hydroxyl and mercapto groups are capable of direct bonding to the phosphorus atom to form the desired linkage; other reactive functional group require appropriate bridging groups, for example as shown in structures (Ic), (Id), (Ie) and (If) hereinabove.

The term "$C_1$–$C_8$ alkyl" as used herein includes straight and branched-chain lower alkyl radicals having up to eight carbon atoms, e.g. methyl, ethyl, propyl, isopropyl, butyl, isobutyl, tert-butyl, pentyl, hexyl and the like.

The term "$C_6$–$C_{10}$ aryl" includes aromatic radicals having the indicated number of carbon atoms, e.g. phenyl and naphthyl.

The term "$C_7$–$C_{12}$ aralkyl" designates radicals of the type

-alkylene-aryl wherein the aryl portion is phenyl or naphthyl and the alkylene portion, which can be straight or branched, can contain up to 6 carbon atoms, e.g. methylene, ethylene, propylene, trimethylene, 1,2-butylene, 2,3-butylene, tetramethylene and the like. A typical aralkyl group is benzyl.

The term "$C_4$–$C_9$ heteroaryl" refers to aromatic radicals having the indicated number of carbon atoms and additionally containing 1 or 2 hetero atoms in the ring(s) selected from the group consisting of N, O and S. Illustrative radicals of this type include furyl, pyrrolyl, imidazolyl, pyridyl, indolyl, quinolyl and the like.

The term "$C_3$–$C_7$ cycloalkyl" designates sainted alicyclic hydrocarbon radicals containing the indicated number of carbon atoms, e.g. cyclopentyl and cyclohexyl.

The term "$C_3$–$C_7$ cycloheteroalkyl" refers to saturated alicyclic hydrocarbon radicals having the indicated number of carbon atoms and additionally containing 1 or 2 hereto atoms in the ring selected from the group consisting of N, O and S. Examples include morpholino, piperazinyl and pyrrolidinyl.

The term "$C_2$–$C_8$ alkenyl" designates unsaturated aliphatic hydrocarbon radicals, or olefinic groups, which contain one or two double bonds and the indicated number of carbon atoms, e.g. 1-propen-1-yl, 1,3-pentadien-1-yl and the like.

The term "($C_6$–$C_{10}$ aryloxy)$C_1$–$C_8$ alkyl" includes aryloxyalkyl radicals such as phenoxymethyl, i.e. the aryl portion contains 6 to 10 carbon atoms, e.g. phenyl or naphthyl, while the alkyl portion contains 1 to 8 carbon atoms, e.g. methyl or ethyl.

The term "$C_3$–$C_7$ cycloalkyl—$C_rH_{2r}$—" includes cycloalkyl and cycloalkyl-alkylene- radicals containing the indicated number of carbon atoms and bearing 0 to 2 $C_1$–$C_4$ alkyl groups as ring substituents. Illustrative radicals include cyclopentyl, cyclohexyl, cyclohexyl-methyl, 1-methylcyclohex-1-yl, 2,2,3,3-tetramethylcycloprop-1-yl and the like.

The term "phenyl—$C_rH_{2r}$—" includes phenyl and phenyl-alkylene-radicals containing the indicated number of carbon atoms, e.g. benzyl, any of which can bear 0 to 3 substituents as defined above. The substituents can be selected from $C_1$–$C_4$ alkyl, which can be straight or branched, e.g. methyl, ethyl, propyl, isopropyl; $C_1$–$C_4$ alkoxy, which can be straight or branched, e.g. methoxy, ethoxy; halo, which includes bromo, chloro, iodo and fluoro; trifluoromethyl; $C_2$–$C_8$ dialkylamino, e.g. dimethylamino and diethylamino; and $C_2$–$C_6$ alkanoylamino, e.g. acetamido and propionamido. Substituted phenyl—$C_rH_{2r}$— radicals include such radicals p-tolyl, 2,4,6-trimethylphenyl and m-trifluoromethylbenzyl.

The word "alkylene" when used in conjunction with the Z term herein refers to bivalent radicals of the type —$(CH_2)_n$— where n is 1, 2 or 3, and the corresponding branched-chain groups. When it is part of the Z term, the alkylene grouping can only be unsubstituted methylene if the drug residue is sufficiently hindered; otherwise, it should be substituted methylene or unsubstituted or substituted $C_2$–$C_3$ alkylene.

The term "$C_3$–$C_8$ cycloalkylene" as used in conjunction with the Z term designates radicals of the type

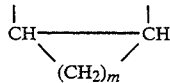

where m is 1 to 6 and the corresponding branched-chain groups.

The expression "non-toxic pharmaceutically acceptable salts" as used herein generally includes the non-toxic salts of compounds of formula (I) formed with non-toxic, pharmaceutically acceptable inorganic or organic acids. For example, the salts include those derived from inorganic acids such as hydrochloric, hydrobromic, sulfuric, sulfamic, phosphoric, nitric and the like; and the salts prepared from organic acids such as acetic, propionic, succinic, glucolic, stearic, lactic, malic, tartaric, citric, ascorbic, pamoic, maleic, hydroxymaleic, phenylacetic, glutamic, benzoic, salicyclic, sulfanilic, fumaric, methanesulfonic, toluenesulfonic and the like.

The expression "hydroxyl protecting group" as used herein is intended to designate a group (Y) which is inserted in place of a hydrogen atom of an OH group or groups in order to protect the OH group(s) during synthesis and/or to improve lipoidal characteristics and prevent premature metabolism of the OH group(s) prior to the compound's reaching the desired site in the body. The expression "protected hydroxy substituent" designates an OY group wherein Y is a "hydroxyl protecting group" as defined above.

Typical hydroxyl protecting groups contemplated by the present invention are acyl groups and carbonates. When the hydroxyl protecting group is acyl (i.e., when it is an organic radical derived from a carboxylic acid by removal of the hydroxyl group), it can be selected from the same group of radicals as those encompassed by the

portion of formula (I) hereinabove. Thus, the hydroxyl group preferably represents an acyl radical selected from the group consisting of alkanoyl having 2 to 8 carbon atoms; alkenoyl having one or two double bonds and 3 to 8 carbon atoms;

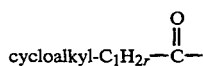

wherein the cycloalkyl portion contains 3 to 7 ring atoms and r is zero, one, two or three; phenoxyacetyl; pyridinecarbonyl; and

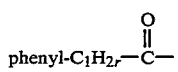

wherein r is zero, one, two or three and phenyl is unsubstituted or is substituted by 1 to 3 alkyl each having 1 to 4 carbon atoms, alkoxy having 1 to 4 carbon atoms, halo, trifluoromethyl, dialkylamino having 2 to 8 carbon atoms or alkanoylamino having 2 to 6 carbon atoms.

When the acyl group is alkanoyl, there are included both unbranched and branched alkanoyl, for example, acetyl, propionyl, butyryl, isobutyryl, valeryl, isovaleryl, 2-methylbutanoyl, pivalyl (pivaloyl), 3-methylpentanoyl, 3,3-dimethylbutanoyl, 2,2-dimethylpentanoyl, hexanoyl and the like. Pivalyl, isobutyryl, isovaleryl and hexanoyl are especially preferred, both as

groupings and as hydroxyl protective groups.

When the acyl group is alkenoyl, there are included, for example, crotonyl, 2,5-hexadienoyl and 3,6-octadienoyl.

When the acyl group is

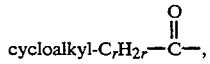

there are included cycloalkanecarbonyl and cycloalkanealkanoyl groups wherein the cycloalkane portion can optionally bear 1 or 2 alkyl groups as substituents, e.g. cyclopropanecarbonyl, 1-methylcyclopropanecarbonyl, cyclopropaneacetyl, α-methylcyclopropaneacetyl, 1-methylcyclopropaneacetyl, cyclopropanepropionyl, α-methylcyclopropanepropionyl, 2-isobutylcyclopropanepropionyl, cyclobutanecarbonyl, 3,3-dimethylcyclobutanecarbonyl, cyclobutaneacetyl, 2,2-dimethyl-3-ethylcyclobutaneacetyl, cyclopentanecarbonyl, cyclohexaneacetyl, cyclohexanecarbonyl, cycloheptanecarbonyl and cycloheptanepropionyl.

When the acyl group is pyridinecarbonyl, there are included picolinoyl (2-pyridinecarbonyl), nicotinoyl (3-pyridinecarbonyl) and isonicotinoyl (4-pyridinecarbonyl).

When the acyl group is

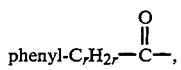

there are included, for example, benzoyl, phenylacetyl, α-phenylpropionyl, β-phenylpropionyl, p-toluyl, m-toluyl, o-toluyl, o-ethylbenzoyl, p-tert-butylbenzoyl, 3,4-dimethylbenzoyl, 2-methyl-4-ethylbenzoyl, 2,4,6-trimethylbenzoyl, m-methylphenylacetyl, p-isobutylphenylacetyl, β-(p-ethylphenyl)propionyl, p-anisoyl, m-anisoyl, o-anisoyl, m-isopropoxybenzoyl, p-methoxyphenylacetyl, m-isobutoxyphenylacetyl, m-diethylaminobenzoyl, 3-methoxy-4-ethoxybenzoyl, 3,4,5-trimethoxybenzoyl, p-dibutylaminobenzoyl, 3,4-diethoxyphenylacetyl, β-(3,4,5-trimethoxyphenyl)propionyl, o-iodobenzoyl, m-bromobenzoyl, p-chlorobenzoyl, p-fluorobenzoyl, 2-bromo-4-chlorobenzoyl, 2,4,6-trichlorobenzoyl, p-chlorophenylacetyl, α-(m-bromophenyl)propionyl, p-trifluoromethylbenzoyl, 2,4-di(trifluoromethyl)benzoyl, m-trifluoromethylphenylacetyl, β-(3-methyl-4-chlorophenyl)propionyl, p-dimethylaminobenzoyl, p-(N-methyl-N-ethylamino)benzoyl, o-acetamidobenzoyl, m-propionamidobenzoyl, 3-chloro-4-acetamidophenylacetyl, p-n-butoxybenzoyl, 2,4,6-triethoxybenzoyl, β-(p-trifluoromethylphenyl)propionyl, 2-methyl-4-methoxybenzoyl, p-acetamidophenylpropionyl, and 3-chloro-4-ethoxybenzoyl.

When the hydroxyl protecting group is a carbonate grouping, it has the structural formula

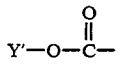

i.e., it is an organic radical which can be considered to be derived from a carbonic acid by removal of the hydroxyl group from the COOH portion. Y' preferably represents alkyl having 1 to 7 carbon atoms; alkenyl having one or two double bonds and 2 to 7 carbon atoms;

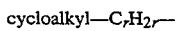

wherein the cycloalkyl portion contains 3 to 7 ring atoms and r is zero, one, two or three; phenoxy; 2-, 3-, or 4-pyridyl; or

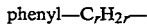

wherein r is zero, one, two or three and phenyl is unsubstituted or is substituted by 1 to 3 alkyl each having 1 to 4 carbon atoms, alkoxy having 1 to 4 carbon atoms, halo, trifluoromethyl, dialkylamino having 2 to 8 carbon atoms or alkanoylamino having 2 to 6 carbon atoms. Most preferably, Y' is $C_1$–$C_7$ alkyl, particularly ethyl or isopropyl.

Similarly, the expression "carboxyl protecting group" as used herein is intended to designate a group (W) which is inserted in place of a hydrogen atom of a COOH group or groups in order to protect the COOH group(s) during synthesis and/or to improve lipoidal characteristics and prevent premature metabolism of said COOH group or groups prior to the compound's reaching the desired site in the body. Typical of such carboxyl protecting groups W are the groups encompassed by Y' above, especially $C_1$–$C_7$ alkyl, particularly ethyl, isopropyl and t-butyl. While such simple alkyl esters and the like are often useful, other carboxyl protecting groups may be selected, e.g. in order to achieve greater control over the rate of in vivo hydrolysis of the ester back to the acid and thus enhance drug delivery. To that end, carboxyl protecting groups W such as the following may be used in place of the hydrogen of the —COOH group:

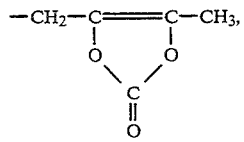

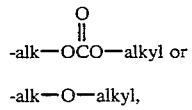
-alk—OCO—alkyl or

-alk—O—alkyl, wherein alk is $C_1$–$C_6$ straight or branched alkylene and the alkyl radical is straight or branched and contains 1 to 7 carbon atoms (e.g.

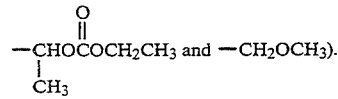

Other carboxyl protecting groups W which can be used in place of the hydrogen of the —COOH group and which are especially useful herein are the following:

$C_3$–$C_{12}$ cycloalkyl—$C_pH_{2p}$— wherein p is 0, 1, 2 or 3;

$C_6$–$C_{28}$ polycycloalkyl—$C_pH_{2p}$— wherein p is defined as above;

$C_6$–$C_{28}$ polycycloalkenyl—$C_pH_{2p}$— wherein p is defined as above;

$C_3$–$C_{12}$ cycloalkenyl—$C_pH_{2p}$— wherein p is defined as above;

—$CH_2$—$X_a$—$R_a$ wherein $X_a$ is S, SO or $SO_2$ and $R_a$ is $C_1$–$C_7$ alkyl or $C_3$–$C_{12}$ cycloalkyl;

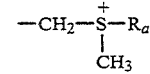

wherein $R_a$ is defined as above;

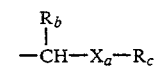

wherein $X_a$ is defined as above, $R_b$ is $C_1$–$C_7$ alkyl and $R_c$ is $C_1$–$C_7$ alkyl or wherein $R_b$ and $R_c$ taken together represent —$(CH_2)_{m'}$— wherein m' is 3 or 4 and —$(CH_2)_{m'}$— is optionally substituted by one to three $C_1$–$C_7$ alkyl;

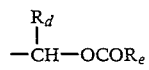

wherein $R_d$ is hydrogen or $C_1$–$C_7$ alkyl and $R_3$ is unsubstituted or substituted $C_1$–$C_{12}$ alkyl

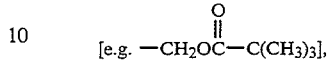

$C_3$–$C_{12}$ cycloalkyl —$C_pH_{2p}$— wherein p is defined as above, $C_3$–$C_{12}$ cycloalkenyl—$C_pH_{2p}$— wherein p is defined as above or $C_2$–$C_8$ alkenyl, the substituents being selected from the group consisting of halo, $C_1$–$C_7$ alkoxy, $C_1$–$C_7$ alkylthio, $C_1$–$C_7$ alkylsulfinyl, $C_1$–$C_7$ alkylsulfonyl,

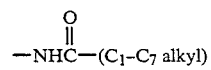

and

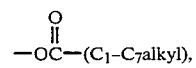

or $R_e$ is unsubstituted or substituted phenyl or benzyl, the substituents being selected from the group consisting of $C_1$–$C_7$ alkyl, $C_1$–$C_7$ alkoxy, halo, carbamoyl, $C_2$–$C_8$ alkoxycarbonyl, $C_2$–$C_8$ alkanoyloxy, $C_1$–$C_7$ haloalkyl, mono($C_1$–$C_7$ alkyl)amino, di($C_1$–$C_7$ alkyl)amino, mono($C_1$–$C_7$ alkyl)carbamoyl, di($C_1$–$C_7$ alkyl)carbamoyl, $C_1$–$C_7$ alkylthio, $C_1$–$C_7$ alkylsulfinyl and $C_1$–$C_7$ alkylsulfonyl, or $R_e$ is $C_6$–$C_{28}$ polycycloalkyl—$C_pH_{2p}$— or $C_6$–$C_{28}$ polycycloalkenyl—$C_pH_{2p}$— wherein p is defined as above;

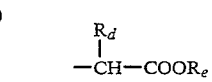

wherein $R_d$ and $R_e$ are defined as above; and

wherein $R_d$ is defined as above and $R_f$ and $R_g$, which can be the same or different, are each hydrogen, $C_1$–$C_7$ alkyl, $C_3$–$C_{12}$ cycloalkyl—$C_pH_{2p}$—, $C_3$–$C_{12}$ cycloalkenyl—$C_pH_{2p}$—, phenyl or benzyl, or one of $R_f$ and $R_g$ is hydrogen, $C_1$–$C_7$ alkyl, $C_3$–$C_{12}$ cycloalkyl—$C_pH_{2p}$—, $C_3$–$C_{12}$ cycloalkenyl—$C_pH_{2p}$—, phenyl or benzyl and the other of $R_f$ and $R_g$ is $C_6$–$C_{28}$ polycycloalkyl—$C_pH_{2p}$— or $C_6$–$C_{28}$ polycycloalkenyl—$C_pH_{2p}$—, or $R_f$ and $R_g$ are combined such that —$NR_fR_g$ represents the residue of a saturated monocyclic secondary amine.

When the carboxyl protecting group is $C_3$–$C_{12}$ cycloalkyl—$C_pH_{2p}$— or otherwise contains a $C_3$–$C_{12}$ cycloalkyl group, the cycloalkyl groups contain 3 to 8 ring atoms and may optionally bear one or more, preferably one to four, alkyl substituents. Exemplary such cycloalkyl groups are cyclopropyl, 2-methylcyclopropyl, 3-ethylcyclopropyl, 2-butylcyclopropyl, 3-pentylcyclopropyl, 2-hexylcyclopropyl, cyclobutyl, 2-methylcyclobutyl, 2,3-dimethylcyclobutyl, 3-butylcyclobutyl, 4-hexylcyclobutyl, 2,3,3-trimethylcyclobutyl, 3,3,4,4-tetramethylcyclobutyl, cyclopentyl, 2-methylcyclopentyl, 3-ethylcyclopentyl, 4-butylcyclopentyl, 5-methylcyclopentyl, 3-pentylcyclopentyl, 4-hexylcyclopentyl, 2,3-dimethylcyclopentyl, 2,2,5,5-tetmmethylcyclopentyl, 2,3,4-trimethylcyclopentyl, 2,4-dimethyl-3-ethylcyclopentyl, 2,2,3,4,4-pentamethylcyclopentyl, 2,3-dimethyl-3-propylcyclopentyl, cyclohexyl, 2,6-dimethylcyclohexyl, 3,3,5,5-tetramethylcyclohexyl, 2-methylcyclohexyl, 2-ethylcyclohexyl, 4-propylcyclohexyl, 5-butylcyclohexyl, 2,3-dimethylcyclohexyl, 2,4-dimethylcyclohexyl, 2,5-dimethylcyclohexyl, 2,3,4-trimethylcyclohexyl, 2,3-dimethyl-5-ethylcyclohexyl, 2,5-dimethyl-6-propylcyclohexyl, 2,4-dimethyl-3-butylcyclohexyl, 2,2,4,4-tetramethylcyclohexyl, 3,3,6,6-tetramethylcyclohexyl, 3,3,4,5,5-pentamethylcyclohexyl, 3,3,4,5,5,6-hexamethylcyclohexyl, 3,3,5-trimethyl-4-ethylcyclohexyl, 3,4,4-trimethyl-5-propylcyclohexyl, cycloheptyl, 3-methylcycloheptyl, 5-propylcycloheptyl, 6-butylcycloheptyl, 7-methylcycloheptyl, cyclooctyl, 2-methylcyclooctyl, 3-ethylcyclooctyl, 3,3,4-trimethylcyclooctyl, 3,3,5,5-tetramethylcyclooctyl and the like.

When the carboxyl protecting group is $C_3$-$C_{12}$ cycloalkenyl—$C_pH_{2p}$— or otherwise contains a $C_3$-$C_{12}$ cycloalkenyl group, the corresponding unsaturated radicals such as cyclopentenyl and cyclohexenyl and the like are contemplated.

The polycycloalkyl—$C_pH_{2p}$— radicals which can serve as carboxyl protecting groups, or as portions of carboxyl protecting groups, are bridged or fused saturated alicyclic hydrocarbon systems consisting of two or more rings, optionally bearing one or more alkyl substituents and having a total of 6 to 28 carbon atoms in the ring portion. The corresponding bridged or fused unsaturated alicyclic hydrocarbon systems are intended by the term "$C_6$-$C_{28}$ polycycloalkenyl—$C_pH_{2p}$—". Such polycycloalkyl and polycycloalkenyl radicals are exemplified by adamantyl (especially 1- or 2-adamantyl), adamantylmethyl (especially 1-adamantylmethyl), adamantylethyl (especially 1-adamantylethyl), bornyl, norbonyl, (e.g. exo-norbornyl or endo-norbornyl), norbornenyl (e.g. 5-norbornen-2-yl), norbornylmethyl (e.g. 2-norbornylmethyl) and norbornylethyl (e.g. 2-norbornylethyl), and by radicals of the type —$C_pH_{2p}$—(sterol residue)

wherein p is defined as above and the sterol residue is the portion of a steroidal alcohol which remains after removal of a hydrogen atom from a hydroxy group therein. The sterol residue is preferably that of a pharmacologically inactive steroid, e.g. cholesterol, a bile acid (cholic acid or related compound) or the like. In the case of polycyclic radicals, p is preferably 0, 1 or 2.

When the carboxyl protecting group is

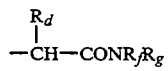

wherein —$NR_fR_g$ represents the residue of a saturated monocyclic secondary amine, such monocycles preferably have 5 to 7 ring atoms optionally containing another hetero atom (—O—, —S— or —N—) in addition to the indicated nitrogen atom, and optionally bear one or more substituents such as phenyl, benzyl and methyl. Illustrative of residues of saturated monocyclic secondary amines which are encompassed by the —$NR_fR_g$ term are morpholino, 1-pyrrolidinyl, 4-benzyl-1-piperazinyl, perhydro-1,2,4-oxathiazin-4-yl, 1- or 4-piperazinyl, 4-methyl-1-piperazinyl, piperidino, hexamethyleneimino, 4-phenylpiperidino, 2-methyl-1-pyrazolidinyl, 1- or 2-pyrazolidinyl, 3-methyl-1-imidazolidinyl, 1- or 3-imidazolidinyl, 4-benzylpiperidino and 4-phenyl-1-piperazinyl.

As yet another alternative, the carboxyl group can be protected by converting it to an amide, i.e. the —COOH group is converted to a —$CONR_fR_g$ group wherein $R_f$ and $R_g$ are as defined and exemplified above. Such amide groups are also intended to be encompassed by the expression "carboxyl protecting group" as used herein.

Selection of an appropriate carboxyl protecting group will depend upon the reason for protection and the ultimate use of the protected product. For example, if the protecting group is intended to be present in a pharmaceutically useful end product, it will be selected from those protecting groups described hereinabove which offer low toxicity and the desired degree of lipophilicity and rate of in vivo cleavage. On the other hand, if the protecting group is used solely for protection during synthesis, then only the usual synthetic requirements will generally apply.

The expression "amino protecting group" as used herein is intended to designate a group (T) which is inserted in place of a hydrogen atom of an amino group or groups in order to protect the amino group(s) during synthesis and/or to improve lipoidal characteristics and prevent premature metabolism of said amino group or groups prior to the compound's reaching the desired site in the body.

As with the carboxyl protecting groups, selection of a suitable amino protecting group will depend upon the reason for protection and the ultimate use of the protected product. When the protecting group is used solely for protection during synthesis, then a conventional amino protecting group may be employed. When the amino protecting group is intended to be present in a pharmaceutically useful end product, then it will be selected from among amino protecting groups which offer low toxicity and the desired degree of lipophilicity and rate of in vivo cleavage. Especially suitable for in vivo use as amino protecting groups T are activated carbamates, i.e. the protecting group T has the structure

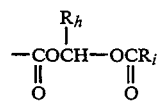

wherein $R_h$ is hydrogen, $C_1$-$C_7$ alkyl or phenyl and $R_i$ can be selected from the groups indicated as suitable carboxyl protecting groups W hereinabove. Again, the builder groups are preferred for use in vivo, and $R_i$ is preferably a polycycloalkyl or polycycloalkenyl-containing group, such as adamantyl or a sterol residue, especially a cholesterol or bile acid residue.

The drugs which can be derivatized in accord with the present invention must contain at least one functional group capable of bonding to the phosphorus atom in the phosphonate carrier moiety, directly or through a bridging group. Drugs which are capable of direct bonding are generally preferred because directly-bonded derivatives are more readily synthesized and their in vivo cleavage to the active drug species is likewise less complex. When a linking or bridging group is required, such must be chosen judiciously so that in vivo cleavage will occur in the desired sequence. The phosphonate derivatives of formula (I) are designed to be cleaved in vivo in stages after they have reached the desired site of action. The first cleavage, by esterase, provides a negatively-charged "locked-in" intermediate of the type

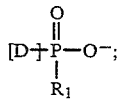

cleavage of the terminal ester grouping in (I) thus affords an inherently unstable intermediate of the type

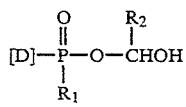

which immediately and spontaneously releases $R_2CHO$ and the negatively charged "locked in" intermediate depicted above. With time, a second cleavage occurs; this cleavage is catalyzed by means of alkaline phosphatase, releasing the original drug (D—OH in the case of hydroxy-linked drugs, D—SH in the case of mercapto-linked drugs or, in the case of other drug classes, a drug-bridging group entity which will readily release the original drug), along with $R_1PO^{2-}{}_3$. In the selected instances in which the drug is of the nucleoside type, such as is the case of zidovudine and numerous other antiretroviral agents, it is known that the drug is activated in vivo by phosphorylation; such activation may occur in the present system by enzymatic conversion of the "locked-in" intermediate with phosphokinase to the active phosphonate diphosphate and/or by phosphorylation of the drug itself after its release from the "locked-in" intermediate as described above. In either case, the original nucleoside-type drug will be convened, via the derivatives of this invention, to the active phosphorylated species according to the sequence:

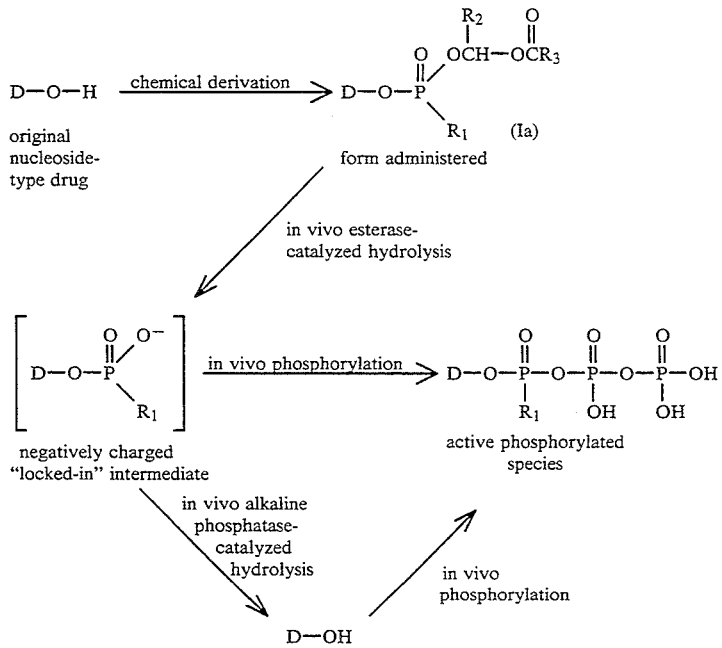

It is apparent from the foregoing that, in the case of nucleoside-type drugs which are activated by phosphorylation, the instant invention provides derivatives which need only a two-step in vivo phosphorylation to arrive at the active tri-phosphorylated species, while the original drug requires a three-step activation in vivo to the triphosphate.

In the case of drugs having a reactive hydroxyl or mercapto function directly bonded to the phosphorus atom, the cleavage to form the negatively charged "locked-in" intermediates is much faster than the cleavage of the drug itself from the remainder of the negatively charged intermediate, no matter what the identity of the

grouping in formula (Ia) or (Ib). The same is true for the case of imide-type and amide-type drugs. Thus, $R_2$ in structures (Id) and (Ie), like $R_2$ in structures (Ia) and (Ib), can be any of the groups defined as $R_2$ values with formula (I) hereinabove. The derivatives of formulas (Id) and (Ie), like those of formulas (Ia) and (Ib), are thus first cleaved by esterase to give the negatively charged intermediate; subsequent cleavage by alkaline phosphatase in the case of the amides and imides gives an unstable intermediate which rapidly is transformed into the original drug. On the other hand, in the case of drugs linked via amine or carboxylic acid functions, the identity of the $R_2$ groups must be carefully controlled so that the enzymatic cleavages occur in the proper order. It is apparent from a study of structures (Ic) and (If) hereinabove, that each of these structures contains more than one bond susceptible to cleavage by esterase; if these esterase-cleavable bonds do not cleave in the proper sequence, i.e. if the bond linking

to the rest of the molecule does not cleave before the carboxyl bond linking the drug to the phosphonate moiety, then the negatively charged "locked-in" intermediate will not be formed and targeted drug delivery will not occur. By utilizing an —OCH₂— linkage for

in formulae (Ic) and (If), that linkage becomes particularly susceptible to esterase. Nevertheless, judicious selection of the —O—Z— linkage in formula (Ic) and the

linkage in formula (If) is required. For example, when the drug residue is sterically hindered, —O—Z— can be —OCH₂— in formula (Ic), because that bond will be less susceptible to esterase than the bond linking

to the rest of the molecule, due to steric considerations. Likewise,

can be —OCH₂— in formula (If) when the drug residue is hindered. On the other hand, when structurally simple drugs which are not bulky/sterically hindered are derivatized, it may be required that —O—Z— cannot be —OCH₂— in formula (Ic) and

cannot be —OCH₂— in formula (If). In this way, the compounds are designed so that the bonds will cleave in the proper sequence.

From the foregoing, it will be apparent that many different drugs can be derivatized in accord with the present invention. Numerous such drugs are specifically mentioned hereinbelow. However, it should be understood that the following discussion of drug families and their specific members for derivatization according to this invention is not intended to be exhaustive, but merely illustrative.

Drugs containing a reactive hydroxyl or mercapto function for use herein include, but are not limited to, steroid sex hormones, antivirals, tranquilizers, anticonvulsants, antineoplastics (anticancer/antitumor agents), hypotensives, antidepressants, narcotic analgesics, narcotic antagonists and agonist/antagonists, CNS anticholinergics, stimulants, anesthetics, antiinflammatory steroids, nonsteroidal antiinflammatory agents/analgesics, antibiotics and CNS prostaglandins. Preferred drugs of this type are antivirals, antineoplastics and steroids.

More specifically, among the steroid sex hormones there are included: male sex hormones/androgens such as testosterone and methyl testosterone; and female sex hormones, including estrogens, both semisynthetic and natural, such as mestranol, quinestrol, ethinyl estradiol, estradiol, estrone, estriol, estradiol 3-methyl ether and estradiol benzoate, as well as progestins, such as norgestrel, norethindrone, ethisterone, dimethisterone, allylestrenol, cingestol, ethynerone, lynestrenol, norgesterone, norvinisterone, ethynodiol, oxogestone, tigestol and norethynodrel. Typically, the phosphonate moiety will be bonded to the steroid via a hydroxyl in the 3- or 17-position, with the 17-position being generally preferred.

Among the antivirals, there are included those of the nucleoside type, glycosides, phenyl glucoside derivatives and others. Those of the nucleoside type (i.e. a purine or pyrimidine base-type structure, including analogs of purines and pyrimidines, bearing a singly or multiply hydroxylated substituent, which may be a natural or unnatural sugar, hydroxy-bearing alkyl group or similar substituent) are preferred. Exemplary nucleoside-type antivirals include zidovudine (AZT; azidothymidine), ribavirin, (S)-9-(2,3-dihydroxypropyl)adenine, 6-azauridine, acyclovir (ACV), 5,6-dichloro-1-β-D-ribofuranosylbenzimidazole, 5,7-dimethyl-2-β-D-ribofuranosyl-s-triazole (1,5-a) pyrimidine, 3-deazauridine, 3-deazaguanosine, DHPG (ganciclovir), 6-azauridine, idoxuridine, dideoxycytidine (DDC), trifluridine (trifluorothymidine), dideoxyinosine, dideoxydehydrothymidine, dideoxyadenosine, BVDU, FIAU, FMAU, FIAC, Ara-T, FEAU, cyclaradine, 6-deoxyacyclovir, 3-deazaaristeromycin, neplanocin A, buciclovir (DHBG), selenazofurin, 3-deazaadenosine, cytarabine (cytosine arabinoside; Ara-C), 5-FUDR, vidarabine (Ara-A), tiazofurin, 3'-fluoro-2',3'-dideoxythymidine (FddThd), 1-(2,3-dideoxy-β-D-glyceropent-2-enofuranosyl)thymine (D4T or d4T), 3'-fluoro-2',3'-dideoxy-5-chlorouridine (FddClUrd), 5-(2-chloroethyl)-2'-deoxyuridine (CEDU), 5-ethyl-2'-deoxyuridine (EDU), 5-( 1-hydroxy-2-chloroethyl)-2'-deoxyuridine, 5-(1-methoxy-2-bromoethyl)-2'-deoxyuridine 5-(1-hydroxy-2-bromo-2-(ethoxycarbonyl)ethyl)-2'-deoxyuridine, 5-( 1-hydroxy-2-iodo-2-(ethoxycarbonyl)ethyl)-2'-deoxyuridine, 3'-azido-2',3'-dideoxyuridine (AZU), 3'-azido-2',3'-dideoxy-5-bromouridine, 3'-azido-2',3'-dideoxy-5-iodouridine; 3'-azido-2',3'-dideoxy-5-methylcytidine and 3'-fluoro-2',3'-dideoxyuridine (FddUrd). These and numerous other nucleoside-type antivirals suitable for derivatization in accord with the present invention have been described in the literature. See, for example, Van Aerschot et al, *J. Med. Chem.* 1989, 32, 1743–1749; Mansuri et al, *J. Med. Chem.* 1989, 32, 461–466; Kumar et al, *J. Med. Chem.* 1989, 32, 941–944; Lin et al, *J. Med. Chem.* 1989, 32, 1891–1895; Kim et al, *J. Med. Chem.* 1987, 30, 862–866; Lin et at, *J. Med. Chem.* 1987, 30, 440–444; Herdewijn et al, *J. Med. Chem.* 1988, 31, 2040–2048; Turk et al, *Antimicrobial Agents and Chemotherapy,* April 1987, Vol. 31, No. 4, 544–550; Elion, in *Topics in Medicinal Chemistry, 4th SCI-RSC Medicinal Chemistry Symposium,* ed. P. R. Leeming, Royal Society of Chemistry, London, 1988, pp. 163–171; Roberts et al, in *Topics in Medicinal Chemistry, 4th SCI-RSC Medicinal Chemistry Symposium,* ed. P. R. Leeming, Royal Society of Chemistry, London, 1988, pp. 172–188; Kelley, in *Topics in Medicinal Chem-* istry, 4th SCI-RSC Medicinal Chemistry Symposium, ed. P. R. Leeming, Royal Society of Chemistry, London, 1988, pp. 189–212; Harnden et al, in *Topics in Medicinal Chemistry, 4th SCI-RSC Medicinal Chemistry Symposium*, ed. P. R. Leeming, Royal Society of Chemistry, London, 1988, pp. 213–244; Reist et al, in *Nucleotide Analogues as Antiviral Agents*, ACS Symposium Series 401, ed. John C. Martin, American Chemical Society, Washington, D.C., 1988, Chapter 2, pp. 17–34; DeClercq, in *Approaches to Antiviral Agents*, ed. Michael R. Harnden, VCH, Great Britain, 1985, Chapter 3, pp. 57–99; Holy, in *Approaches to Antiviral Agents*, ed. Michael R. Harnden, VCH, Great Britain, 1985, Chapter 4, pp. 101–134; and Hovi, in *Antiviral Agents: The Development and Assessment of Antiviral Chemotherapy*, Volume I, ed. Hugh J. Field, CRC Press, Inc., Boca Raton, Fla., 1988, Chapter 1, pp. 1–21; all of which are incorporated by reference herein in their entirety and relied upon. Typically, the phosphonate moiety will be bonded to the nucleoside-type antiviral via a primary hydroxyl in the 5'-position or corresponding position when the antiviral does not have a 5'-hydroxyl. Nonnucleoside antivirals for possible derivatization herein include hydroxy-containing glycosides such as 2-deoxy-D-glucose and 2-deoxy-2-fluoro-D-mannose, phenyl glucosides such as phenyl-6-chloro-6-deoxy-$\beta$-D-glucopyranoside and benzimidazole analog type antivirals such as the syn and anti isomers of 6[[(hydroxyimino)phenyl]methyl]-1-[(1-methylethyl)sulfonyl]-1H-benzimidazol-2-amine.

Among the tranquilizers for derivatization herein, there can be mentioned hydroxy-containing benzodiazepine tranquilizers, for example oxazepam, lorazepam and temazepam; tranquilizers of the butyrophenone group, such as haloperidol; tranquilizers of the diphenylmethane group, for example hydroxyzine; phenothiazine-type tranquilizers, for example acetophenazine, carphenazine, fluphenazine, perphenazine and piperacetazine; and tranquilizer analogs of phenothiazines, e.g. clopenthixol.

Among the hydroxy-containing anticonvulsants, there can be mentioned, for example, the metabolites of valproic acid, i.e. 5-hydroxy-2-n-propylpentanoic acid, 4-hydroxy-2-n-propylpentanoic acid and 3-hydroxy-2-n-propylpentanoic acid.

Among the antineoplastics, i.e. anticancer and/or antitumor agents, there can be mentioned as illustrative urea derivatives, hormonal antineoplastics, podophyllotoxins (e.g. teniposide, etoposide), antibiotic-type antibiotics, nitrosourea-type alkylating agents and, especially, purine and pyrimidine antagonists. The purine and pyrimidine antagonist-type antineoplastics include simple purine and pyrimidine base-type structures, e.g. thioguanine and 6-mercaptopurine, as well as those of the nucleoside-type, e.g. Ara-AC, pentostatin, dihydro-5-azacytidine, tiazofurin, sangivamycin, Ara-A (vidarabine), 6-MMPR, 5-FUDR (floxuridine), cytarabine (Ara-C; cytosine arabinoside), 5-azacytidine (azacitidine), uridine, thymidine, idoxuridine, 3-deazauridine, cyclocytidine, dihydro-5-azacytidine, triciribine and fludrabine. Many nucleoside-type compounds have utility both as antineoplastics and as antiviral agents. Such are typically derivatized as described hereinabove with reference to the nucleoside-type antivirals.

Among the anesthetics, there can be mentioned pentothal (thiopental).

Among the antibiotics, there can be mentioned lincomycin type antibiotics such as clindamycin and lincomycin.

Among the narcotic analgesics, there can be mentioned those of the meperidine type such as meptazinol, profadol and myfadol; and those which can be considered morphine derivatives. The morphine derivatives include those of the morphine series, such as hydromorphone, oxymorphone, apomorphine, levorphanol, morphine and metopon; those of the benzomorphan series, such as pentazocine, cyclazocine and phenazocine; and those of the codeine series, such as codeine, oxycodone, drocode and pholcodine.

The narcotic antagonists and mixed agonist/antagonists include such compounds as nalbuphine, naloxone, nalorphine, buprenorphine, butorphanol, levallorphan, naltrexone, nalmefene, alazocine, oxilorphan and nalmexone.

The antiinflammatory steroids include such compounds as cortisone, hydrocortisone, betamethasone, dexamethasone, flumethasone, fluprednisolone, methyl prednisolone, meprednisone, prednisolone, prednisone, triamcinolone, triamcinolone acetonide, cortodoxone, fludrocortisone, flurandrenolone acetonide (flurandrenolide) and paramethasone.

Among the nonsteroidal antiinflammatory agents/non-narcotic analgesics, there can be mentioned, for example, clonixeril, sermatacin and naproxol.

Drugs containing a reactive amide or imide function for derivatization herein include, but are not limited to, tranquilizers, sedatives, anticonvulsants/antiepileptics, hypnotics, antineoplastics, antivirals, antibiotics/antibacterial agents, barbiturate antagonists, stimulants, antihypertensives and antidepressant/psychotropic drugs.

More specifically, there can be mentioned hydantoin-type tranquilizers and anticonvulsants/antiepileptics, for example, phenytoin, mephenytoin and ethotoin; barbiturate sedatives/anticonvulsants/antiepileptics, e.g. phenobarbital, amobarbital and butalbital; glutarimide or piperidine derivatives which are sedatives and hypnotics, for example, glutethimide, methyprylon and aminoglutethimide (also an anticonvulsant); benzodiazepine-type tranquilizers, such as nitrazepam, bromazepam, demoxepam, oxazepam; antidepressants/psychotropics, e.g. sulpiride; GABAergic agents/antiepileptics, for example progabide; valproic acid derivative-type anticonvulsants, e.g. valpromide; barbiturate antagonists, for example, bemegride; tetracycline-type antibiotics, such as demeclocycline, oxytetracycline, chlortetracycline, tetracycline, methacycline, minocycline and doxycycline; nonsteroidal antiinflammatory/analgesic agents, e.g. tesicam; and antineoplastics, for example alkylating agents of the nitrogen mustard-type, e.g. uracil mustard, spiromustine and cyclophosphamide, alkylating agents of the nitrosourea type such as PCNU, purine/pyrimidine antagonists, e.g. 5-FU(5-fluorouracil), and various other antineoplastics, such as razoxane and ICRF-187.

Drugs containing a reactive carboxyl function for derivatization in accord with the present invention include, but are not limited to, anticonvulsants, antineoplastics, antibiotics/antibacterials, diagnostics and nonsteroidal antiinflammatory agents/non-narcotic analgesics.

More specifically, there can be mentioned anticonvulsants, e.g. valproic acid; antineoplastics, for example, nitrogen mustard-type alkylating agents such as chlorambucil and folio acid antagonists such as methotrexate and dichloromethotrexate; penicillin-type antibiotics such as amoxicillin, phenoxymethylpenicillin (penicillin V), benzylpenicillin, dicloxacillin, carbenicillin, oxacillin, cloxacillin, hetacillin, methicillin, nafcillin, ticarcillin and epicillin; cephalosporin-type antibiotics, e.g. cephalothin, cefoxitin, cefazolin and cephapirin; miscellaneous other antibiotics, e.g. oxolinic acid; nonsteroidal antiinflammatories/non-narcotic analgesics, including propionic, acetic, fenamic and biphenylcarboxylic acid derivatives, for example, ibuprofen, naproxen, flurbiprofen, zomepirac, sulindac, indomethacin, ketoprofen, fenbufen, fenoprofen, indoproxen, fluprofen, bucloxic acid, tolmetin, alclofenac, fenclozic acid, ibufenac, flufenisal, pirprofen, flufenamic acid, mefenamic acid, clonixin, meclofenamic acid, flunixin, diclofenac, carprofen, etodolac, fendosal, prodolic acid, diflunisal and flutiazin; and diagnostics such as diohippuric acid and iothalamic acid.

Drugs containing a reactive amino function for use in accord with the present invention include, but are not limited to, GABAergics/antiepileptics, antineoplastics, cerebral stimulants, appetite suppressants, MAO inhibitors, tricyclic antidepressants, decongestants, narcotic analgesics, antivirals, neurotransmitters, small peptides, dopaminergic agents and antibiotics. Illustrative drugs of this structural type include antiepileptics such as GABA, γ-vinyl GABA and γ-acetylenic GABA; nitrogen mustard-type antineoplastics such as melphalan; antibiotic-type antineoplastics, e.g. daunorubicin (daunomycin), doxorubicin (adriamycin), dactinomycin and mitomycin C; nitrosourea-type antineoplastics such as alanosine; miscellaneous other antineoplastics, e.g. bactobolin, DON and acivicin; sympathetic stimulants/appetite suppressants, such as methamphetamine, phentermine, phenmatrazine, dextroamphetamine, levamphetamine, amphetamine, phenethylamine, methyl phenidate, aletamine, cypenamine, fencamfamin and etryptamine; MAO inhibitors, e.g. tranylcypromine; tricyclic antidepressants, e.g. protriptyline, desipramine, nortriptyline, octriptyline and maprotiline; cerebral stimulants, e.g. amedalin, bupropion, cartazolate, daledalin, difluanine and nisoxetine; antivirals such as glucosamine, 6-amino-6-deoxy-D-glucose, amantadine and rimantadine; amino acids/neutrotransmitters, e.g. tryptophan; small peptides, typically containing 2–20 amino acid units, e.g. the enkephalins (leu$^5$-enkephalin, met$^5$-enkephalin), endorphins and LHRH analogs; catecholamine neurotransmitters, e.g. norepinephrine, epinephrine and dopamine; other neurotransmitters, e.g. serotonin, and related compounds such as tryptamine; penicillin-type antibiotics such as ampicillin; cephalosporin-type antibiotics, e.g. cephalexin; and sympatholytic agents such as guanethidine and debrisoquin.

Also illustrative of the centrally acting drug species contemplated by this invention are pharmacologically active metabolites of drugs. Such metabolites are typified by hydroxylated metabolites of tricyclic antidepressants, such as the E- and Z-isomers of 10-hydroxynortriptyline, 2-hydroxyimipramine, 2-hydroxydesipramine and 8-hydroxychloripramine; hydroxylated metabolites of phenothiazine tranquilizers, e.g. 7-hydroxychlorpromazine; and desmethyl metabolites of N-methyl benzodiazepine tranquilizers, e.g. desmethyldiazepam. Other active metabolites for use herein will be apparent to those skilled in the art, e.g. SL 75102, which is an active metabolite of progabide, a GABA agonist, and hydroxy-CCNU, which is an active metabolite of CCNU, an anticancer nitrosourea. Typically, these pharmacologically active metabolites have been identified as such in the scientific literature but have not been administered as drugs themselves. In many cases, the active metabolites are believed to be comparable in activity to their parent drugs; frequently, however, the metabolites have not been administered per se because they are not themselves able to penetrate biological membranes such as the blood-brain barrier.

Diagnostic agents, including radiopharmaceuticals, are encompassed by the expression "drug" or the like as used herein. Any diagnostic agent which can be derivatized to afford a phosphonate derivative of formula (I) which will penetrate biological membranes, e.g. the BBB, and concentrate in the target organ, e.g. the brain, in its negatively charged form and can be detected therein is encompassed by this invention. The diagnostic may be "cold" and be detected by X-ray (e.g. radiopaque agents) or other means such as mass spectrophotometry, NMR or other non-invasive techniques (e.g. when the compound includes stable isotopes such as C13, N15, O18, S33 and S34). The diagnostic alternatively may be "hot", i.e. radiolabelled, such as with radioactive iodine (I 123, I 125, I 131) and detected/imaged by radiation detection/imaging means. Typical "cold" diagnostics for derivation herein include o-iodohippuric acid, iothalamic acid, iopydol, iodamide and iopanoic acid. Typical radiolabelled diagnostics include diohippuric acid (I 125, I 131), diotyrosine (I 125, I 131), o-iodohippuric acid (I 131 ), iothalamic acid (I 125, I 131), thyroxine (I 125, I 131), iotyrosine (I 131) and iodometaraminol (I 123). In the case of diagnostics, unlike the case of drugs which are for the treatment of disease, the "locked-in" negatively charged form will be the form that is imaged or otherwise detected, not the original diagnostic itself. Moreover, any of the drugs disclosed herein which are intended for the treatment or prevention of medical disorders but which can be radiolabelled, e.g. with a radioisotope such as iodine, or labelled with a stable isotope, can thus be converted to a diagnostic for incorporation into the phosphonate of formula (I).

When the drug selected for derivatization according to the present invention is to be linked to the phosphonate moiety via a secondary or tertiary hydroxyl, or via a hindered hydroxyl, it may be desirable to use a bridging group

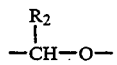

as described above for linking amide and imide groups to the phosphonate, rather than a direct bond between the drug's hydroxyl group and the phosphorus atom.

The compounds of formula (I) can be prepared by a variety of synthetic procedures tailored to the structure of the particular drug to be derivatized, particularly to the nature of the reactive functional group to be linked to the phosphonate moiety, the identity of the bridging group, if any, and the presence of other functional groups which may benefit from protection. In preferred embodiments of the invention, the drug contains a reactive hydroxyl group susceptible to direct bonding to the phosphorus atom in the phosphonate moiety. It is also preferred for simplicity's sake that the selected drug not require protection of other functional groups, although such groups can be protected when necessary. The ILLUSTRATIVE SYNTHETIC METHODS set forth hereinafter describe various methods for the preparation of the compounds of the invention, while the EXAMPLES which follow illustrate these and alternative methods. These methods can be summarized as follows for drugs in each of the major structural categories, wherein the definitions of the structural variables as set forth above in conjunction with formulas (Ia) to (If):

The compounds of formulas (Ia) and (Ib) can be synthesized by contacting the drug, D—OH or D—SH, respectively, with a substituted phosphonic dichloride $R_1P(O)Cl_2$, e.g. $CH_3P(O)Cl_2$, in pyridine. The resultant compound of the formula

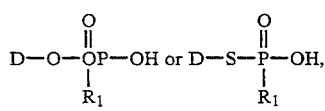

respectively, is then treated with aqueous sodium hydroxide and aqueous silver nitrate to afford the corresponding silver salt,

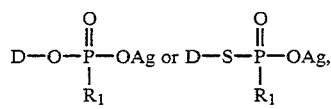

respectively. Reaction of the silver salt with

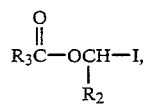

e.g.

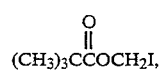

affords the corresponding compound of formula (Ia) or (Ib), respectively.

A preferred novel process which is more reliable and easily applied than that described above utilizes a cesium salt catalyst. The first step, a base-catalyzed reaction of the drug, D—OH or D—SH, respectively, with a substituted phosphonic dichloride $R_1P(O)Cl_2$, e.g. $CH_3P(O)Cl_2$, proceeds as described above. The base may be sodium carbonate, potassium carbonate or a tertiary organic amine such as triethylamine or pyridine. A non-alcoholic organic solvent, e.g. acetone, methyl ethyl ketone or acetonitrile, is employed. The phosphinic acid derivative thus produced has the same formula depicted above, i.e.

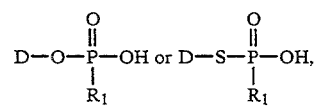

respectively. That derivative is then reacted with cesium fluoride (or equivalent cesium salt) and a compound of the formula

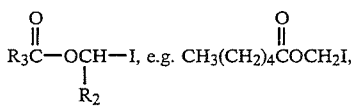

in a suitable organic solvent, e.g. dimethylformamide, acetonitrile, nitromethane, chloroform or dimethylacetamide, to give the corresponding compound of formula (Ia) or (Ib), respectively.

The compounds of formula (Ic) can be synthesized by reacting the drug D—COOH with chloromethyl chlorosulfate or similar compound of the type Cl—Z—SO$_3$Cl to give an intermediate of the type

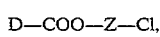

which can be reacted with a silver or cesium salt of

to afford a compound of the type

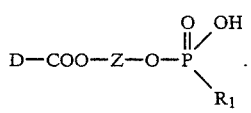

That intermediate, which contains a linking group bearing a reactive —OH, can then be reacted with cesium floride or equivalent cesium salt and a compound of the formula

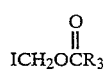

in a suitable organic solvent as discussed in the preceding paragraph, to give the corresponding compound of formula (Ic).

The compounds of formulas (Id) and (Ie) can be synthesized by reacting the drug,

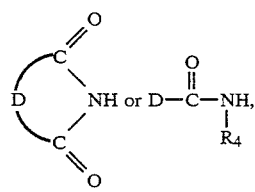

respectively, with an appropriate aldehyde of the type R$_2$CHO, e.g. formaldehyde, chloral, acetaldehyde, furfural, benzaldehyde or the like, in the presence of a basic catalyst such as potassium carbonate, to give the corresponding intermediate of the type

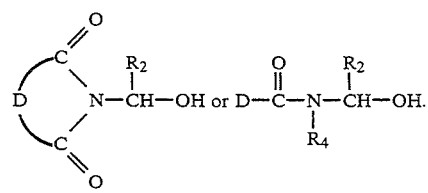

That intermediate, which contains a linking group bearing a reactive —OH, can then be reacted, first with R₁P(O)Cl₂ to give the intermediate

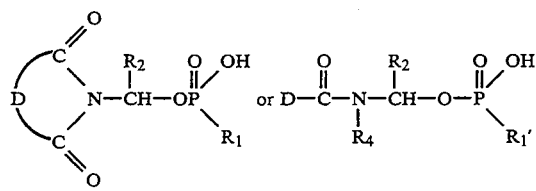

respectively, then with cesium floride or equivalent cesium salt and a compound of the formula

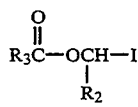

in a suitable organic solvent, as discussed hereinabove for the hydroxy-containing drugs, to give the corresponding compound of formula (Id) or (Ie), respectively. Drugs containing reactive primary or secondary sulfonamide functions (D—SO₂NH or D—SO₂NHR₄) can be derivatized similarly to the primary or secondary carboxamide-containing drugs to give analogous compounds of formula (I) and are within the ambit of the present invention. The identity of the R₄ group in the secondary amides and sulfonamides, like the R₄ group in formula (If), is immaterial in that it is of course part of the drug residue itself and is left unchanged by derivatization in accord with this invention.

The compounds of formula (If) can be synthesized by reacting the drug DNHR₄, with a halo(optionally substituted methyl)chloroformate to give an intermediate of the type

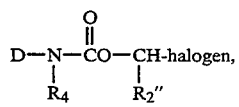

which can then be reacted with a silver or cesium salt of

to afford a compound of the type

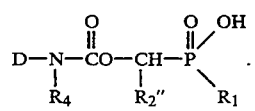

That intermediate, which contains a linking group bearing a reactive —OH, can then be reacted with cesium floride or equivalent cesium salt and a compound of the formula

in a suitable organic solvent as discussed hereinabove, to give the corresponding compound of formula (If).

When required, the various protecting groups for hydroxyl, carboxyl and amino functions discussed above can be substituted for the hydroxyl, carboxyl and amino functions in the instant compounds or their precursor molecules by methods well-known in the art. Most frequently, the protecting group will first be introduced into the drug molecule by well-known methods and the protected drug will then be subjected to the processes described above for preparation of the instant compounds. Methods for chemical removal of the protecting groups (when such are not to be retained in the pharmaceutically useful end product) are likewise well-known to those skilled in the art. Typically, amine protecting groups are chemically removed by acidolysis (acid hydrolysis) or hydrogenation, depending on the particular protecting group employed. Hydroxyl and carboxyl protecting groups are typically removed chemically by acid or base hydrolysis. Protecting groups which are incorporated into the pharmaceutical end product must be amenable to hydrolytic or metabolic cleavage in vivo.

The starting materials needed for the various processes described above are commercially available or can be readily prepared by known methods.

ILLUSTRATIVE SYNTHETIC METHODS

I. Methods for Derivatizing —OH and —SH Functions in Drugs

METHOD A

The drug containing a reactive hydroxyl or mercapto function is reacted with CH₃P(O)Cl₂ (methyl phosphonic dichloride) in a nonalcoholic organic solvent such as acetone, in the presence of sodium carbonate or other appropriate basic catalyst, to afford the intermediate phosphonic acid derivative. The phosphonic acid intermediate is then reacted with cesium fluoride and

in an organic solvent such as dimethylformamide to give the desired compound of formula (Ia) or (Ib). The representative drugs depicted below ("Starting Material") may be derivatized in this manner, first to the phosphonic acid intermediate ("Intermediate"), and then to the corresponding compound of formula (Ia) or (Ib) ("Final Product").

| Starting Material | Intermediate | Final Product |

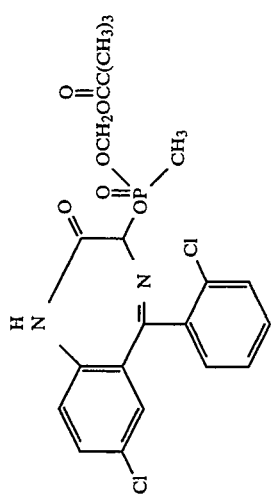
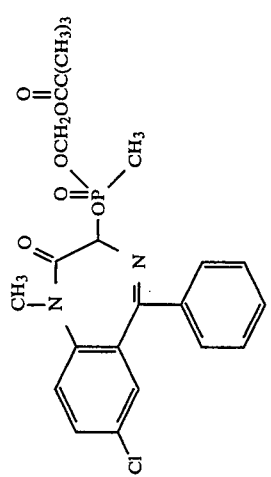
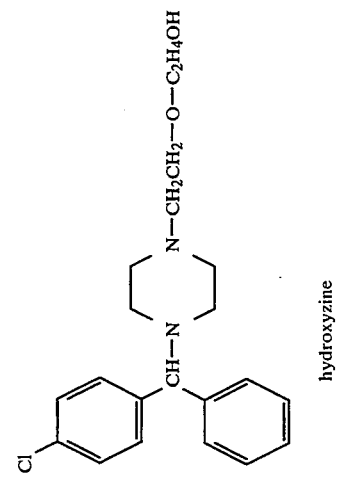
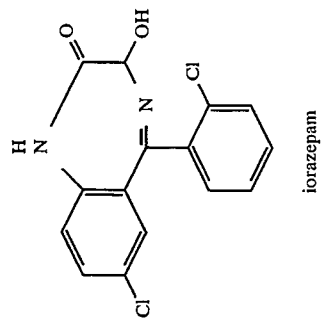
lorazepam
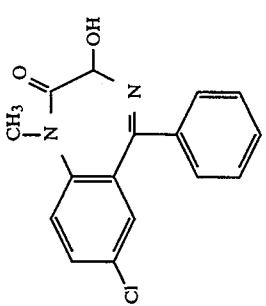
temazepam
hydroxyzine -continued
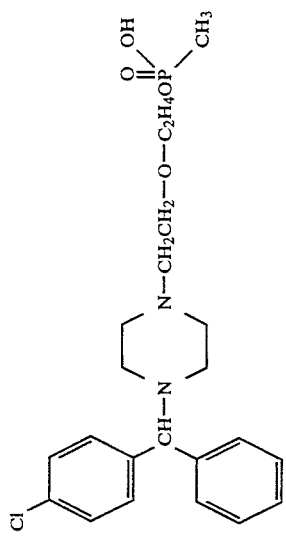
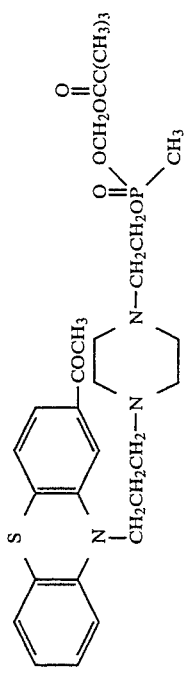
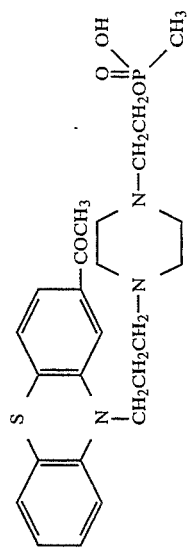
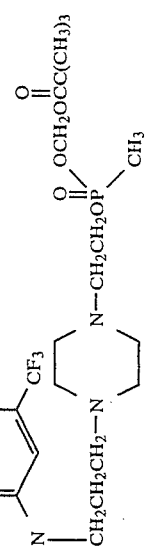
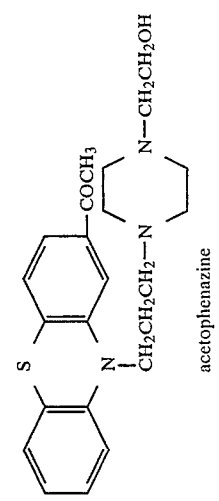
acetophenazine
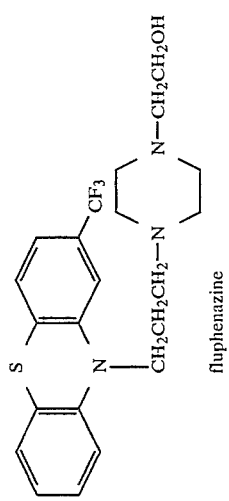
fluphenazine -continued
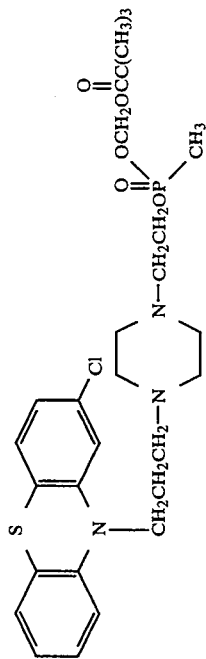
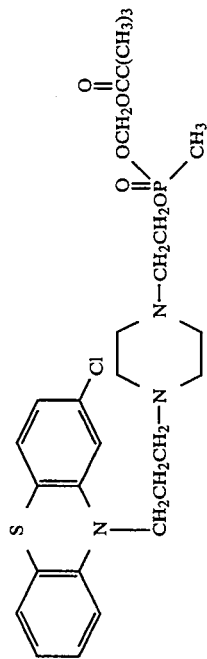
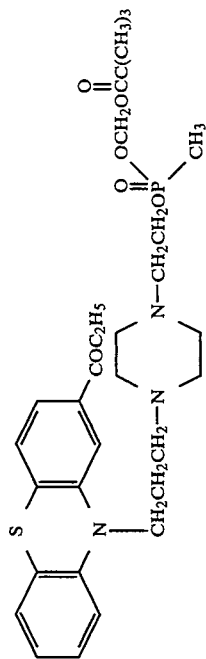
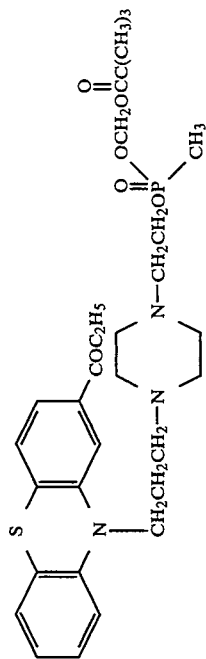
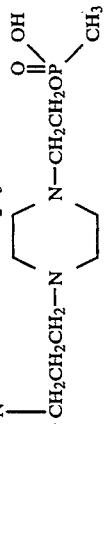
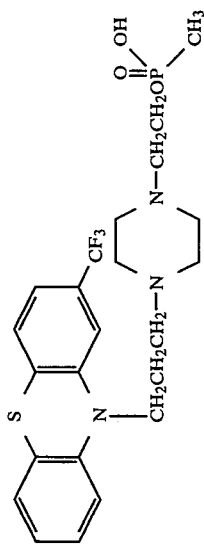
perphenazine
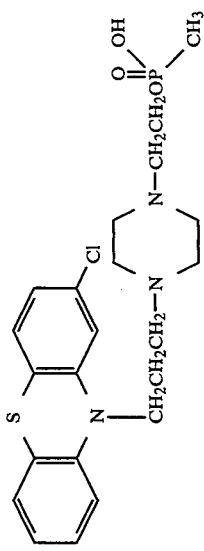
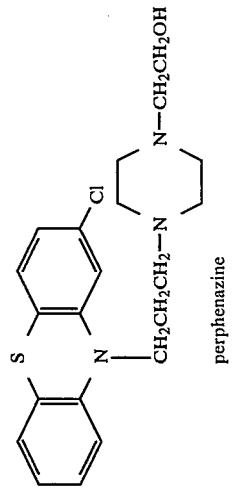
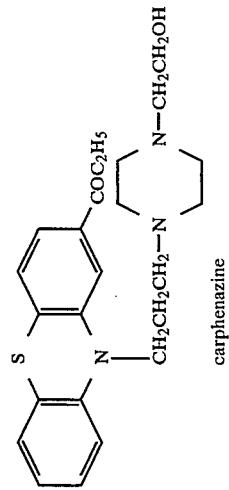
carphenazine

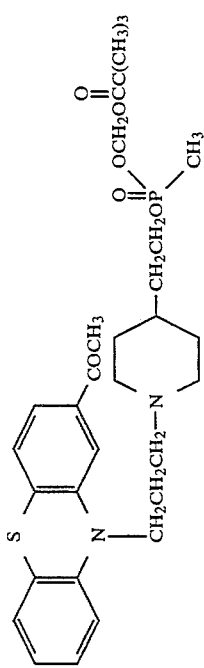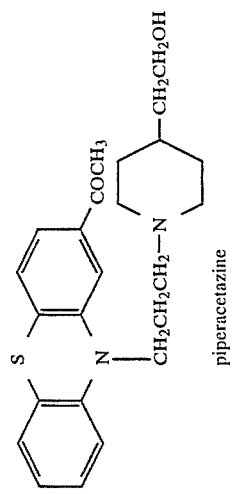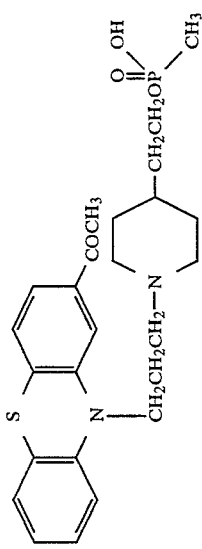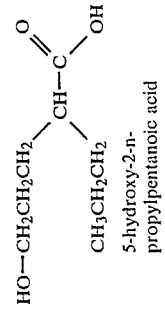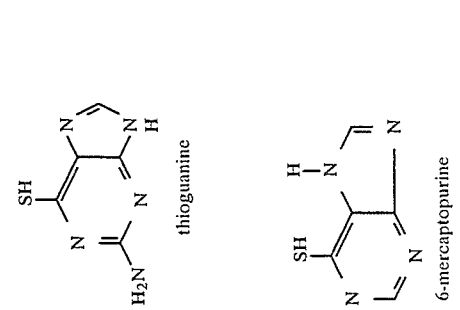

47
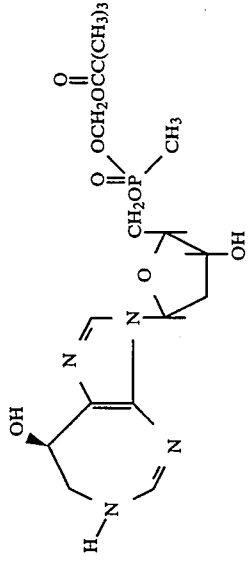
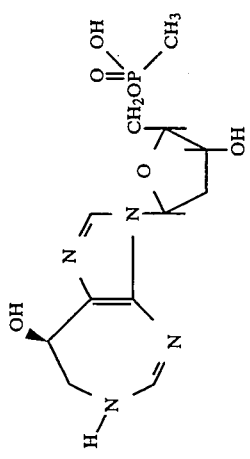
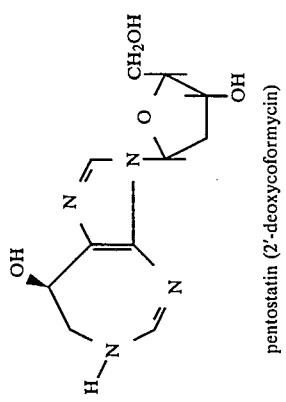
pentostatin (2'-deoxycoformycin)
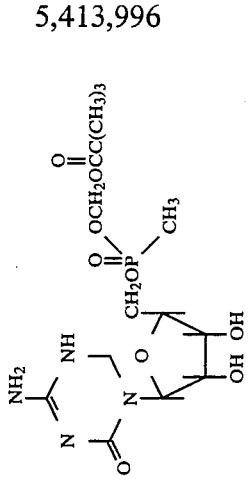
-continued
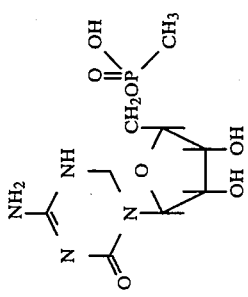
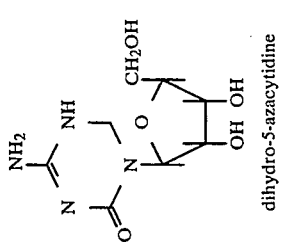
dihydro-5-azacytidine
48
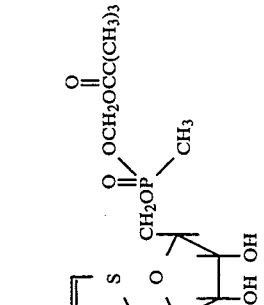
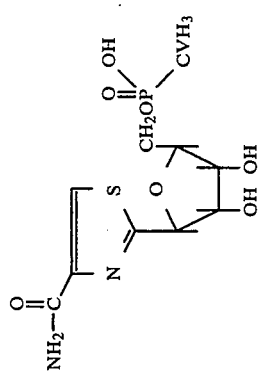
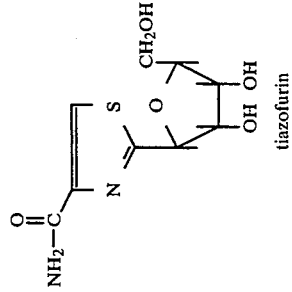
tiazofurin

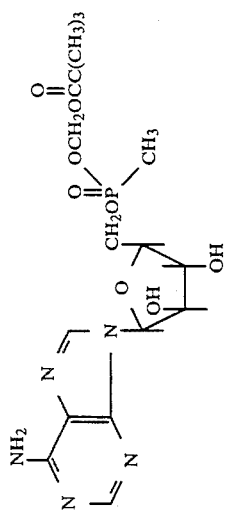
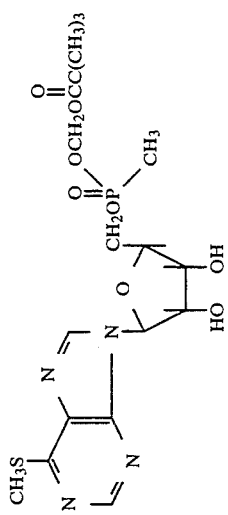
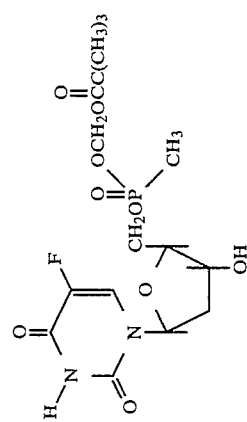
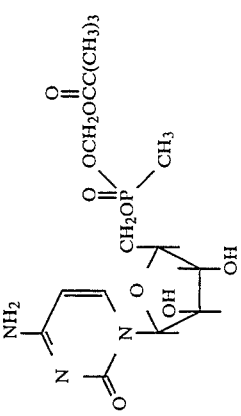
-continued
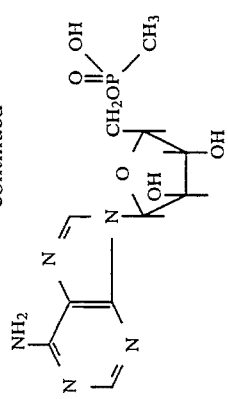
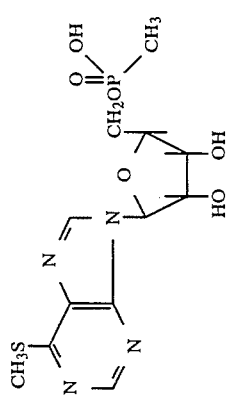
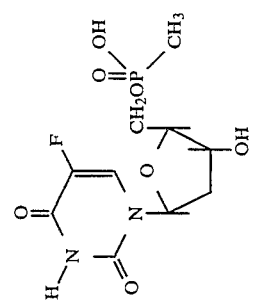
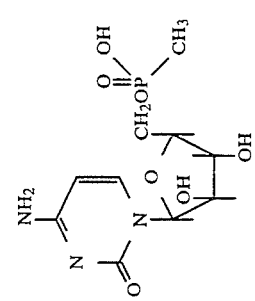
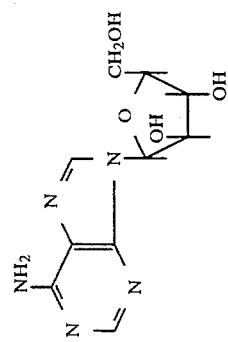
vidarabine (Ara-A)
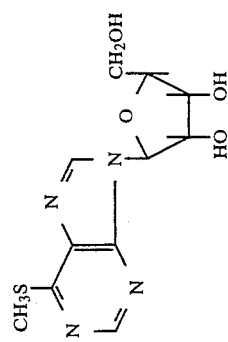
6-MMPR
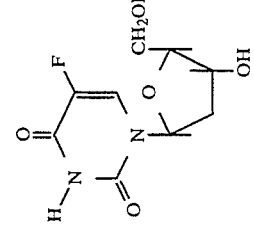
5-FUDR (floxuridine)
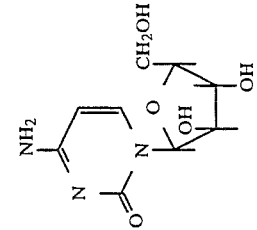
cytarabine (Ara-C; cytosine arabinoside)

-continued
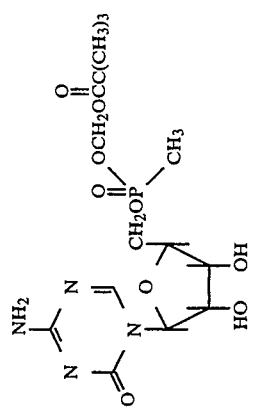
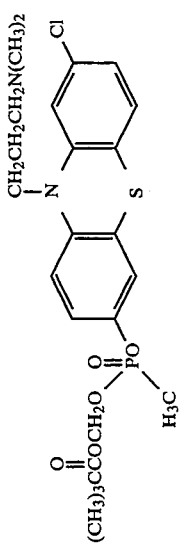
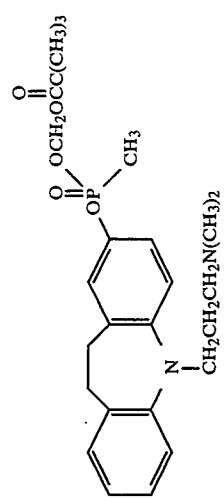
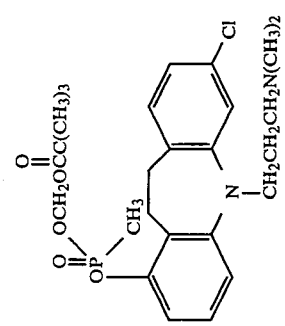
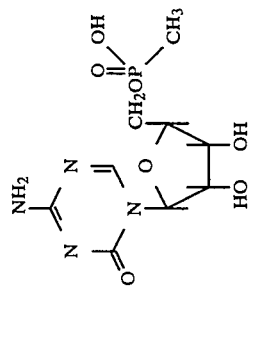
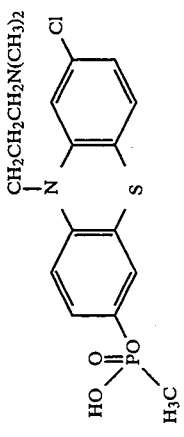
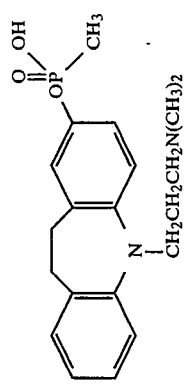
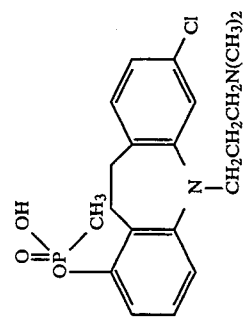
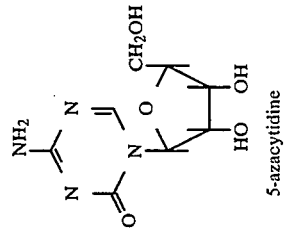
5-azacytidine
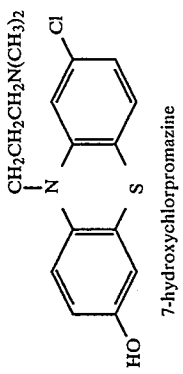
7-hydroxychlorpromazine
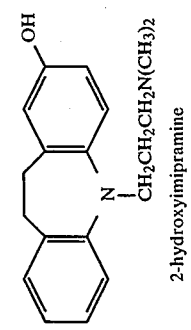
2-hydroxyimipramine
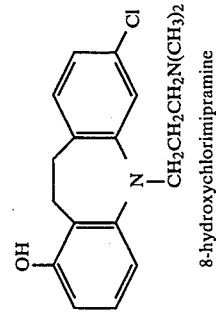
8-hydroxychlorimipramine 53 54
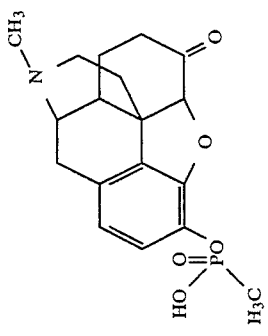 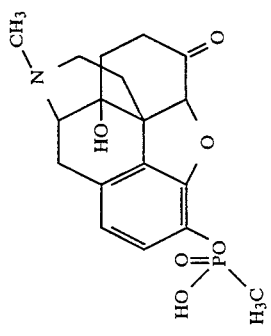 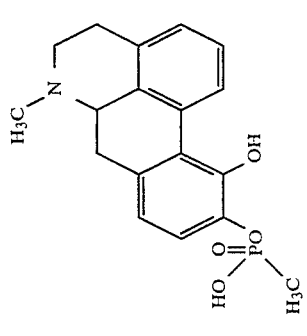
-continued
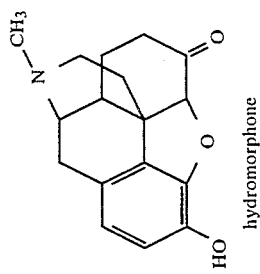 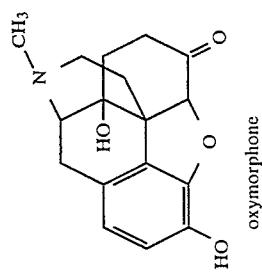 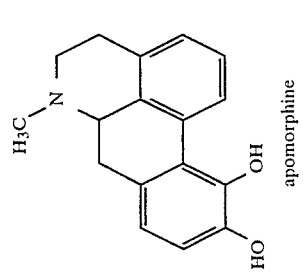

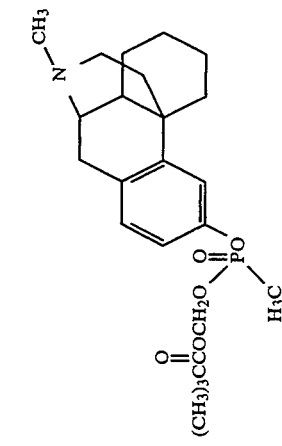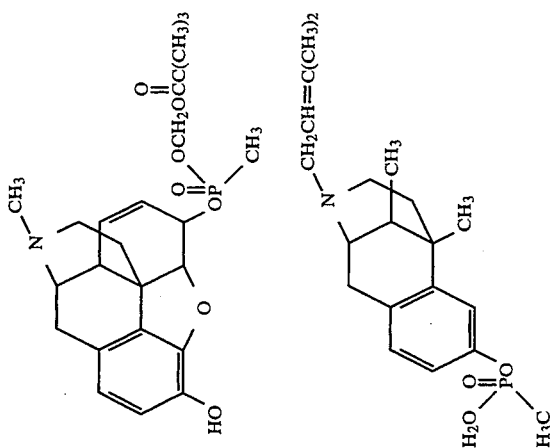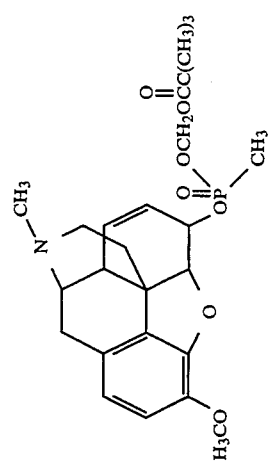
-continued
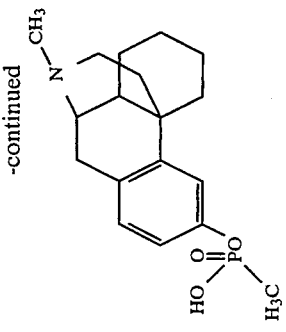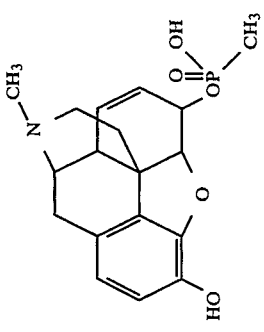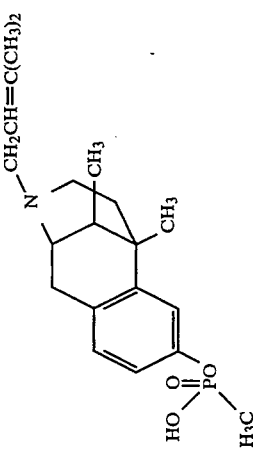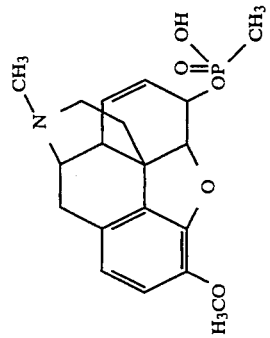
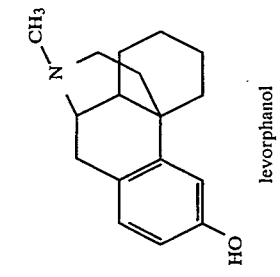
levorphanol
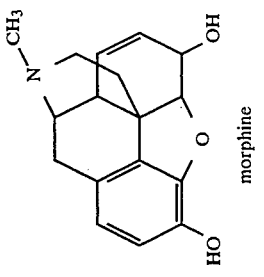
morphine
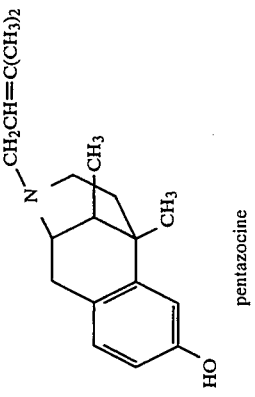
pentazocine
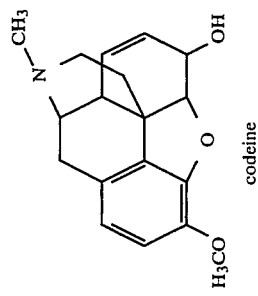
codeine

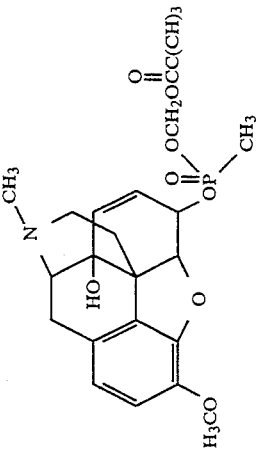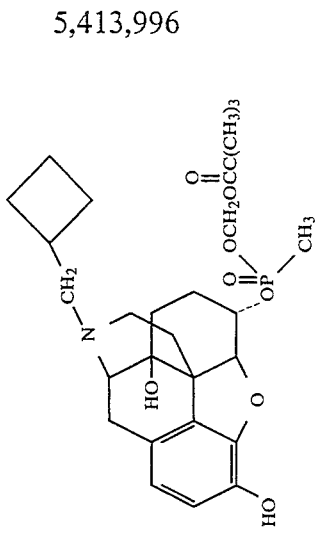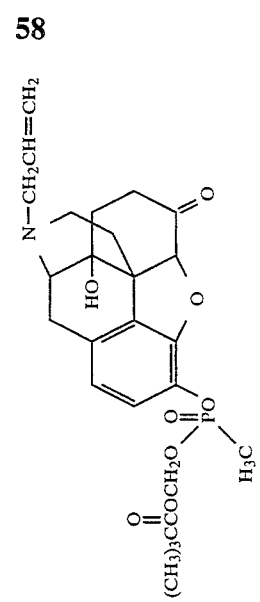
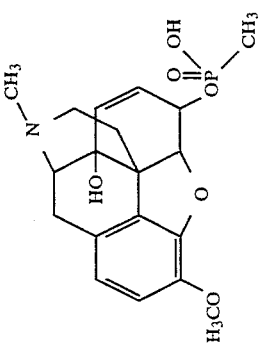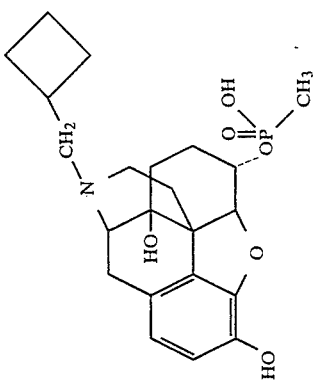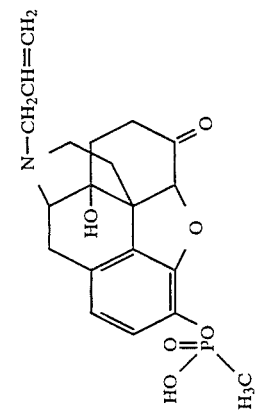
-continued
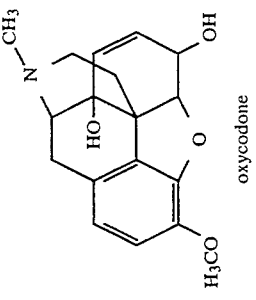
oxycodone
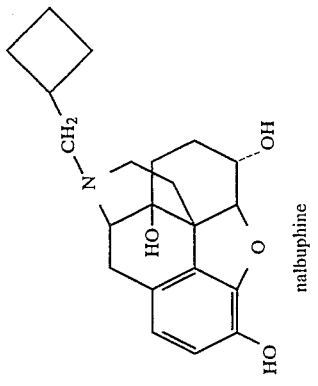
nalbuphine
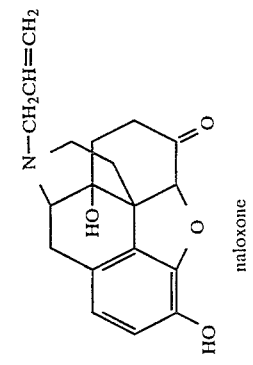
naloxone

59 60
-continued
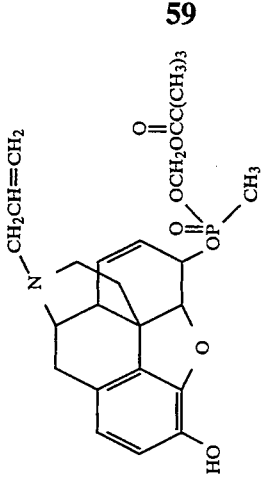
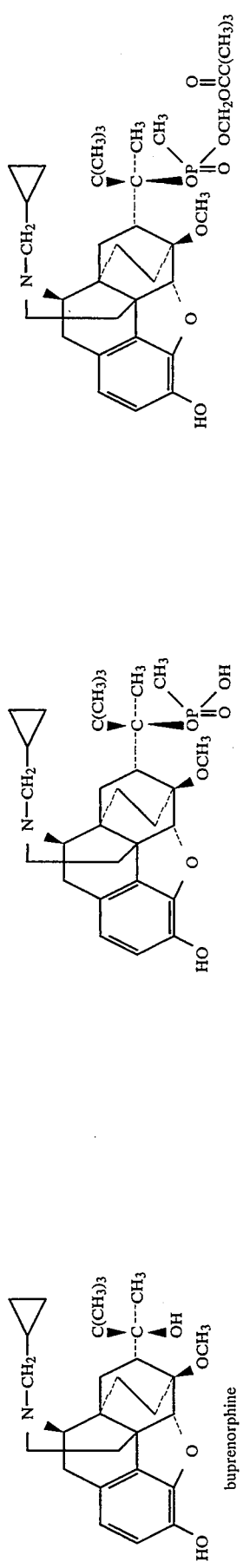
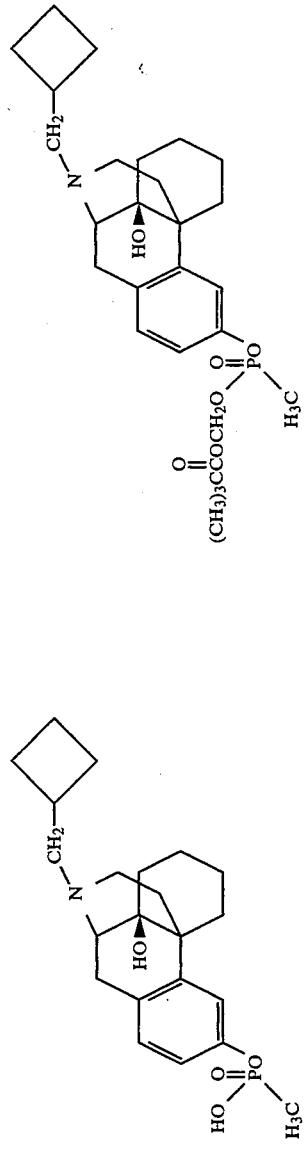
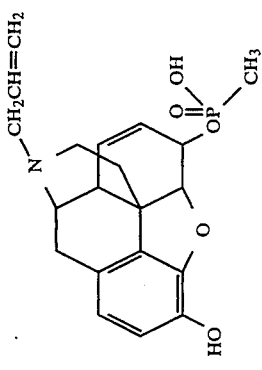
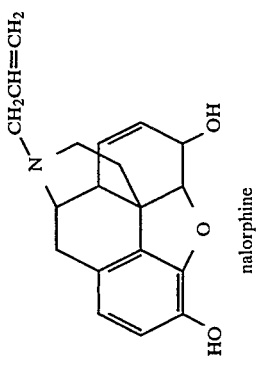
nalorphine
buprenorphine
butorphanol

61
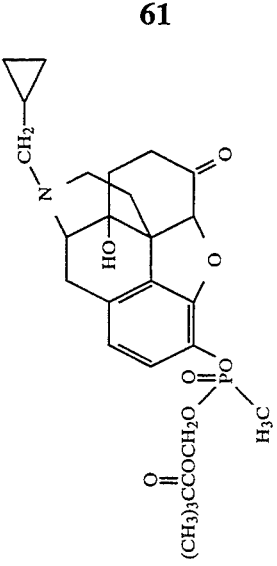
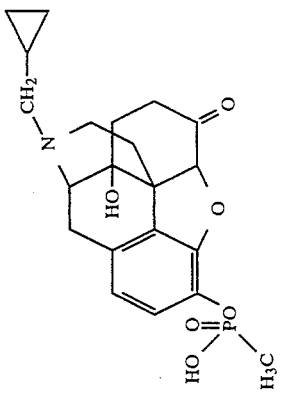
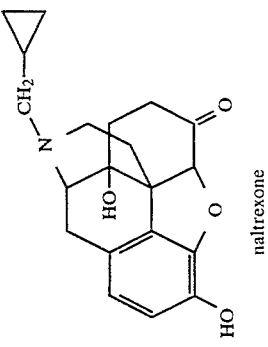
naltrexone
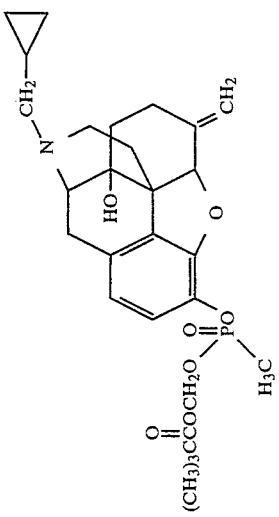
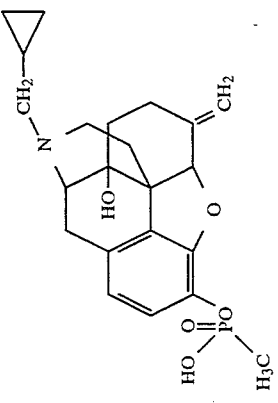
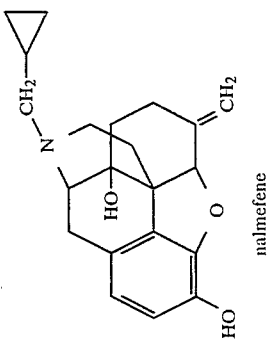
nalmefene
62
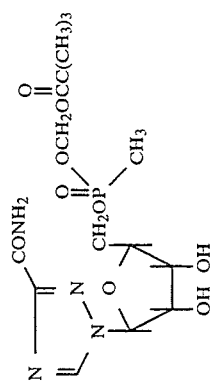
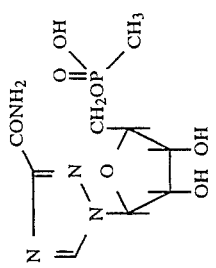
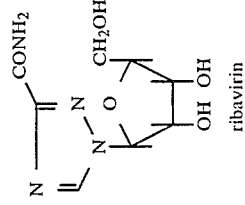
ribavirin

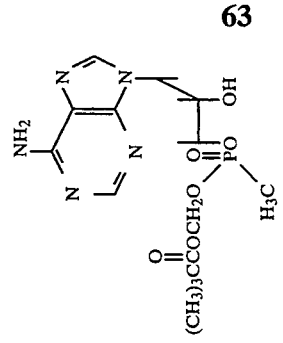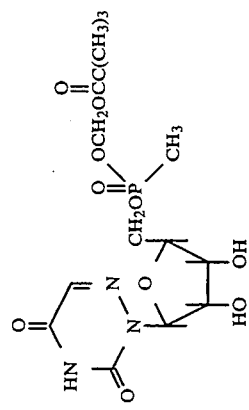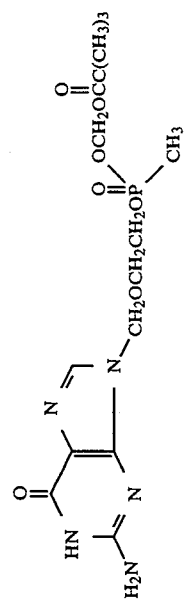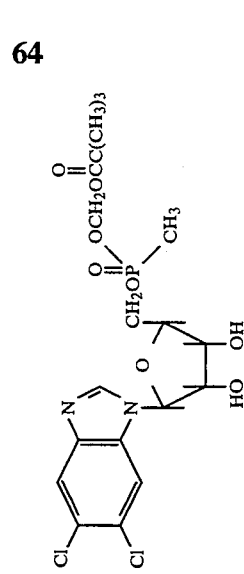
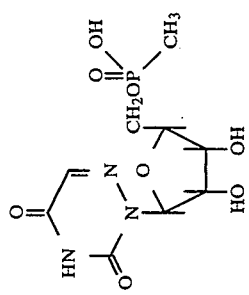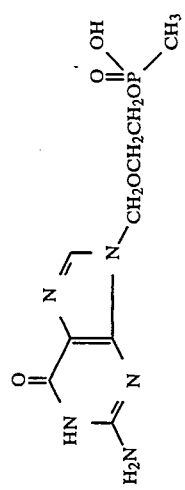
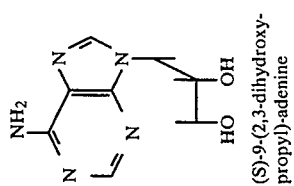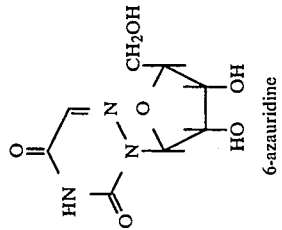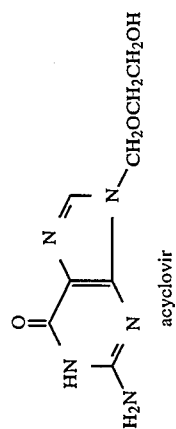

65
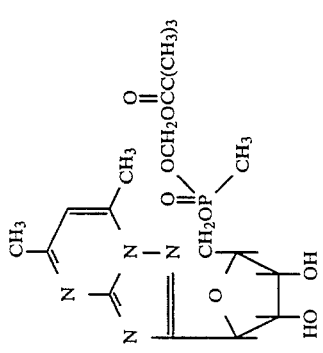
-continued
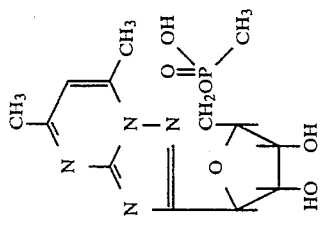
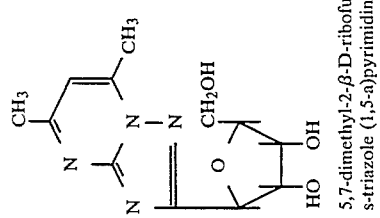
5,7-dimethyl-2-β-D-ribofuranosyl-
s-triazole (1,5-a)pyrimidine
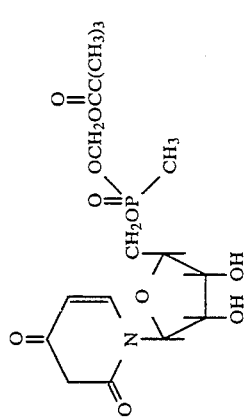
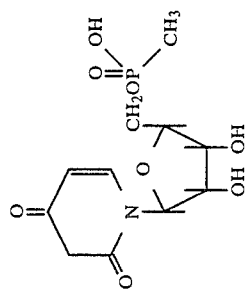
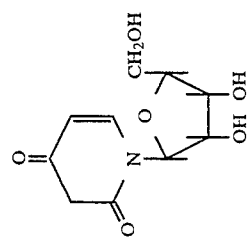
3-deazauridine
66
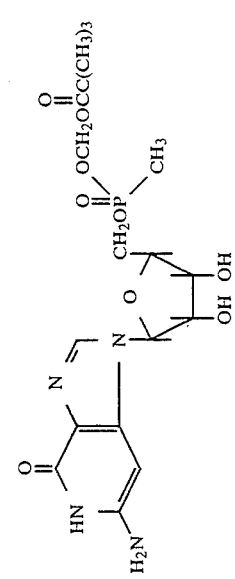
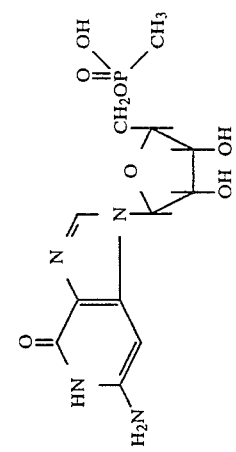
3-deazaguanosine

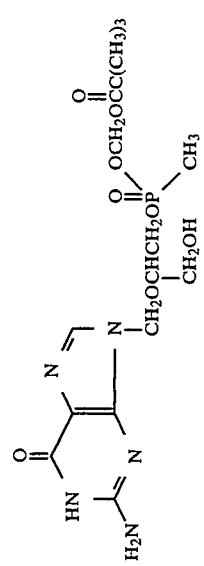
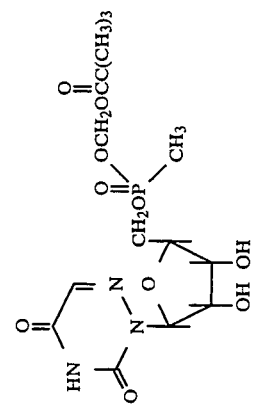
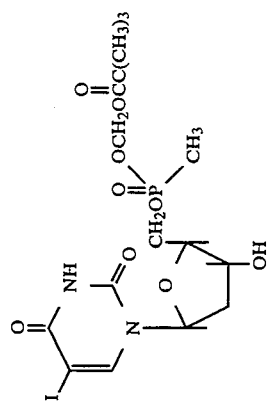
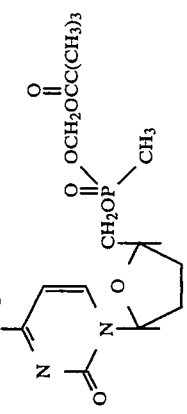
-continued
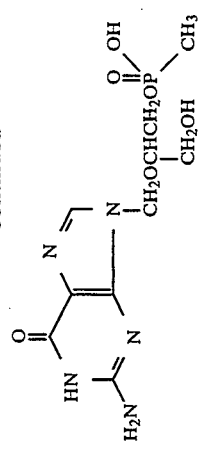
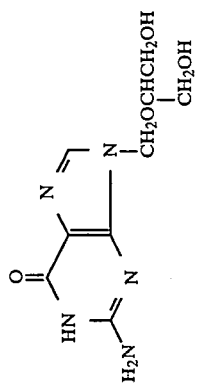
ganciclovir (DHPG)
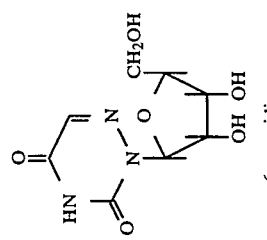
6-azauridine    idoxuridine    dideoxycytidine (DDC)

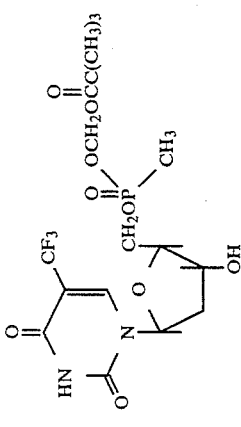
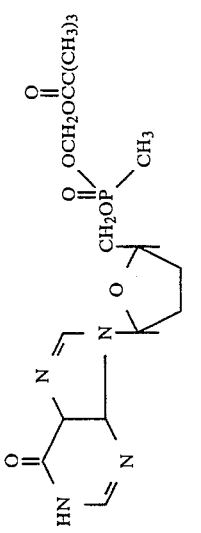
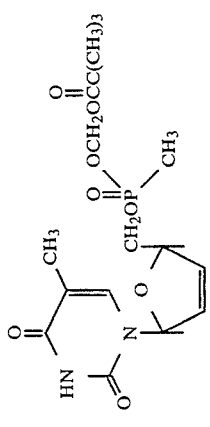
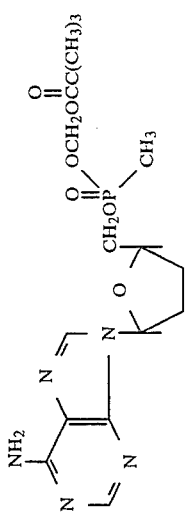
-continued
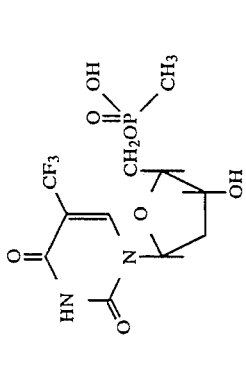
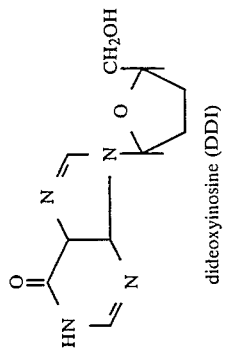
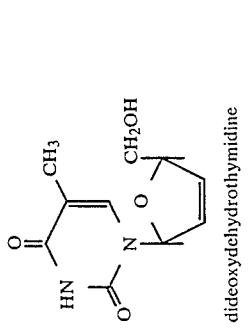
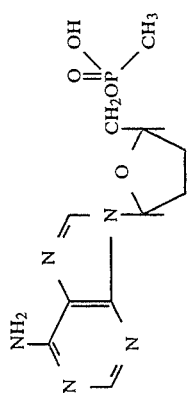
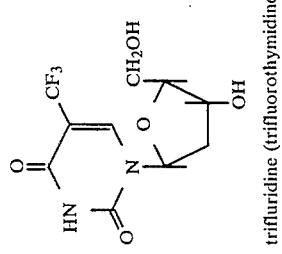
trifluridine (trifluorothymidine)
dideoxyinosine (DDI)
dideoxydehydrothymidine
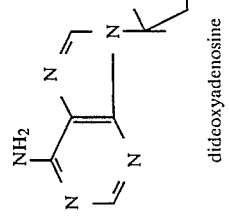
dideoxyadenosine

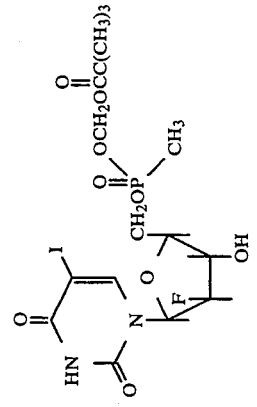
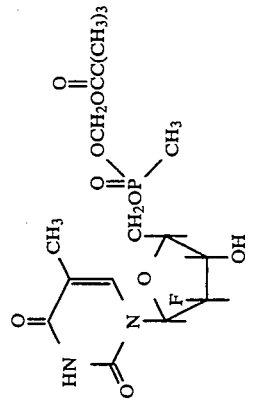
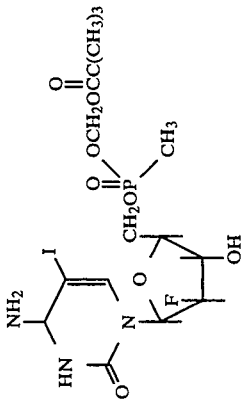
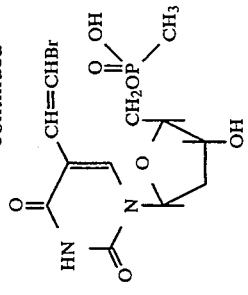
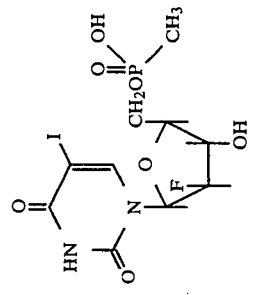
-continued
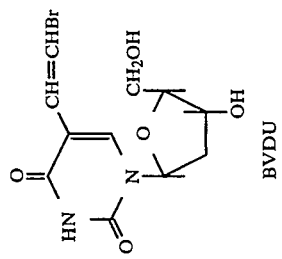
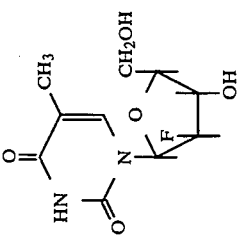
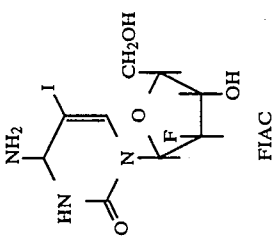
BVDU FIAU FMAU FIAC

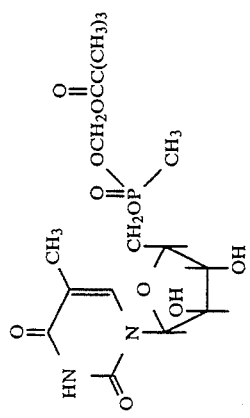 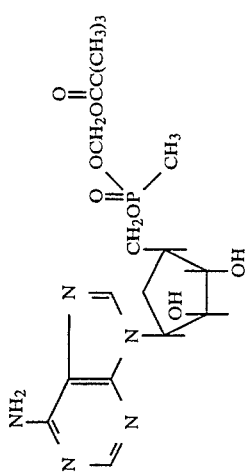 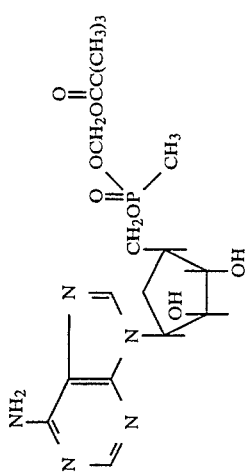 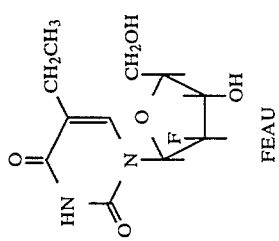
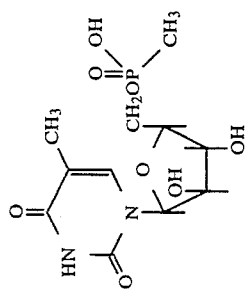 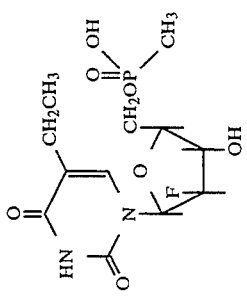 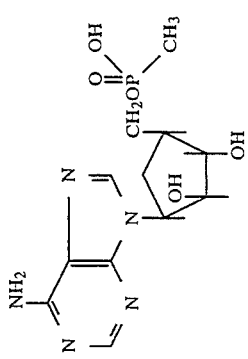
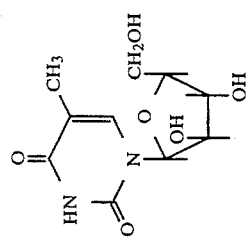 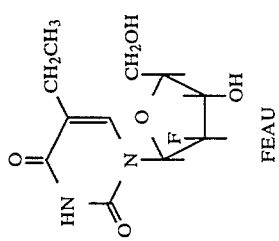 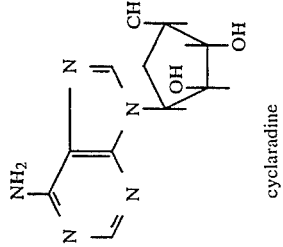 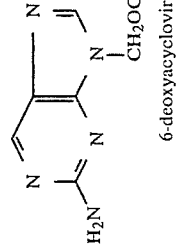

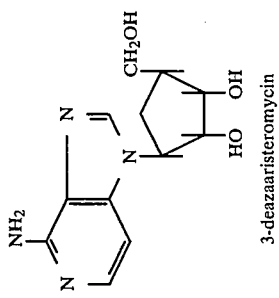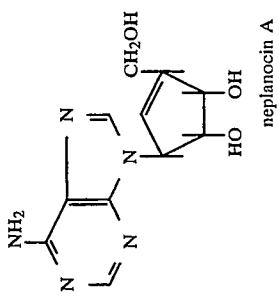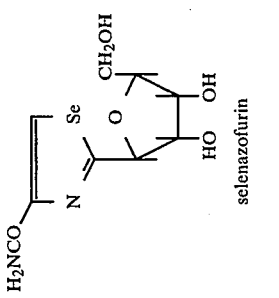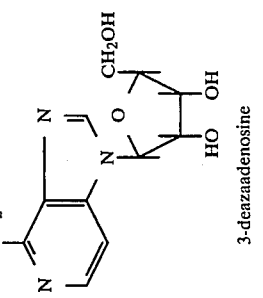
-continued
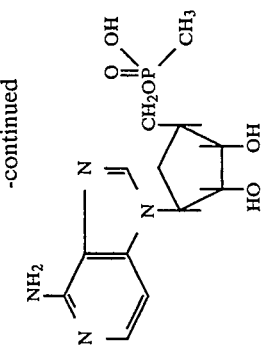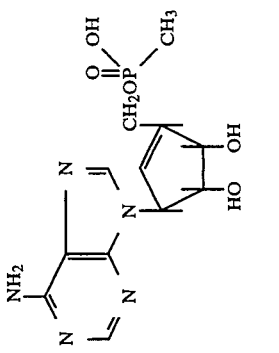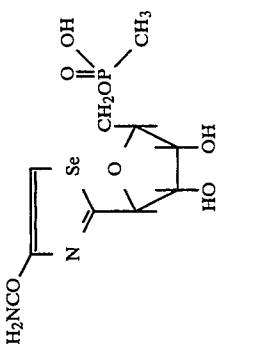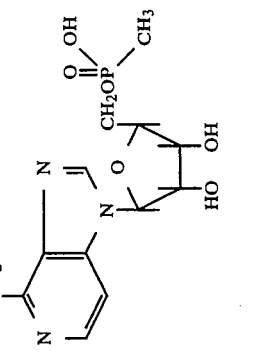
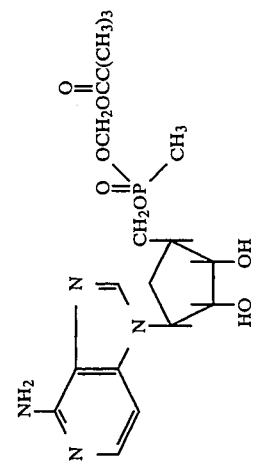
3-deazaaristeromycin
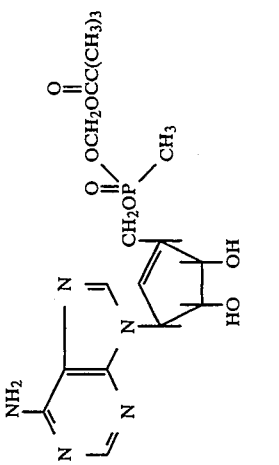
neplanocin A
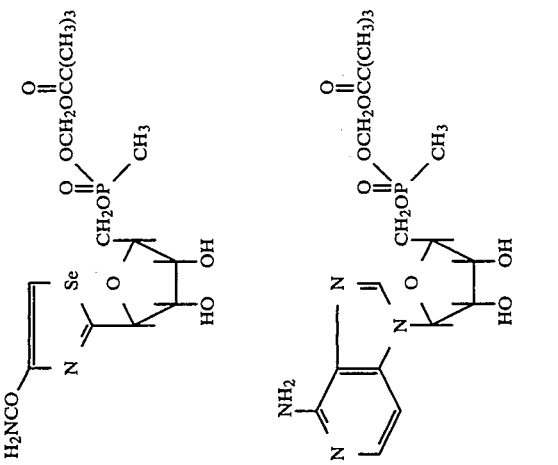
selenazofurin    3-deazaadenosine

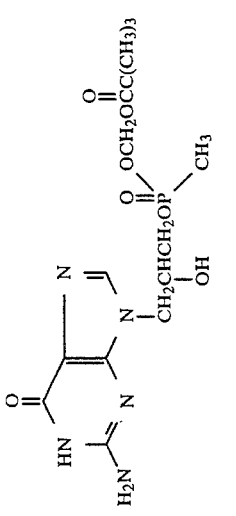 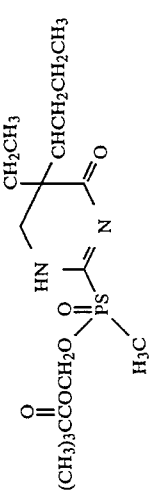 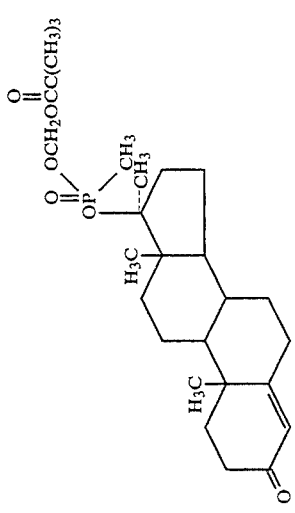 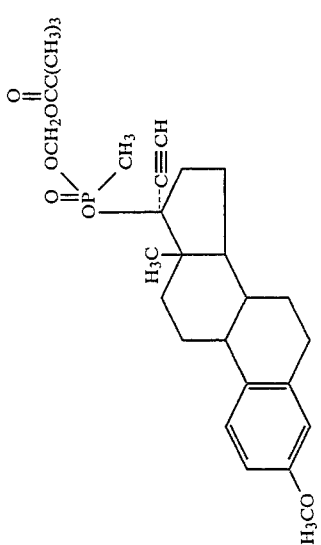
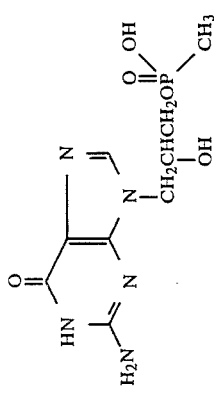 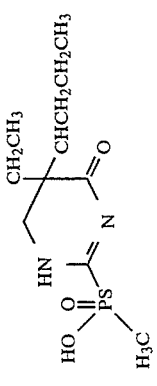
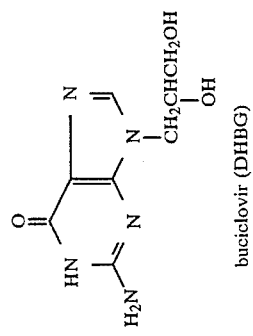 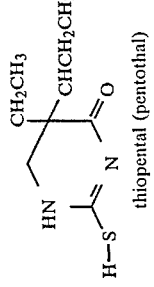 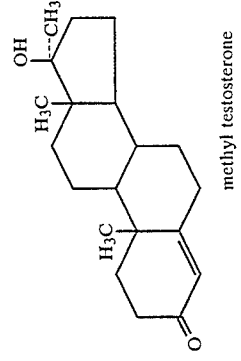 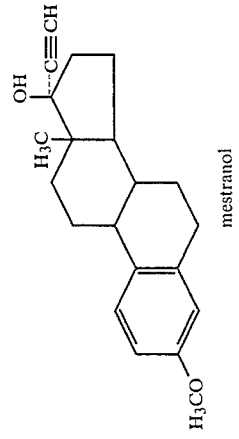

-continued
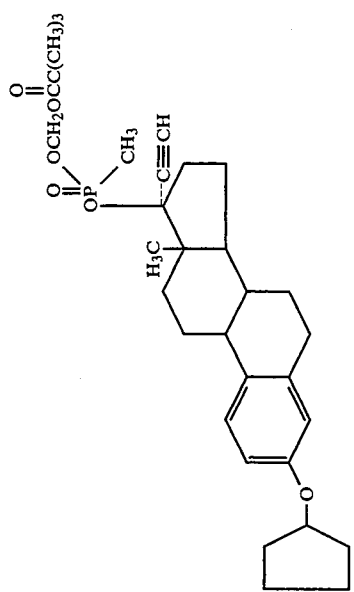
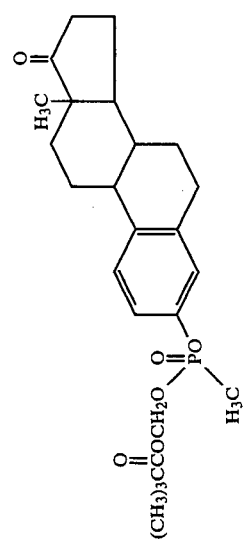
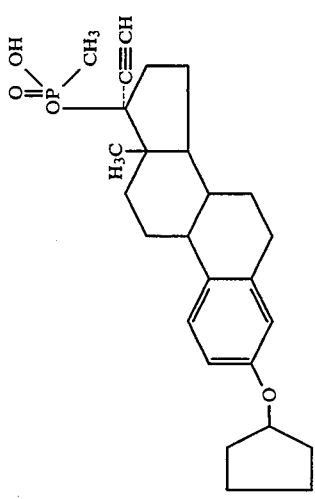
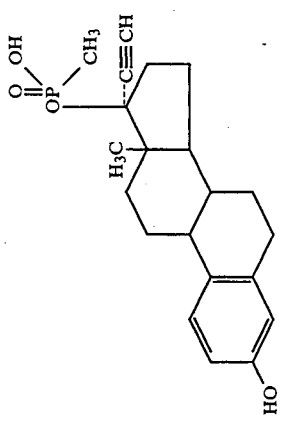
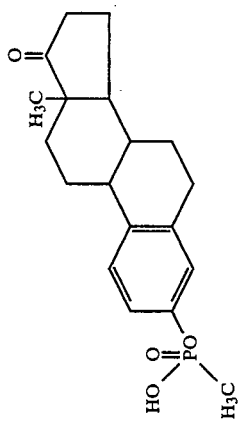
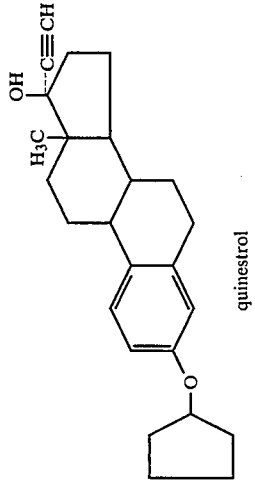
quinestrol
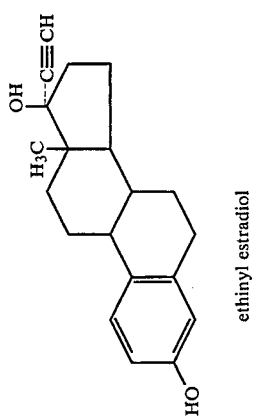
ethinyl estradiol
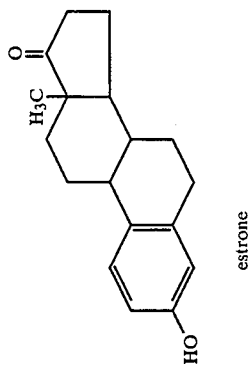
estrone

81
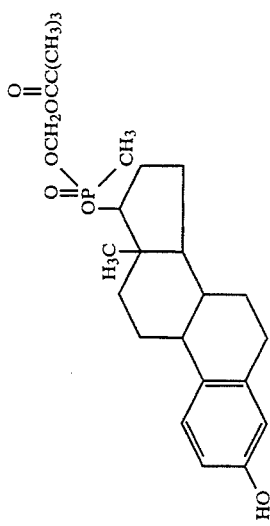
82
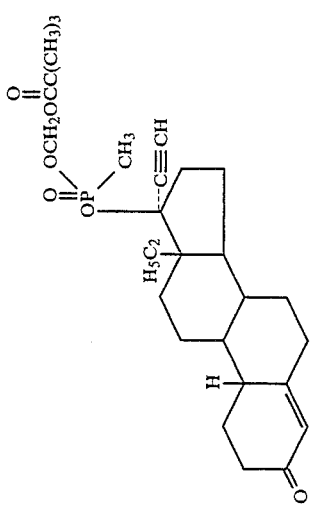
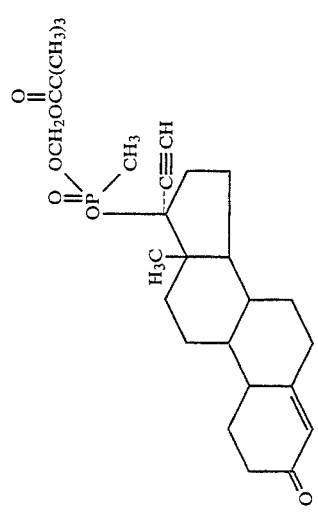
-continued
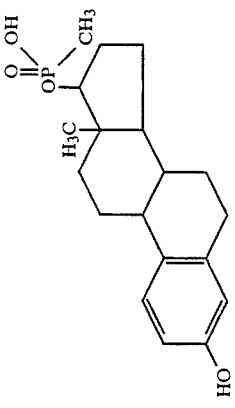
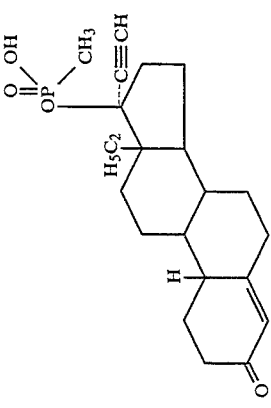
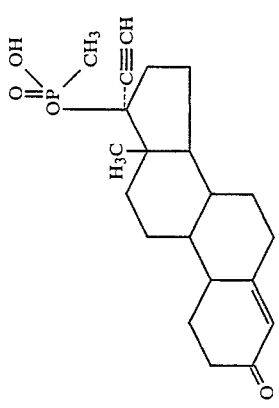
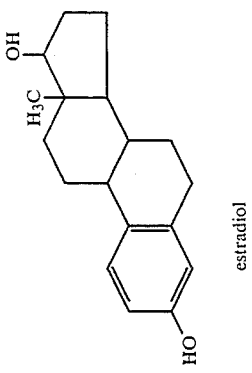
estradiol
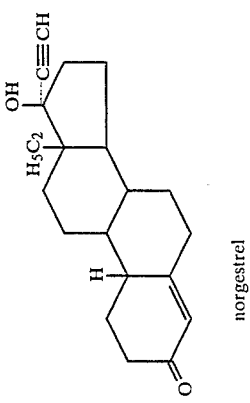
norgestrel
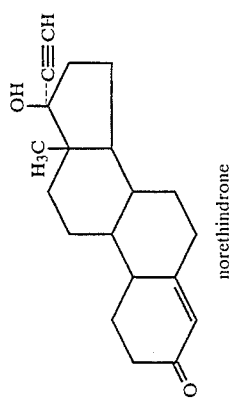
norethindrone 83
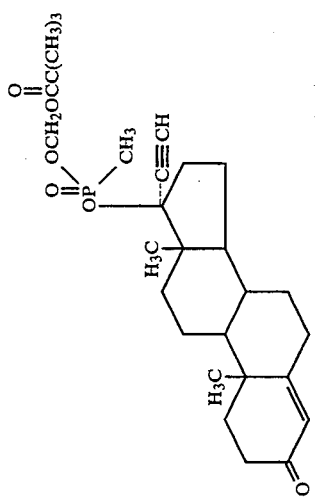
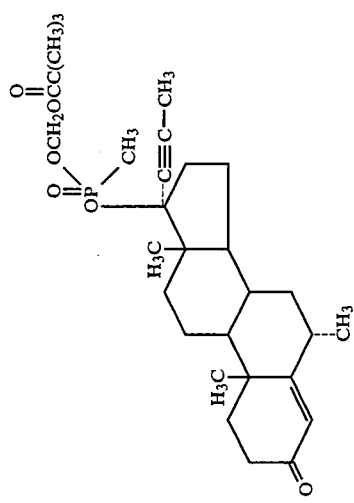
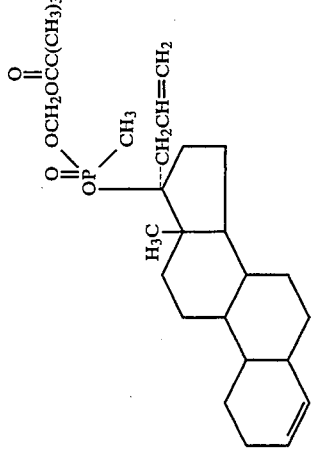
84
-continued
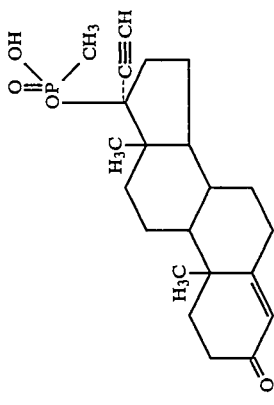
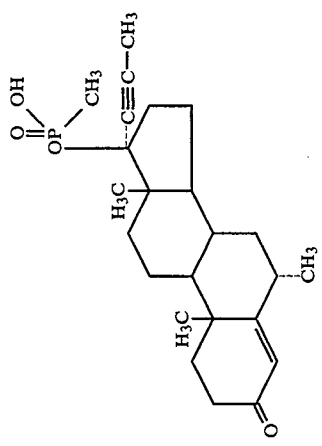
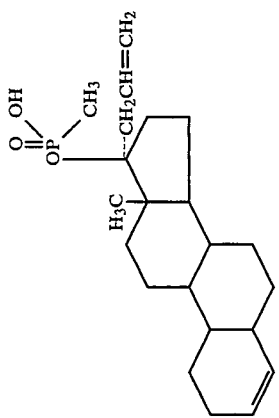
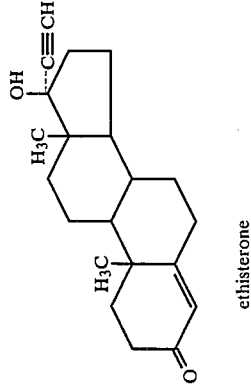
ethisterone
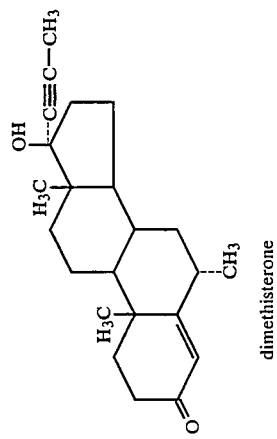
dimethisterone
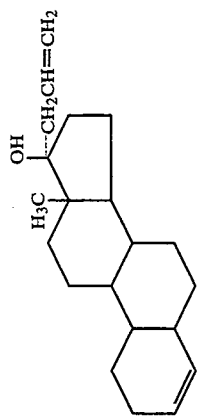
allylestrenol -continued
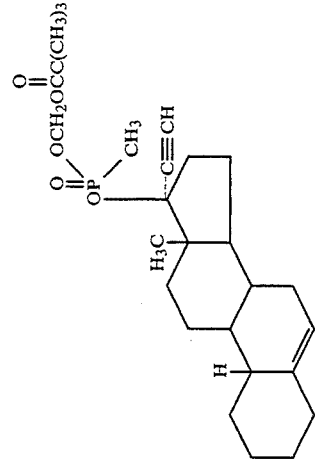
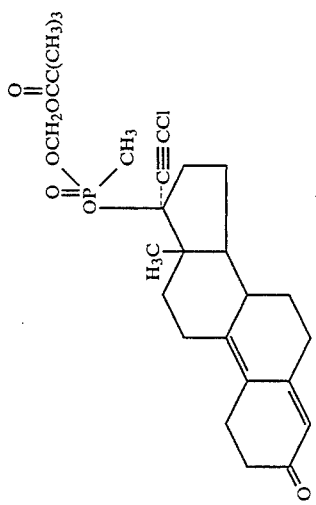
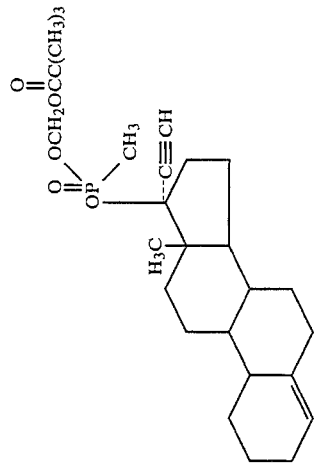
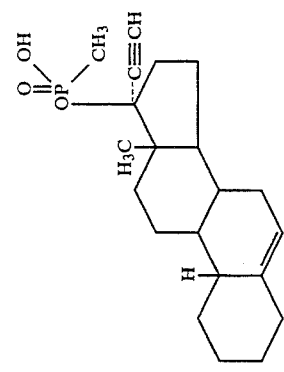
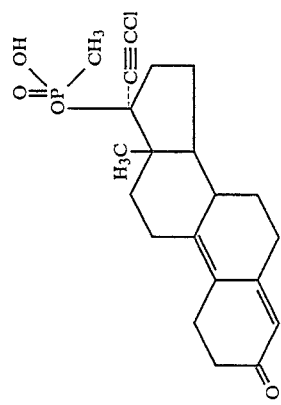
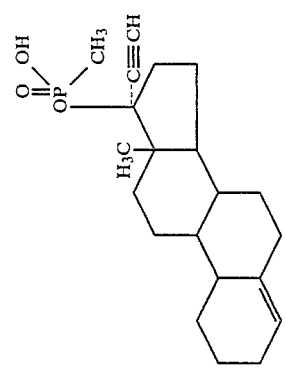
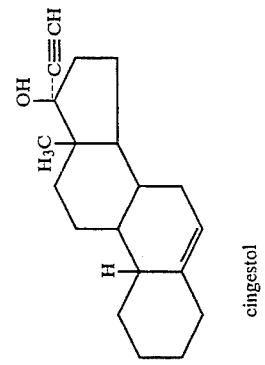
cingestol
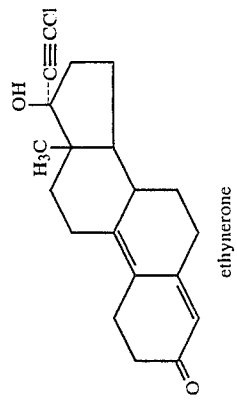
ethynerone
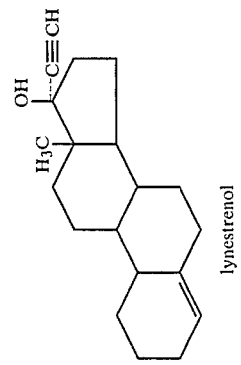
lynestrenol

87
88
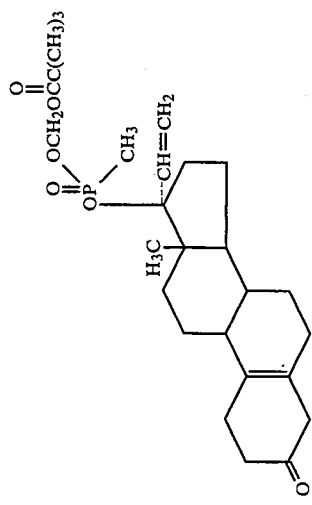
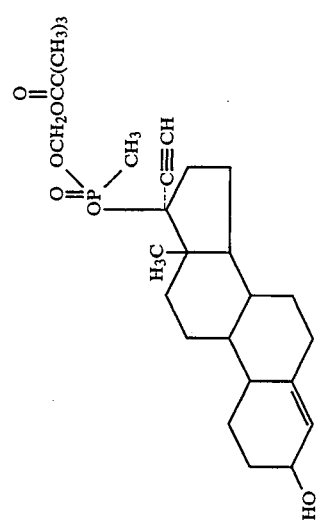
-continued
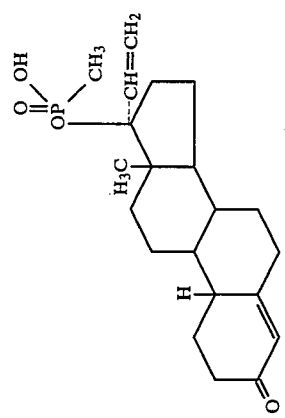
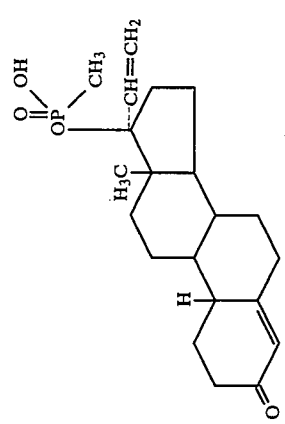
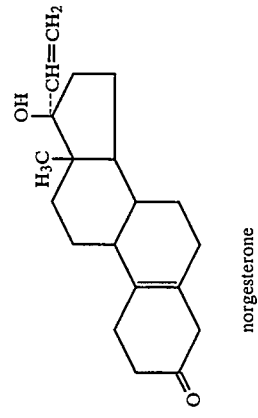
norgesterone
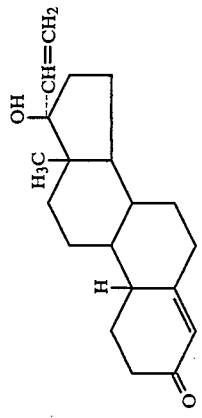
norvinisterone
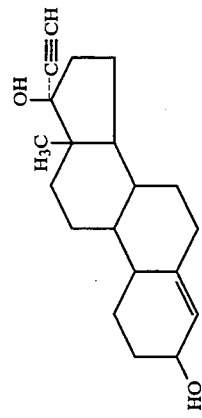
ethynodiol -continued
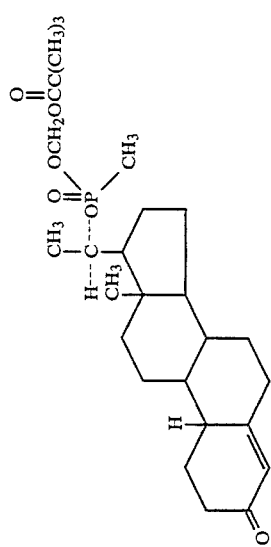
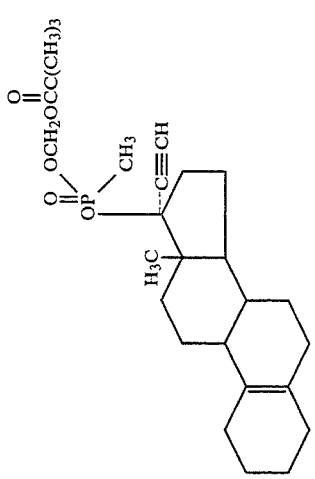
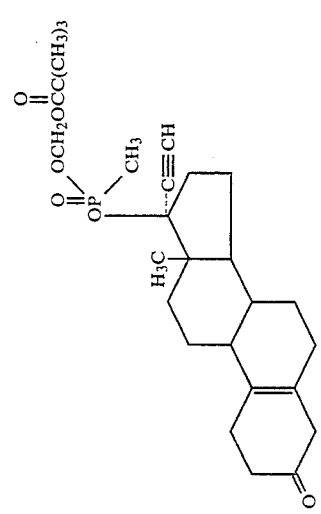
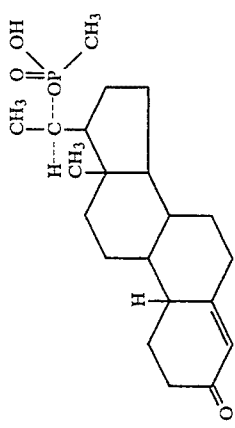
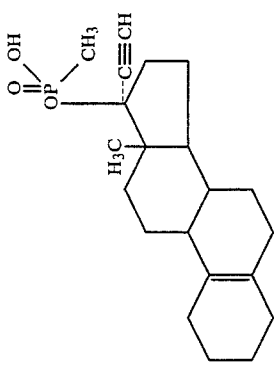
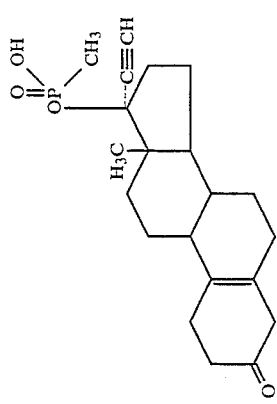
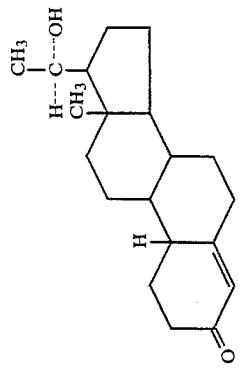
oxogestone
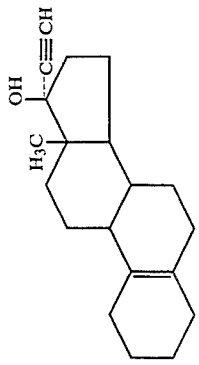
tigestol
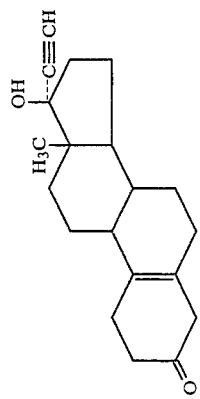
norethynodrel 91 92
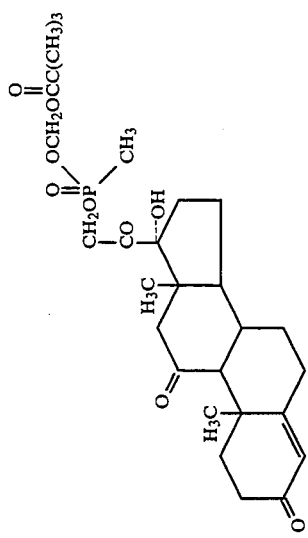
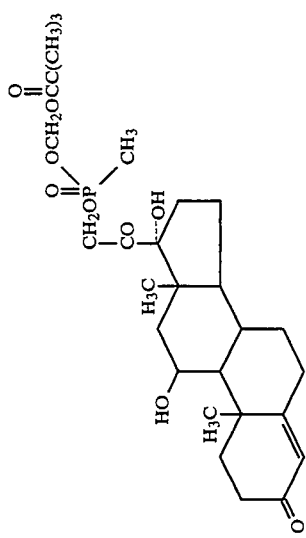
-continued
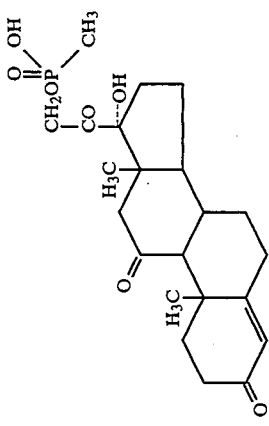
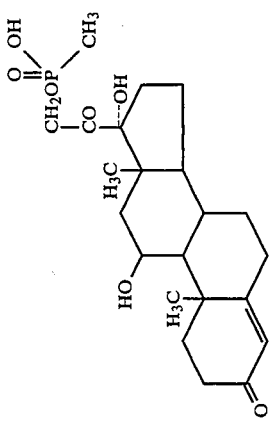
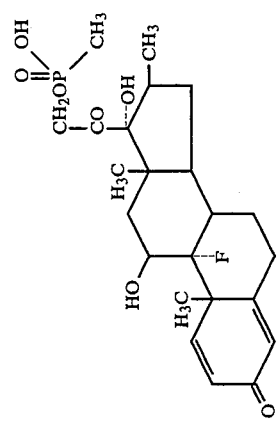
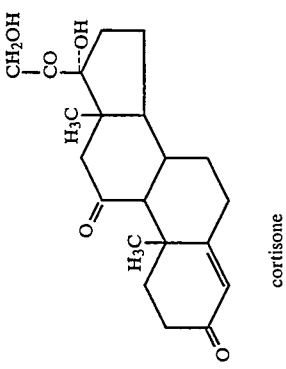
cortisone
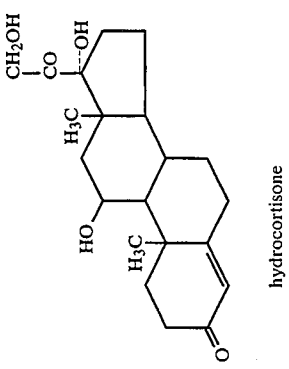
hydrocortisone
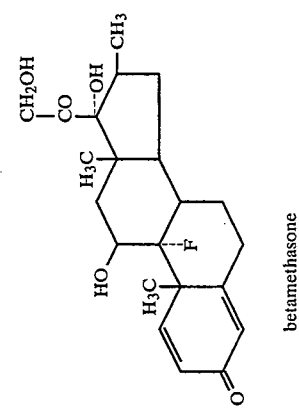
betamethasone -continued
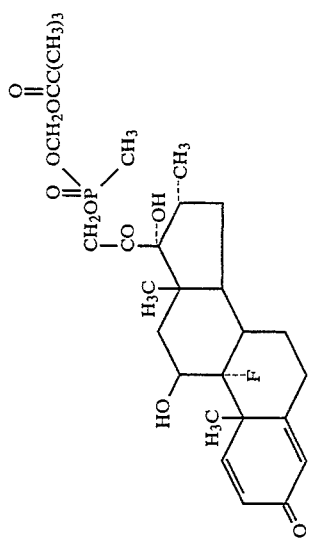
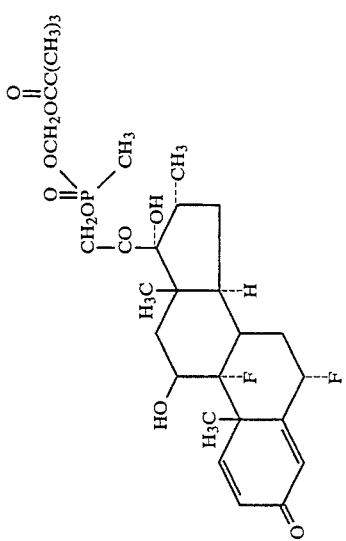
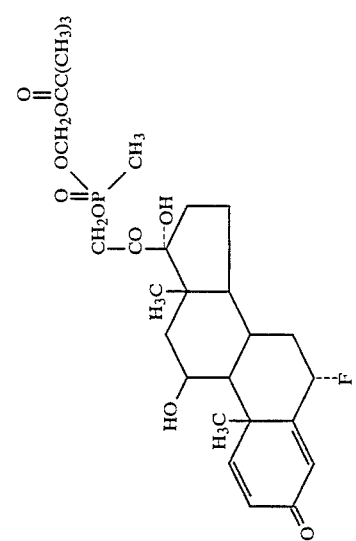
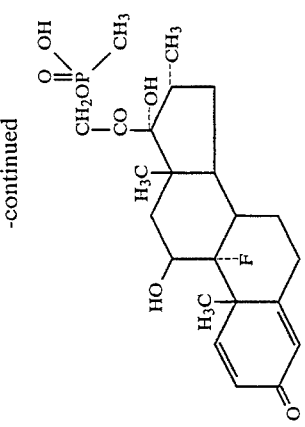
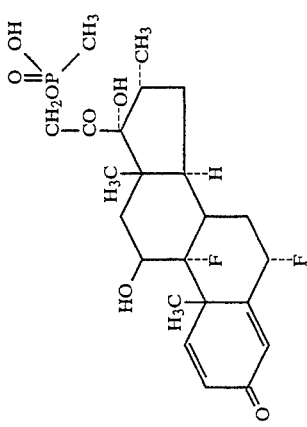
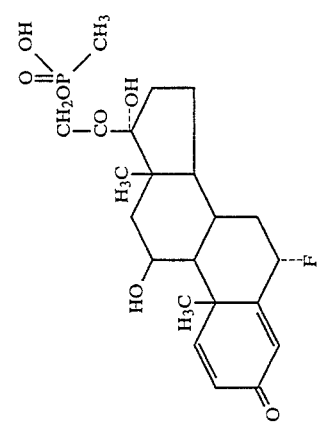
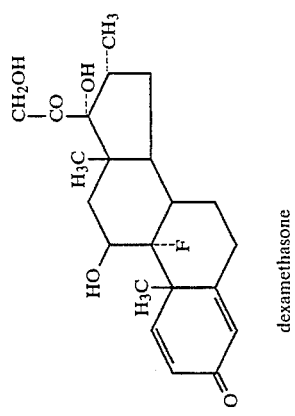
dexamethasone
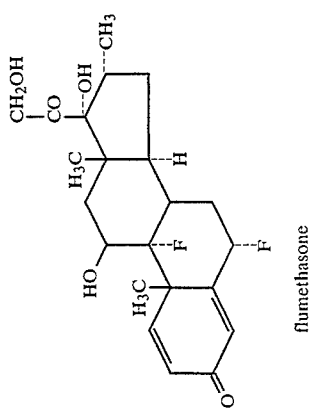
flumethasone
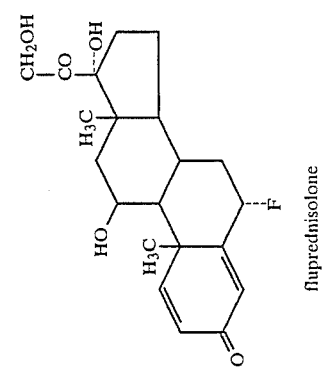
fluprednisolone 95
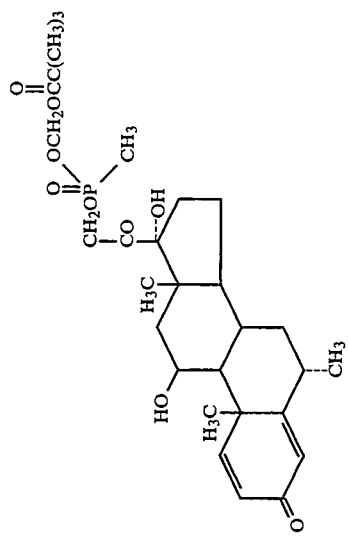
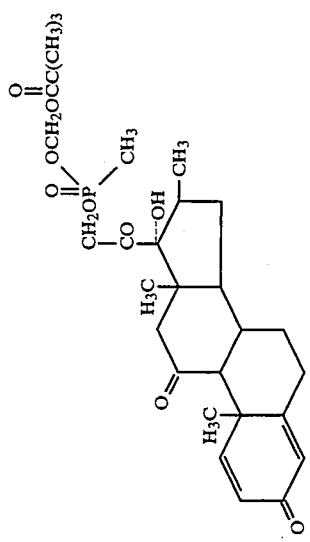
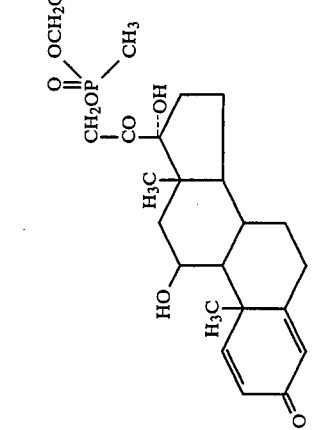
96
-continued
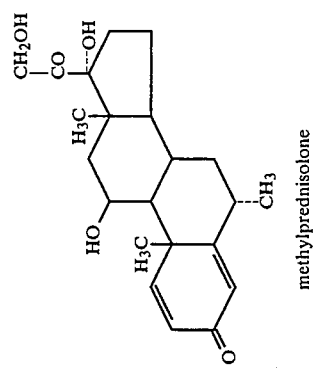
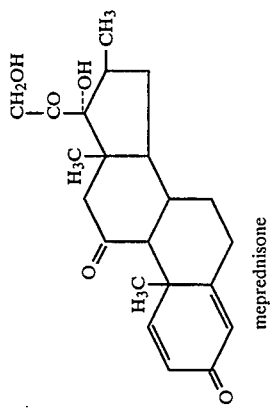
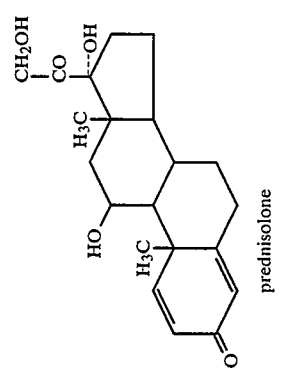
methylprednisolone
meprednisone
prednisolone

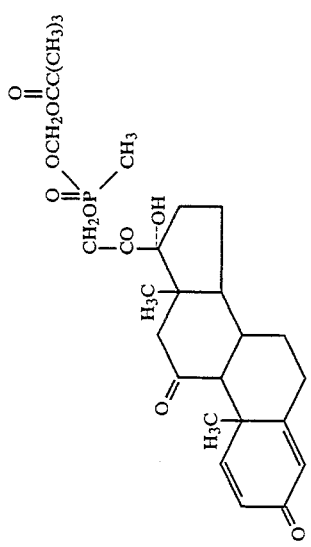
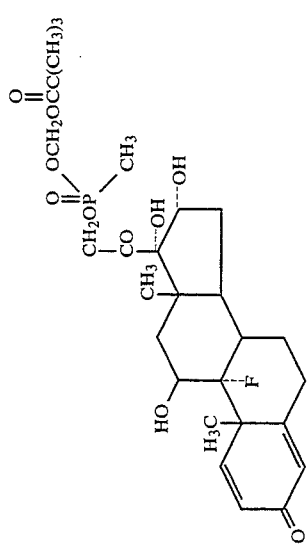
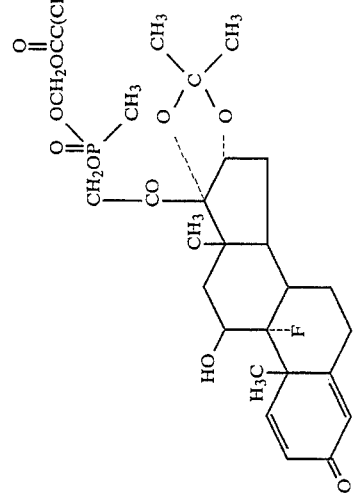
-continued
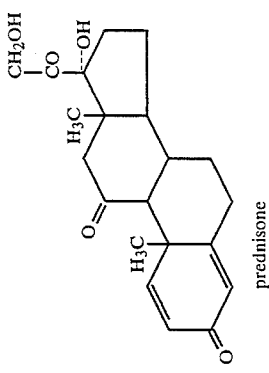
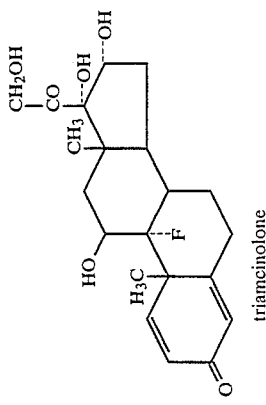
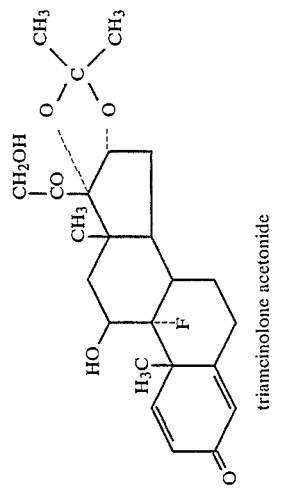
prednisone
triamcinolone
triamcinolone acetonide

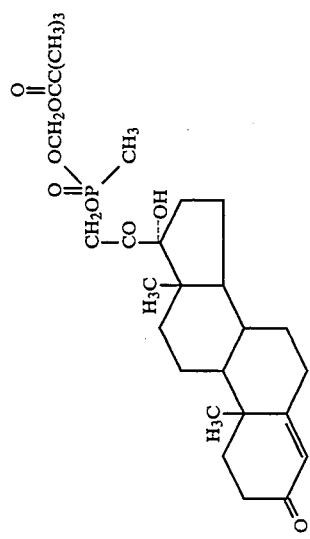
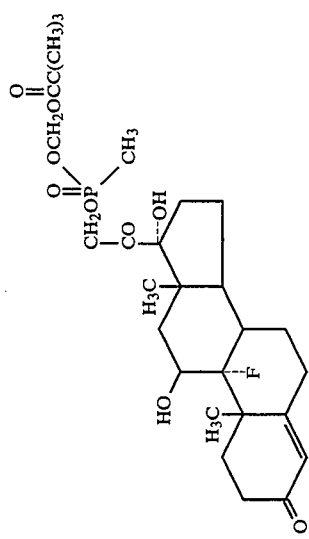
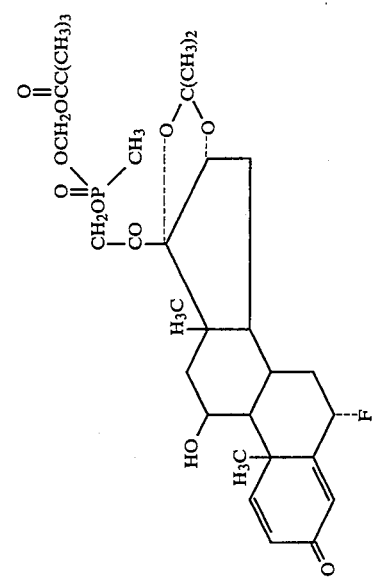
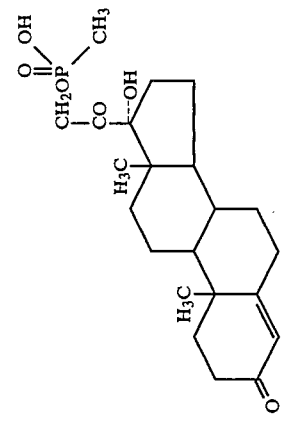
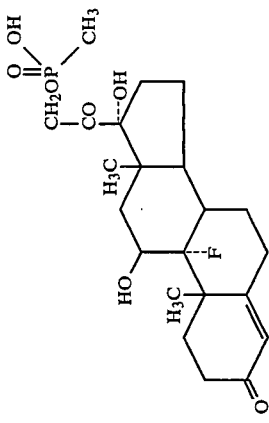
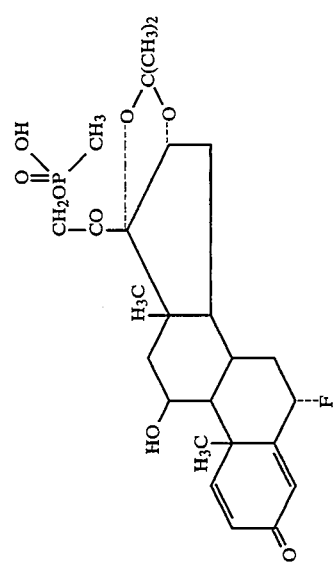
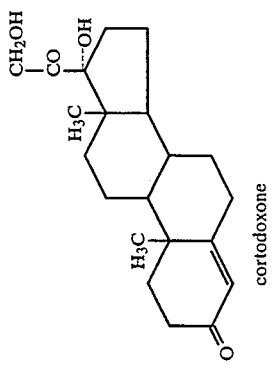
cortodoxone
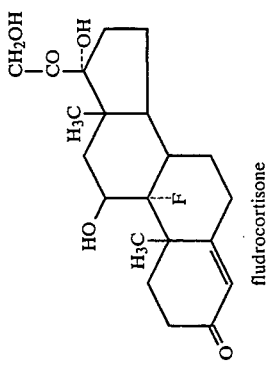
fludrocortisone
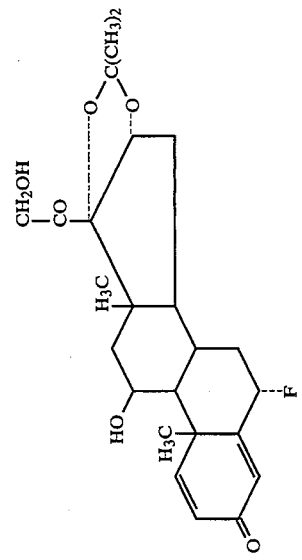
flurandrenolide (flurandrenolone acetonide)

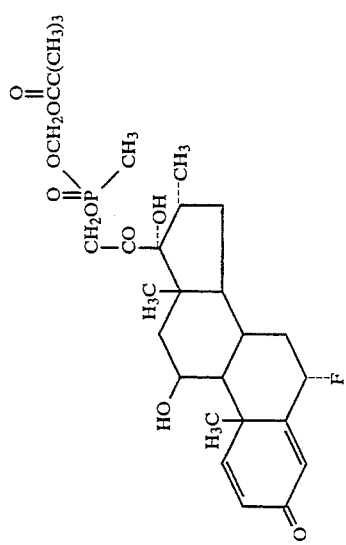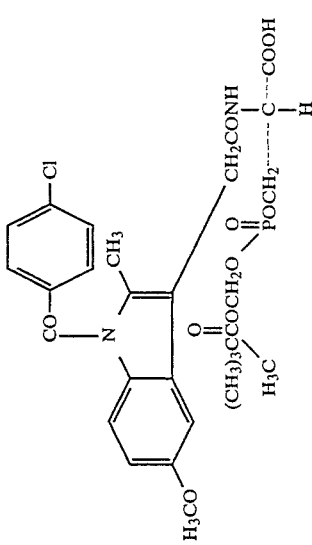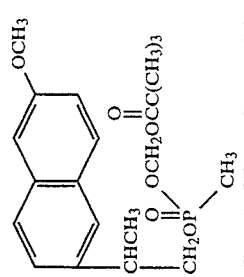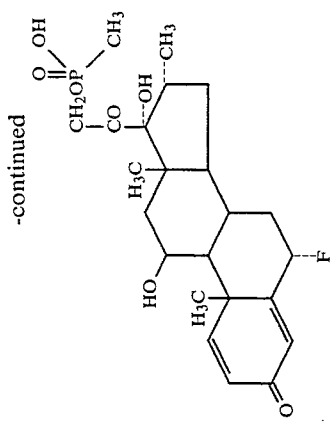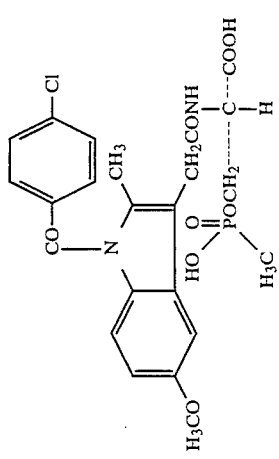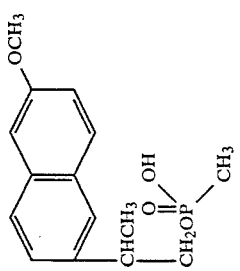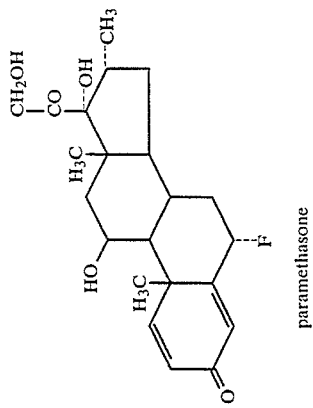
paramethasone
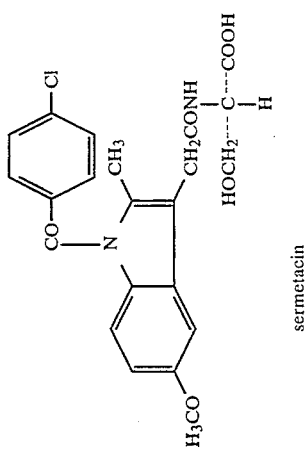
sermetacin
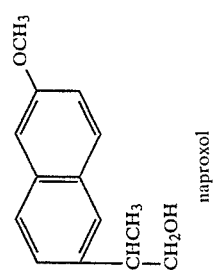
naproxol In the process of METHOD A described above, the intermediates and final products shown are not always the only intermediates and final products obtained in significant amounts; yet other intermediates and final products of formulas (Ia) and (Ib) may be obtained which are encompassed by the present invention.

Thus, for example, when the drug containing a reactive hydroxyl or mercapto function also contains a reactive imide or amide function, in addition to the major product which is depicted above, there may be isolated a minor product in which the hydroxy function is derivatized as shown while the amide or imide function is acyloxyalkylated. The minor product will be produced in a larger amount if excess

or analogous reagent is employed in the Emil step. In the case of zidovudine (AZT), the minor product resulting from METHOD A has the formula

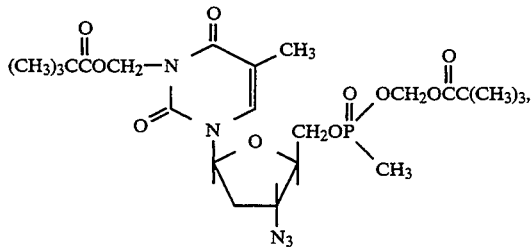

while the major product is that depicted with METHOD A. Drugs such as tiazofurin, 5-FUDR (floxuridine), ribavirin, 6-azauridine, acyclovir, 3-deazaguanosine, ganciclovir (DHPG), 6-azauridine, idoxuridine, trifluridine, dideoxyinosine (DDI), dideoxydehydrothymidine, BVDU, FIAU, FMAU, FIAC, Ara-T, FEAU, selenazofurin and buciclovir (DHBG) may be acyloxyalkylated at the amide or imide nitrogen in a similar manner to zidovudine; derivatives of this type are even more lipophilic than the major products depicted hereinabove where the imide or amide group is unreacted.

As another example, when the selected drug contains multiple reactive hydroxyl functions, a mixture of intermediates and final products may again be obtained. In the unusual case in which all hydroxy groups are equally reactive, there is not expected to be a predominant product (unless all would give the same product, e.g. ganciclovir), as each mono-substituted product will be obtained in approximate by equal amounts, while a lesser amount of multiply-substituted product will also result. Generally speaking, however, one of the hydroxyl groups will be more susceptible to substitution than the other(s), e.g. a primary hydroxyl will be more reactive than a secondary hydroxyl, an unhindered hydroxyl will be more reactive than a hindered one. Consequently, the major product will be a mono-substituted one in which the most reactive hydroxyl has been derivatized while other mono-substituted and multiply-substituted products may be obtained as minor products. In this instance, too, control of the amount of

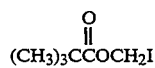

or analogous reagent affects the amounts of the various products obtained. Drugs which may afford other hydroxy-substituted (mono- or multiply-substituted) derivatives in addition to those depicted for METHOD A include pentostatin (2'-deoxycoformycin), vidarabine (An-A), 5-FUDR (floxuridine), cytarabine (Ara-C), apomorphine, morphine, nalbuphine, nalorphine, buprenorphine, (S)-9-(2,3-dihydroxypropyl)adenine, ganciclovir (DHPG), idoxuridine, trifluridine, BVDU, FIAU, FMAU, FIAC, Ara-T, FEAU, cyclaradine, buciclovir (DHBG), ethinyl estradiol, estradiol, ethynodiol, cortisone, hydrocortisone, betamethasone, dexamethasone, flumethasone, fluprednisolone, methylprednisolone, meprednisone, prednisolone, prednisone, triamcinolone, triamcinolone acetonide, cortodoxone, fludrocortisone, flurandrenolide, paramethasone and the like.

In the special instance in which the selected drug contains multiple reactive hydroxyl functions which are positioned in such a manner that they may form an undesired cyclic product when subjected to the process of METHOD A, a synthetic route other than that of METHOD A may be generally preferred. Thus, in the case of nucleoside-type antivirals and antineoplastics having hydroxyls at both the 2'- and 3'-positions as well as at the 5'-position, a product which is derivatized only at the 5'-position (i.e. as depicted with METHOD A) is preferred, and such product is most advantageously produced by use of a transitory protecting group such as the acetonide group described in METHOD F hereinbelow. Drugs such as dihydro-5-azacytidine, tiazofurin, 6-MMPR, 5-azacytidine, ribavirin, 3-deazaguanosine, 6-azauridine, 5,6-dichoro-1-$\beta$-D-ribofuranosylbenzimidazole, 5,7-dimethyl-2-$\beta$-D-ribofuranosyl-s-triazole (1,5a)pyrimidine, 3-deazauridine, 6-azauridine, 3-deazaaristeromycin, neplanocin A, selenazofurin and 3-deazaadenosine thus are preferably subjected to METHOD F to afford the preferred 5'-derivatized products depicted with METHOD A.

METHOD B

The process of METHOD A is repeated, except that an equivalent quantity of phenyl phosphonic dichloride is used in the first step in place of methyl phosphonic dichloride. When each of the representative starting materials listed with METHOD A is subjected to this process, the intermediate phosphonic acid derivative has the partial formula

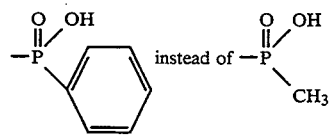

as depicted in the intermediate column, and the final product of formula (Ia) or (Ib) is as depicted in METHOD A, except that the

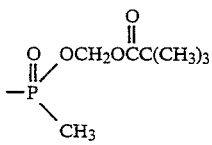

portion of the product is replaced with

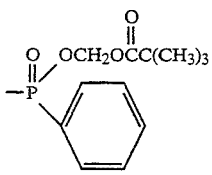

in each instance.

METHOD C

The process of METHOD A is repeated, except that in the second step the

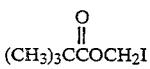

reactant is replaced with an equivalent quantity of

When each of the representative starting materials listed with METHOD A is subjected to this process, each of the intermediate phosphonic acid derivatives is as depicted in the intermediate column, while the corresponding final product of formula (Ia) or (Ib) differs from that depicted in METHOD A in that the

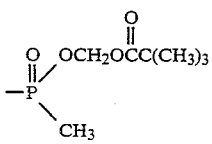

portion of each product is replaced with

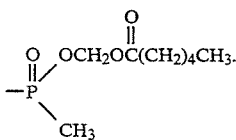

METHOD D

The process of METHOD A is repeated, except that in the second step the

reactant is replaced with an equivalent quantity of

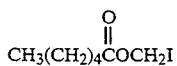

When each of the representative starting materials listed with METHOD A is subjected to this process, each of the intermediate phosphonic acid derivatives is as depicted in the intermediate column, while the corresponding final product of formula (Ia) or (Ib) differs from that depicted in METHOD A in that the

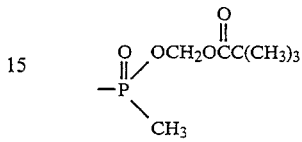

portion of each product is replaced with

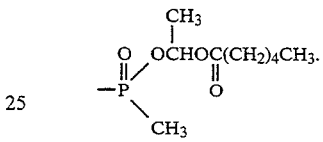

METHOD E

This is a modification of the basic method described in METHODS A–D for drugs containing multiple hydroxyl substituents, particularly for the nucleoside-type antivirals and antineoplastics. The drug selected as the starting material contains one primary hydroxyl substituent and one or more secondary hydroxyl substituents. When the drug is a nucleoside-type containing a ribofuranosyl grouping, the primary hydroxyl is in the 5'-position, while the secondary hydroxyl(s) is/are in the 2'- and/or 3'-position(s). Drugs of this type are exemplified by, but not limited to, vidarabine, cytarabine, ribavirin, 3-deazaguanosine, idoxuridine, BVDU, FIAU, FMAU and the like.

The selected nucleoside starting material as described above is reacted with 4,4'-dimethoxytrityl chloride to give the 5'-(4,4'-dimethoxytrityl)ether derivative. The 2'- and/or 3'-hydroxy group is then esterified by reaction with a variety of acid anhydrides such as pivaloyl, benzoyl, isobutyryl or acetyl to give the 2'- and/or 3'-ester groupings. The resultant compound is then treated with acetic acid to regenerate the 5'-hydroxy moiety. The 2'- and/or 3'-protected compound with a free 5'-hydroxy group is thereafter utilized as the starting material in the process of any of METHODS A–D to give the compound of the invention with a phosphonate moiety at the 5'-position and protected ester grouping(s) at the 2'- and/or 3'-position(s).

METHOD F

A starting material with multiple hydroxyl substituents is selected as described in the first paragraph of METHOD E, except that the selected compound must contain hydroxyls at both the 2'- and 3'-positions as well as the 5'-position, e.g. ribavirin, 3-deazaguanosine or the like. Reaction with acetone gives the 2',3'-O-acetonide. That protected intermediate can then be used as the starting material in the process of any of METHODS A–D, followed by, if desired, removal of the acetonide protecting group with formic acid, to give the same compound of the invention as depicted as the final product of METHOD A.

METHOD G

This is a variation of METHODS A–D used when the drug also contains one or more —COOH function(s) which is/are to be protected.

The drug, e.g. a valproic acid metabolite such as 5-hydroxy-2-n-propylpentanoic acid, sermatacin or the like, is first converted to the corresponding ethyl, t-butyl or similar ester grouping by well-known esterification methods. That ester is then used as the starting material and METHOD A, B, C or D is repeated to give the desired compound of the invention.

II. Methods for Derivatizing Imide or Amide Functions in Drugs

METHOD H

The drug containing a reactive amide or imide functional group is reacted with formaldehyde in the presence of potassium carbonate or other suitable basic catalyst, converting the

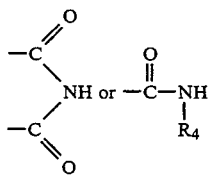

group in the imide or amide, respectively, to a

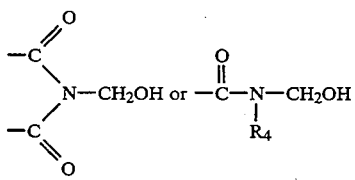

grouping. The resultant drug with bridging group appended (hereinafter referred to as the "bridged drug") is then subjected to the two-step process as described in METHOD A above. The representative drugs depicted below ("Starting Material") may be derivatized in this manner, fast to the bridged drug (not shown), then to the phosphonic acid intermediate ("Intermediate") and finally to the corresponding compound of formula (Id) or (Ie) ("Final Product").

Obviously, the variations of METHOD A described in METHODS B, C and D can be readily applied to the bridged drugs prepared in the fast step of METHOD H, affording yet other compounds of formulas (Id) and (Ie).

| Starting Material | Intermediate | Final Product |
|---|---|---|
| fluorouracil (5-FU) | | |
| phenytoin | | |
| ethotoin | | |
| mephenytoin | | |
| phenobarbital | | |

| Starting Material | Intermediate | Final Product |
|---|---|---|
| uracil mustard | | |
| chlortetracycline | | |
| glutethimide | | |
| tesicam | | |

-continued

| Starting Material | Intermediate | Final Product |
|---|---|---|
| spiromustine | | |
| desmethyldiazepam | | |
| oxazepam | | |

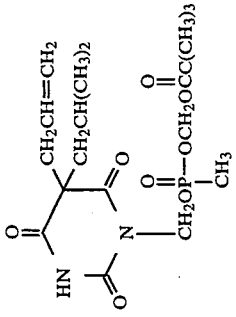

| Starting Material | Intermediate | Final Product |
|---|---|---|
| aminoglutethimide | | |
| bemegride | | |
| nitrazepam | | |

| Starting Material | Intermediate | Final Product |
|---|---|---|
| bromazepam | | |

METHOD I

The process of METHOD H is repeated, except that acetaldehyde is used in the first step in place of formaldehyde. The bridged drug of the type

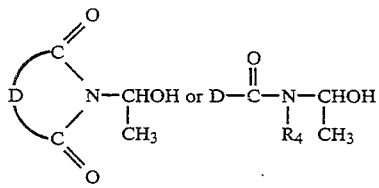

is then subjected to the two-step process described in METHOD A to afford the corresponding compounds of formulas (Id) and (Ie).

This process can be readily modified in the manner described in the final paragraph of METHOD H to give yet other compounds of formula (Id) and (Ie).

III. Methods for Derivatizing Carboxyl Functions in Drugs

METHOD J

The drug containing a reactive carboxyl functional group is reacted with 1-chloroethyl chlorosulfate to convert the —COOH group to a

substituent, which is then reacted with the mono- or di-cesium salt of

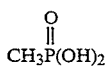

to afford the corresponding phosphonic acid intermediate. That intermediate is then subjected to the final step of the process described in METHOD A, using cesium fluoride and

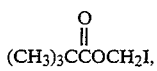

to afford the desired compound of formula (Ic). The representative drugs depicted below ("Starting Material") may be derivatized in this manner, first to the chloroethyl derivative (not shown), then to the phosphonic acid intermediate ("Intermediate") and finally to the corresponding compound of formula (Ic) ("Final Product").

Obviously, the foregoing procedure can be modified in many ways, e.g. by varying the final step as described in METHOD C, affording yet other compounds of formula (Ic).

| Starting Material | Intermediate | Final Product |
|---|---|---|
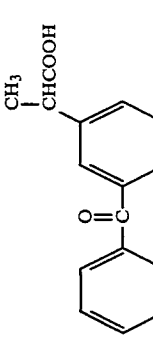

-continued

| Starting Material | Intermediate | Final Product |
|---|---|---|
| chlorambucil | | |
| methotrexate | | |
| carbenicillin | | |

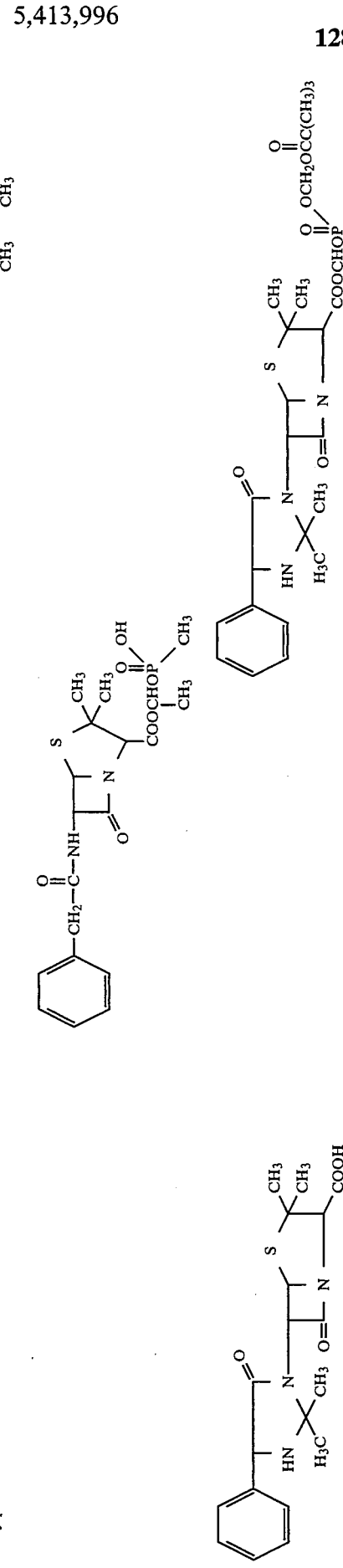

-continued
| Starting Material | Intermediate | Final Product |
|---|---|---|
| 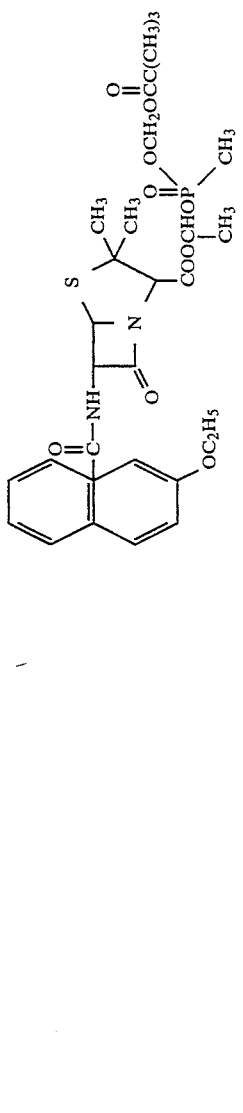 nafcillin | 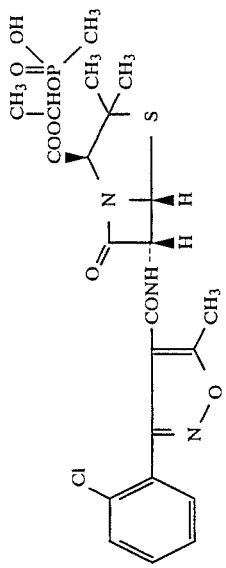 | 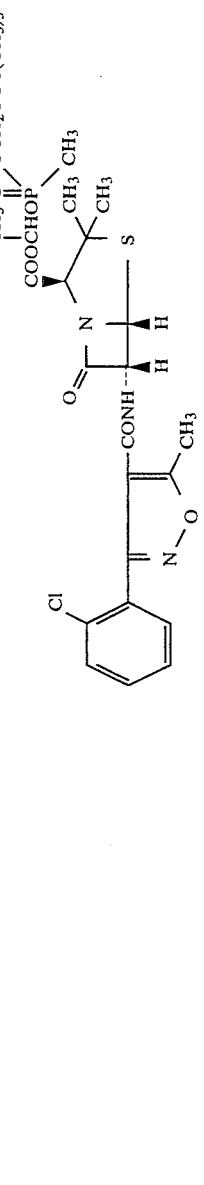 |
| 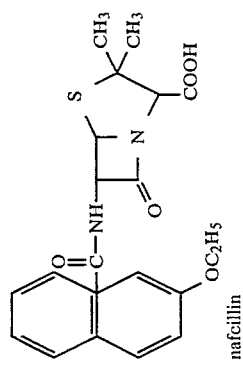 cloxacillin | | 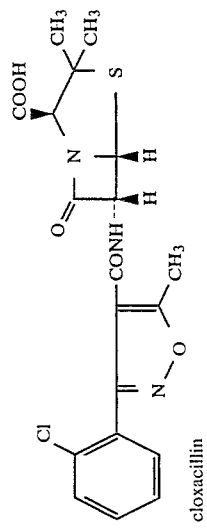 |

| Starting Material | Intermediate | Final Product |
|---|---|---|
| cephalothin | | |
| cefoxitin | | |
| ibuprofen | | |

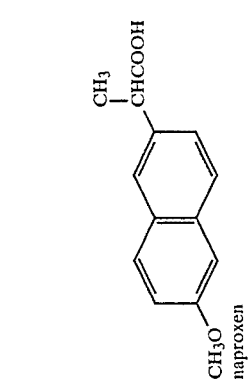

| Starting Material | Intermediate | Final Product |
|---|---|---|
| 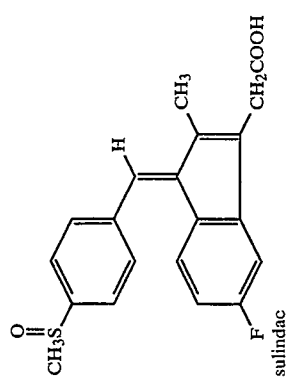<br>sulindac | 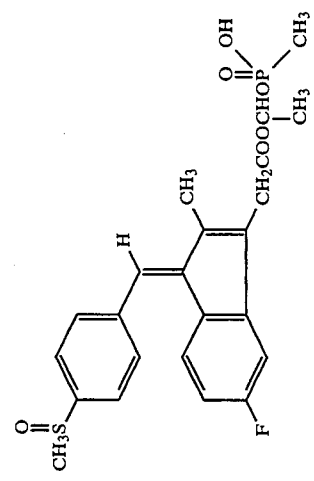 | 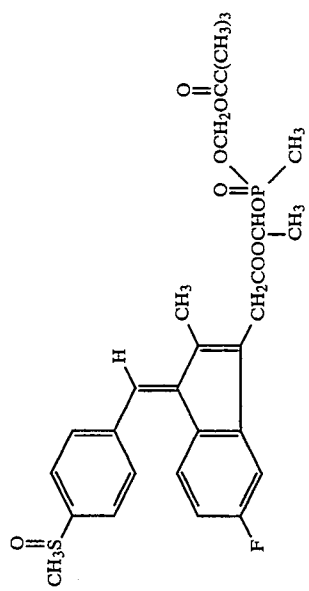 |
| 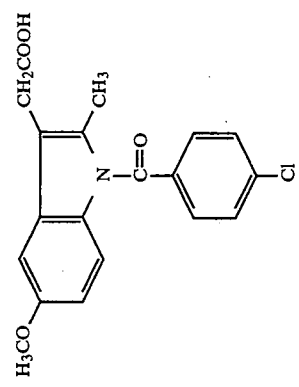<br>indomethacin | | 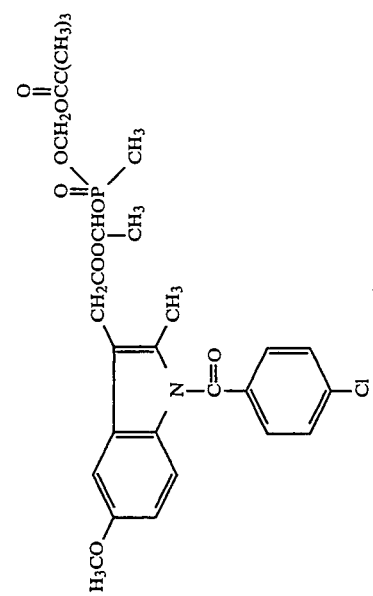 |

-continued
| Starting Material | Intermediate | Final Product |
|---|---|---|
| 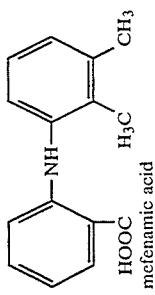 mefenamic acid | 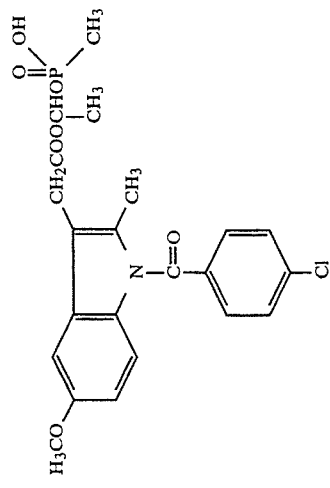 | 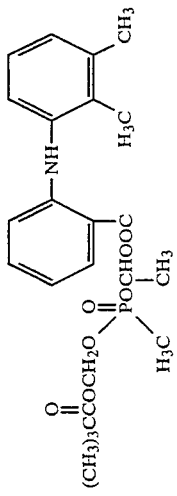 |
| 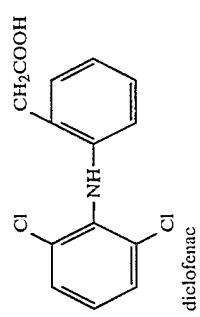 diclofenac | 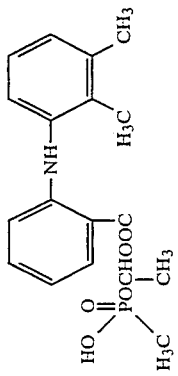 | 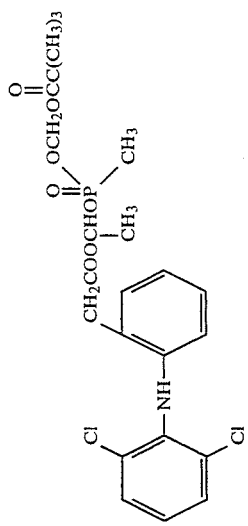 |

| Starting Material | Intermediate | Final Product |
|---|---|---|

METHOD K

When the drug containing a reactive carboxyl functional group is sufficiently bulky, it can hinder the —O—Z—O— bridging group. In such a case, Z can be, and preferably is selected to be —CH₂—, and METHOD J is modified by replacing the 1-chloroethyl chlorosulfate reactant in the first step with chloromethyl sulfate, and otherwise proceeding as detailed in that method. Drags such as oxacillin, carbenicillin, benzylpenicillin, hetacillin, nafcillin, cloxacillin, cephalothin and cefoxitin can be derivatized in this manner, first to the corresponding chloromethyl derivative by converting the —COOH group to a —COOCH₂Cl group, then to the phosphinic acid intermediate of the partial structure

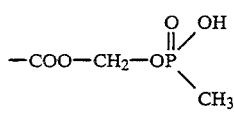

and then to the desired compound of formula (Ic) having the partial formula

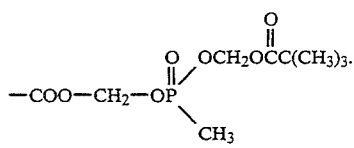

This method can of course be modified in many ways, e.g. by varying the final step as described in METHOD C.

IV. Methods for Derivatizing Amino Functions in Drugs

METHOD L

The drug containing a reactive amino functional group is reacted with 1-chloroethyl chloroformate,

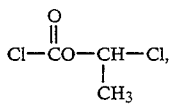

to replace a hydrogen atom of the drug's amino group with a

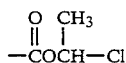

grouping. Subsequent reaction with the mono- or di-cesium salt of

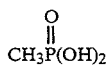

affords the corresponding phosphonic acid intermediate. That intermediate is then subjected to the final step of the process described in METHOD A, using cesium fluoride and

to afford the desired compound of formula (If). The representative drugs depicted below ("Starting Material") may be derivatized in this manner, first to the 1-chloroethoxycarbonyl derivative (not shown), then to the phosphonic acid intermediate ("Intermediate") and finally to the corresponding compound of formula (If) ("Final Product").

The foregoing procedure can be modified in many ways, for example by varying the final step as described in METHOD C, affording yet other compounds of formula (If). Further, when the drug is sufficiently bulky, the process of METHOD L may be modified by utilizing chloromethyl chloroformate as the reactant in the first step.

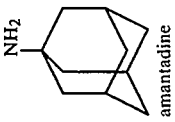

-continued

-continued

| Starting Material | Intermediate | Final Product |
|---|---|---| phenmetrazine d-isomer
dextroamphetamine l-isomer
levamphetamine phenylethylamine
(phenethylamine)

amphetamine

-continued

| Starting Material | Intermediate | Final Product |
|---|---|---|

| Starting Material | Intermediate | Final Product |
|---|---|---|

METHOD M

This is a variation of METHOD L used when the chug also contains one or more —COOH functions which is/are to be protected.

The drug, e.g. GABA, melphalan, tryptophan or the like, is first converted to the corresponding ethyl, t-butyl or similar ester grouping by well-known esterification methods. That ester is then used as the starting material and METHOD L is repeated to give the desired compound of the invention.

In order to further illustrate the compounds of the invention and the methods for their preparation, the following synthetic examples are given, it being understood that same are intended only as illustrative, as many modifications in materials and methods will be apparent to those skilled in the art.

In the examples to follow, all melting points were taken on a Mel-Temp apparatus and are not corrected. Elemental analyses were performed at Atlantic Microlabs, Inc., Atlanta, Ga.

EXAMPLE 1

A solution of testosterone (5 g, 17.4 mmol) in dry pyridine (17 mL) was added dropwise at −3 to 0° C. over a 25 minute period to a stirred solution of methylphosphonic dichloride, $CH_3P(O)Cl_2$ (4.6 g, 34.7 mmol). The resultant mixture was stirred for one hour at room temperature, then poured into ice water, neutralized with sodium bicarbonate and extracted with two 175 mL portions of ether. The ether extracts were washed with 175 mL of saturated aqueous sodium bicarbonate solution. The aqueous layer was acidified with 4N hydrochloric acid while cooling in an ice bath. The flask was stored in a refrigerator overnight. The white precipitate which formed was removed by filtration, washed with cold water and dried under vacuum at 50° to 60° C. Yield 4.31 g, 68%. Recrystallization of a portion of the product with aqueous methanol gave crystals melting at 198°–201° C. NMR values were consistent with the assigned structure:

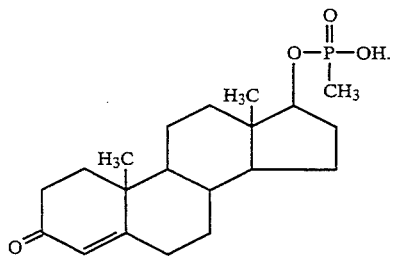

EXAMPLE 2

The phosphonic acid derivative produced in EXAMPLE 1 (4.3 g, 11.7 mmol) was dissolved in 2N aqueous sodium hydroxide solution (6.16 mL, 12.32 mmol). A few drops of phenolphthalein solution were added and the alkaline solution was neutralized with 2N nitric acid until the red color due to phenolphthalein disappeared. Then, a solution of silver nitrate (2.0 g, 11.7 mmol) in 6 mL of water was added in the dark. The resultant mixture was allowed to stand in the dark overnight. The precipitate which formed was removed by filtration and washed with cold water, also in the dark. The grayish white material was dried in vacuo in the dark at 60° to 80° C. and was used in the procedure of EXAMPLE 3 below without further purification. The crude silver salt, obtained in 98% yield (5.47 g), had the structural formula:

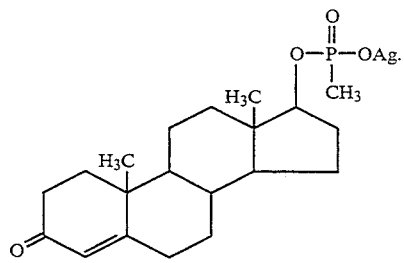

EXAMPLE 3

Sodium iodide (24.73 g, 165 mmol) was added to a solution of chloromethyl pivalate (5 g, 33 mmol) in dry acetone (40 mL). The mixture was stirred for 4 hours at room temperature. Insoluble materials were removed by filtration and washed with fresh acetone. The filtrate was evaporated, and hexane and 5% aqueous sodium thiosulfate solution were added to the residue. The mixture was thoroughly shaken, then the organic layer was separated and washed with 5% aqueous sodium thiosulfate solution. Drying over sodium sulfate, followed by evaporation of the solvent, afforded 7.03 g (88% yield) of yellow liquid which was used in the procedure of EXAMPLE 4 without further purification. The structure of the product, $(CH_3)_3CCOOCH_2I$, was confirmed by NMR analysis.

EXAMPLE 4

Crude iodomethyl pivalate (160 mg, 0.66 mmol) was dissolved in 2 mL of benzene and washed successively with 5% aqueous sodium thiosulfate (1 mL) and water (1 mL×3) and dried over anhydrous sodium sulfate. That solution was dropped into a stirred suspension of the silver salt obtained in EXAMPLE 2 (250 mg, 0.53 mmol) in 5 mL of dry benzene under nitrogen in the dark over a seventeen minute period. The resultant mixture was stirred at room temperature overnight. Insoluble materials were removed by filtration and the filtrate was washed, once with sodium thiosulfate solution and three times with water, then dried over magnesium sulfate. Evaporation of the solvent gave a yellowish viscous oil. The crude product was purified by column chromatography on silica gel, using 1:1 hexane-ethyl acetate as eluent. A slightly yellow viscous oil was obtained in 31% yield (80 mg). NMR values were consistent with the assigned structure:

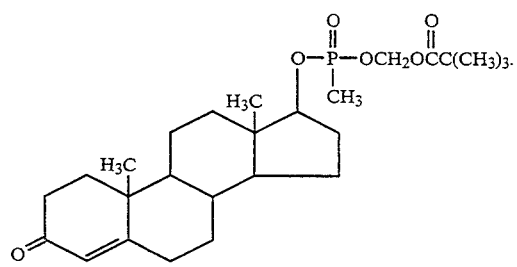

EXAMPLE 5

To a mixture of hexanoyl chloride (25 g, 0.186 mol) and paraformaldehyde (5.58 g, 0.186 mol) in an ice bath was added a catalytic quantity (550 mg) of zinc chloride. An exothermic reaction resulted. After the reaction subsided, the mixture was heated at 90° to 100° C. for 4.5 hours. Purification by reduced distillation gave 22.79 g of the desired compound as a colorless liquid in 75% yield, boiling point 37°–40° C./0.55 min. NMR analysis confirmed the identity of the product as chloromethyl hexanoate, $CH_3(CH_2)_4COOCH_2Cl$.

EXAMPLE 6

Chloromethyl hexanoate (205 mg, 1.25 mmol) was stirred with sodium iodide (900 mg, 6.0 mmol) in 3 mL of dry acetone for 4 hours at room temperature. Workup followed the procedure detailed in EXAMPLE 3 above for the preparation of iodomethyl pivalate. Iodomethyl hexanoate, $CH_3(CH_2)_4COOCH_2I$, was obtained as a yellow oil in 78% yield. NMR values were consistent with the assigned structure.

EXAMPLE 7

The silver salt prepared in EXAMPLE 2 (4.55 g, 9.66 mmol) was suspended in 60 mL of dry benzene. To the stirred suspension was added a solution of iodomethyl hexanoate (2.95 g, 11.52 mmol) in 15 mL of dry benzene at room temperature under a stream of nitrogen in the dark over a 30 minute period. The resultant mixture was stirred at room temperature overnight. Insoluble materials were removed by filtration and the filtrate was washed, first with 5% aqueous sodium thiosulfate solution and then three times with water. The organic layer was dried over anhydrous magnesium sulfate and then evaporated to give an oily crude product. The crude product was purified by column chromatography on silica gel, using first 2:3 hexane-ethyl acetate and then 3:1 dichloromethane-ethyl acetate as eluents. Obtained in this manner as a pale yellow viscous oil in 21% yield (1.11 g) was the desired phosphonate derivative of the formula

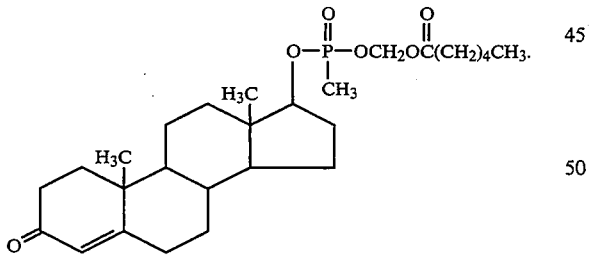

NMR values were consistent with the assigned structure. Anal. calcd. for $C_{27}H_{43}O_6P$: C, 65.57; H, 8.76. Found: C, 65.38; H, 8.84.

EXAMPLE 8

Zidovudine (10.0 g, 37.4 mmol), sodium carbonate (11.9 g, 112 mmol), methylphosphonic dichloride (14.9 g, 112 mol) and acetone (50 mL) were combined under a stream of nitrogen, and the mixture was stirred at room temperature for 17 hours. To the ice-cooled, stirred residual mixture, water (4.0 mL, 225 mmol) was added dropwise, followed by 60 mL of methanol. To the resultant suspension was added Florisil®(100 g), and the mixture was evaporated to dryness. The crude material was purified by column chromatography on Florisil®(200 g) with dichloromethane-methanol (20-1:1, gradation) as an eluent to give 4.33 g of a crude amorphous solid. The crude solid was dissolved in methanol (21.6 mL), then 216 mL of ether were added. The precipitate which formed was collected by filtration and washed with ether. The resulting pale yellow amorphous solid was dried in vacuo and used in the procedure of EXAMPLE 9 without further purification. Yield 31.3% (4.05 g). NMR values were consistent with the assigned structure:

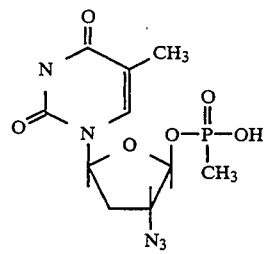

EXAMPLE 9

The phosphonic acid derivative produced in EXAMPLE 8 (4.50 g, 13 mmol), cesium fluoride (4.41 g, 29 mmol), freshly prepared iodomethyl hexanoate (6.68 g, 26 mmol) and dimethylformamide (45 mL) were mixed under a stream of nitrogen and stirred at room temperature for 19.5 hours. The reaction mixture was then poured into 300 mL of ether and washed successively with water (100 mL), 5% aqueous sodium thiosulfate solution (100 mL) and again with water (100 mL). Each aqueous layer was extracted with one 100 mL portion of ether. The ether layers were combined, dried over magnesium sulfate, filtered and concentrated to give 3.95 g of brown oil. The crude material was purified by column chromatography on silica gel (40 g) using hexane-ethyl acetate (1 to ~0:1, gradation) as eluent to give 1.03 g of a slightly yellow viscous oil (16.7% yield). The product, whose structure was confirmed by NMR and elemental analyses, had the formula:

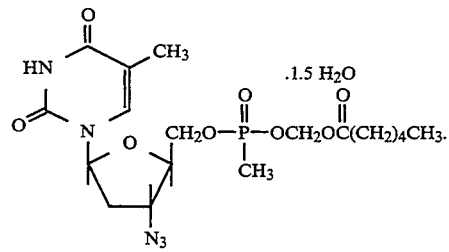

Anal. calcd. for $C_{18}H_{31}N_5O_{9.5}P$: C, 43.20; H, 6.24; N, 13.99. Found: C, 42.94; H, 5.95; N, 14.12.

EXAMPLE 10

Hexanoyl chloride (5.5 mL, 37 mmol) and acetaldehyde (4.2 mL, 74 mmol) were combined under a stream of nitrogen and stirred in an ice bath. To that solution was added a catalytic quantity of zinc chloride. Within 30 seconds, an exothermic reaction (−8° C.→43° C.) occurred. The reaction mixture was maintained in an ice bath for 30 minutes, then was poured into 100 mL of hexane. The hexane solution was washed successively with saturated aqueous sodium bicarbonate solution (2×50 mL) and saturated aqueous sodium chloride solution (50 mL). The organic layer was separated, dried over magnesium sulfate, filtered and concentrated to give 7.81 g of 1'-chloroethyl hexanoate, $CH_3(CH_2)_4COOCH(CH_3)Cl$, as a slightly yellow oil. It was used in the procedure detailed in EXAMPLE 11 below without further purification. NMR analysis continued the identity of the product.

EXAMPLE 11

Sodium iodide (27.9 g, 186 mmol) and acetonitrile (39 mL) were combined under a stream of nitrogen and stirred at a temperature below 10° C. To that solution was added dropwise 1'-chloroethyl hexanoate (7.80 g) in 39 mL of acetonitrile at a temperature below 10° C. The reaction mixture was stirred for 3 days at 0° to 10° C. Insoluble materials were removed by filtration and washed with acetonitrile. The filtrate was evaporated and hexane (100 mL) and water (100 mL) were added to the residue. The mixture was thoroughly shaken, then the organic layer was separated and washed successively with 5% aqueous sodium thiosulfate solution (100 mL×2) and water (100 mL). Each aqueous layer was extracted with one 50 mL portion of hexane. The hexane layers were combined, dried over magnesium sulfate, filtered and concentrated to give 7.77 g of yellow oil (77.5% yield). The crude 1'-iodoethyl hexanoate, $CH_3(CH_2)_4COOCH(CH_3)I$, was used in the procedure of EXAMPLE 12 without further purification. NMR analysis confirmed the identity of the product.

EXAMPLE 12

The phosphonic acid derivative of testosterone prepared in EXAMPLE 1 (2.20 g, 6 mmol), 1'-iodoethyl hexanoate (3.24 g, 12 mmol), cesium fluoride (2.01 g, 13.2 mmol) and dimethylformamide (22 mL) were combined under a stream of nitrogen. The mixture was stirred in a water bath for 3 days. Work-up followed the procedure detailed in EXAMPLE 9 above for the preparation of the zidovudine derivative. The crude material was purified by column chromatography on silica gel (42 g), using 1:1 hexane-ethyl acetate as eluent, to give 0.39 g (12.8% yield) of the desired product of the formula

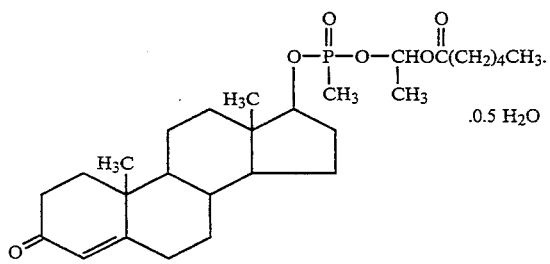

The identity of the product was confirmed by NMR and elemental analyses. Anal. calcd. for $C_{28}H_{46}O_{6.5}P$: C, 64.98; H, 9.01. Found: C, 64.97; H, 8.96.

Preliminary biological tests have been conducted on the testosterone phosphonate prepared in EXAMPLE 7 and the zidovudine (AZT) phosphonate prepared in EXAMPLE 9. Incubation of the testosterone phosphonate in various organ homogenates leads to a rapid decomposition of the acyloxyalkyl phosphonate ester. The half-life of the material is approximately 320 seconds in rat blood, 460 seconds in rat brain homogenate and 120 seconds in rat liver homogenate. The disappearance of the ester is associated with the appearance of the testosterone methyl phosphonate. In a preliminary in vivo study, conversion of the administered acyloxyalkyl phosphonate of testosterone to both testosterone and testosterone methyl phosphonate was detected in various organs, and specifically in the brain. In the case of the zidovudine derivative, the methyl phosphonate derivative was similarly detected in the brain.

The compounds of formula (I) which are provided by this invention are typically administered to mammals by incorporating the selected compound into a pharmaceutical composition comprising the compound or a non-toxic pharmaceutically acceptable salt thereof and a non-toxic pharmaceutically acceptable carrier therefor. The compound or its salt is employed in an effective amount, i.e. an amount sufficient to evoke the desired pharmacological response. The compounds of the invention are designed to elicit the kind of pharmacological response which would be obtained by delivery of the parent drug itself to the desired site of action, especially to the brain. Thus, for example, when the parent drug is an antiviral, the derivative of formula (I) will be administered in an amount sufficient to elicit an antiviral response; when the parent drug is an antineoplastic, the derivative of formula (I) will be employed in an amount sufficient to elicit an antineoplastic, i.e. anticancer or antitumor, response; when the parent drug is an antibiotic, the derivative of formula (I) will be used in an amount sufficient to evoke an antibiotic response; when the parent drug is asteroid sex hormone, the derivative of formula (I) will be used in an amount sufficient to evoke an androgenic or estrogenic or progestational effect (depending on the identity of the parent drug); when the parent drug is an antiinflammatory agent, the derivative of formula (I) will be administered in an amount sufficient to elicit an antiinflammatory response; and so forth.

Suitable non-toxic pharmaceutically acceptable carriers for use with the selected compound of formula (I) will be apparent to those skilled in the an of pharmaceutical formulation. See, for example, Remington's Pharmaceutical Sciences, seventeenth edition, ed. Alfonso R. Gennaro, Mack Publishing Company, Easton, Pa. (1985). Obviously, the choice of suitable carriers will depend upon the exact nature of the particular dosage form selected, as well as upon the identity of the compound to be administered. The therapeutic dosage range for a compound according to this invention will generally be the same as, or less than, that which would characteristically be used for administration of the parent drug itself. Naturally, such therapeutic dosage ranges will vary with the particular compound of formula (I) used, the size, species and condition of the subject, the severity of the subject's condition, the particular dosage form employed, the route of administration and the like. And the quantity of given dosage form needed to deliver the desired dose will of course depend upon the concentration of the compound of formula (I) in any given pharmaceutical composition/dosage form thereof. In addition, to further enhance the site-specificity of the compounds of the invention, the active ingredient may be formulated into a sustained release carrier system and/or a route of administration may be selected to slowly release the chemical, e.g. subcutaneous implantation or transdermal delivery.

Routes of administration contemplated for the compounds of formula (I) and pharmaceutical compositions containing them are any of the routes generally used for treatment of the types of conditions for which the parent drugs are administered. These include parenteral (intravenous, intramuscular, subcutaneous), vaginal, rectal, nasal, oral and buccal routes. Appropriate dosage forms for these routes of administration will be apparent to those skilled in the art.

Obviously, in the case of diagnostic agents, the dosage of the formula (I) compound used will be a quantity sufficient to deliver to the target body area an amount of radioisotope, stable isotope or the like which can be effectively detected by radioimaging or other detection means. The amount of radioisotope, stable isotope or the like present in the dosage form will be within or below the ranges conventionally used for diagnostic purposes.

While the invention has been described in terms of various preferred embodiments, the skilled artisan will appreciate that various modifications, substitutions, omissions and changes may be made without departing from the spirit thereof. Accordingly, it is intended that the scope of the present invention be limited solely by the scope of the following claims.

What is claimed is:

1. A compound of the formula

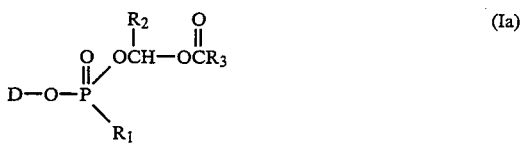

or a pharmaceutically acceptable salt thereof, wherein D—O— is the residue of a drug having a reactive hydroxyl functional group, said drug being asteroid sex hormone or an antiinflammatory steroid, the oxygen atom of said functional group being bonded to the phosphorus atom of the

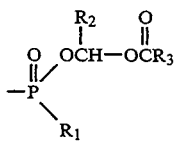

moiety; $R_1$ is $C_1$-$C_8$ alkyl, $C_6$-$C_{10}$ aryl or $C_7$-$C_{12}$ aralkyl; $R_2$ is hydrogen, $C_1$-$C_8$ alkyl, $C_6$-$C_{10}$ aryl, $C_4$-$C_9$ heteroaryl, $C_3$-$C_7$ cycloalkyl, $C_3$-$C_7$ cycloheteroalkyl or $C_7$-$C_{12}$ aralkyl; and $R_3$ is selected from the group consisting of $C_1$-$C_8$ alkyl; $C_2$-$C_8$ alkenyl having one or two double bonds; ($C_3$-$C_7$ cycloalkyl)—$C_rH_{2r}$— wherein r is zero, one, two or three, the cycloalkyl portion being unsubstituted or bearing 1 or 2 $C_1$-$C_4$ alkyl substituents on the ring portion; ($C_6$-$C_{10}$ aryloxy)$C_1$-$C_8$ alkyl; 2-, 3- or 4-pyridyl; and phenyl—$C_r$—$H_{2r}$— wherein r is zero, one, two or three and phenyl is unsubstituted, or is substituted by 1 to 3 alkyl each having 1 to 4 carbon atoms, alkoxy having 1 to 4 carbon atoms, halo, trifluoromethyl, dialkylamino having 2 to 8 carbon atoms or alkanoylamino having 2 to 6 carbon atoms.

2. The compound according to claim 1, wherein $R_1$ is methyl.

3. The compound according to claim 1, wherein $R_2$ is hydrogen.

4. The compound according to claim 1, wherein $R_3$ is $C_1$-$C_8$ alkyl.

5. The compound according to claim 4, wherein $R_3$ is $(CH_3)_3C$— or $CH_3(CH_2)_4$—.

6. The compound according to claim 1, wherein the drug is asteroid sex hormone.

7. The compound according to claim 6, wherein the steroid sex hormone is an androgen.

8. The compound according to claim 7, wherein the androgen is testosterone or methyl testosterone.

9. The compound according to claim 6, wherein the steroid sex hormone is an estrogen.

10. The compound according to claim 9, wherein the estrogen is mestranol, quinestrol, ethinyl estradiol, estradiol, estrone, estriol, estradiol 3-methyl ether or estradiol benzoate.

11. The compound according to claim 6, wherein the steroid sex hormone is a progestin.

12. The compound according to claim 11, wherein the progestin is norgestrel, norethindrone, ethisterone, dimethisterone, allylestrenol, cingestol, ethynerone, lynestrenol, norgesterone, norvinisterone, ethynodiol, oxogestone, tigestol or norethynodrel.

13. The compound according to claim 1, wherein the drug is an antiinflammatory steroid.

14. The compound according to claim 13, wherein the antiinflammatory steroid is cortisone, hydrocortisone, betamethasone, dexamethasone, flumethasone, fluprednisolone, methyl prednisolone, meprednisone, prednisolone, prednisone, triamcinolone, triamcinolone acetonide, cortodoxone, fludrocortisone, flurandrenolide or paramethasone.

15. The compound according to claim 8, having the structural formula

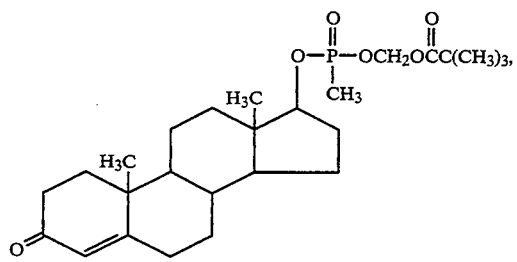

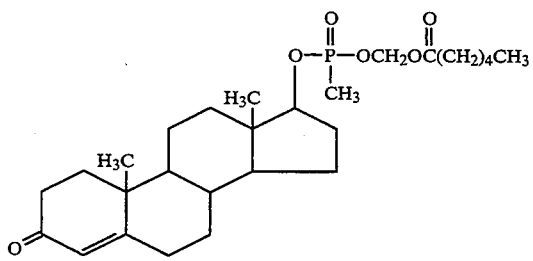

or

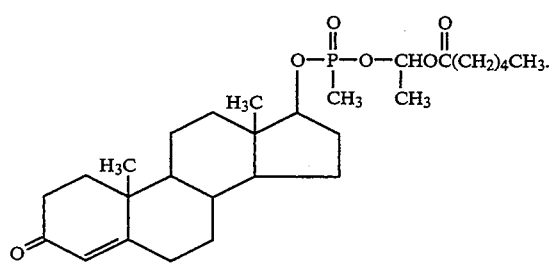

16. A pharmaceutical composition, in unit dosage form, comprising:
(i) an amount of a compound as claimed in claim 1 sufficient to release a pharmacologically effective amount of asteroid sex hormone or antiinflammatory steroid to the brain; and
(ii) a nontoxic pharmaceutically acceptable carder therefor.

17. The pharmaceutical composition as claimed in claim 16, said composition being formulated for sustained release.

* * * * *